(12) United States Patent
Sato et al.

(10) Patent No.: US 7,064,142 B2
(45) Date of Patent: Jun. 20, 2006

(54) IMIDAZONLINE COMPOUNDS

(75) Inventors: Nagaaki Sato, Tsukuba (JP); Osamu Okamoto, Tsukuba (JP); Makoto Jitsuoka, Tsukuba (JP); Keita Nagai, Tsukuba (JP); Akio Kanatani, Tsukuba (JP); Akane Ishihara, Tsukuba (JP); Yasuyuki Ishii, Tsukuba (JP); Takehiro Fukami, Tsukuba (JP)

(73) Assignee: Banyu Pharmaceutical, Co., Ltd., Tokyo (JP)

( * ) Notice: Subject to any disclaimer, the term of this patent is extended or adjusted under 35 U.S.C. 154(b) by 205 days.

(21) Appl. No.: 10/204,267

(22) PCT Filed: Feb. 22, 2001

(86) PCT No.: PCT/JP01/01312

§ 371 (c)(1),
(2), (4) Date: Sep. 25, 2002

(87) PCT Pub. No.: WO01/62738

PCT Pub. Date: Aug. 30, 2001

(65) Prior Publication Data

US 2003/0158418 A1 Aug. 21, 2003

(30) Foreign Application Priority Data

Feb. 22, 2000 (JP) .............................. 2000-045042

(51) Int. Cl.
*A61K 31/415* (2006.01)
*C07D 233/26* (2006.01)
(52) U.S. Cl. .................................... 514/385; 548/347.1
(58) Field of Classification Search ............ 548/347.1; 514/385
See application file for complete search history.

(56) References Cited

U.S. PATENT DOCUMENTS 3,707,475 A 12/1972 Lombardino ................. 260/309
5,880,139 A 3/1999 Chang ......................... 514/326

FOREIGN PATENT DOCUMENTS

WO 99/01128 1/1999
WO 99/48888 9/1999

OTHER PUBLICATIONS

Chemical Abstracts, vol. 52, No. 17240f.
Database, Accession No. 27672, XP002227829 "abstract".
S. Wey et al., "Preparation of Primary Vicinal Diamines from Amino Acid Esters and Crystal Structure of a Chiral Nickel Salen Complex", Tetrahedron Letters, vol. 12, No. 34, pp. 1905-1908, 1993.
R. Granger et al., vol. 250, No. 2, Apr. 4, 1960, pp. 2581-2583, XP002082608.

*Primary Examiner*—Kamal A. Saeed
(74) *Attorney, Agent, or Firm*—Wenderoth, Lind & Ponack, L.L.P.

(57) ABSTRACT

Compounds represented by the general formula (I):

wherein $Ar^1$ and $Ar^2$ are each aryl or heteroaryl; $R^1$ is lower cycloalkyl, —$Ar^3$, or a group of the general formula (a), (b) or (c):

and $R^2$ and $R^3$ are each hydrogen, lower cycloalkyl, lower alkenyl, or optionally substituted lower alkyl (with the proviso that when $R^2$ and $R^3$ are simultaneously hydrogen, $Ar^1$, $Ar^2$ and $R^1$ do not simultaneously represent unsubstituted phenyl). The compounds are useful as treating agents for various NPY-related diseases, for example, circulatory diseases including hypertension, kidney diseases, cardiac diseases, vasospasm and arteriosclerosis; central nervous system diseases including hyperphagia, depression, anxiety, convulsion, epilepsy, dementia, pain, alcohol dependence, and withdrawal symptoms due to abstinence from drugs; metabolic diseases including obesity, diabetes, hormonal disorders, hypercholesterolemia, and hyperlipidemia; sexual dysfunction and reproductive function disorders; digestive diseases including enterokinetic disorders; respiratory diseases; inflammation; or glaucoma.

9 Claims, No Drawings

IMIDAZONLINE COMPOUNDS

This application is a 371 of PCT/JP01/01312 filed Feb. 22, 2001.

TECHNICAL FIELD

The present invention is useful in medical fields. In more detail, novel imidazoline compounds of this invention are useful as neuropeptide Y receptor antagonists and as agents for the treatment of various kinds of cardiovascular disorders, central nervous system disorders, metabolic diseases, or the like.

BACKGROUND ART

Neuropeptide Y (hereinafter referred to as NPY), a peptide consisting of 36 amino acids, was first isolated from porcine brain by Tatemoto et al. in 1982 (Nature, 296: 659(1982)). NPY is widely distributed in the central nervous system and the peripheral nervous system and plays various roles as one of the most abundant peptide in the nervous system. That is, NPY acts as an orexigenic substance in the central nervous system and markedly promotes fat accumulation via the secretion of various hormones or the action of the nervous system. It is known that the continuous intracerebroventricular administration of NPY induces obesity and insulin resistance based on these actions (International Journal of Obesity, vol. 19:517(1995); Endocrinology, vol. 133: 1753(1993)). It is also known that NPY has central effects, such as depression, anxiety, schizophrenia, pain, dementia, or the like (Drugs, vol. 52: 371(1996)). Further, in the periphery, NPY coexists with norepinephrine in sympathetic nerve ending and is involved in the tonicity of the sympathetic nervous system. It is known that peripheral administration of NPY causes vasoconstriction and enhances the effects of other vasoconstrictive substances such as norepinephrine (British Journal of Pharmacology, vol. 95: 419(1988)). It is also reported that NPY is involved in the enhancement of cardiac hypertrophy as a result of the acceleration of sympathetic nervous system (Proceeding National Academic Science USA, vol. 97: 1595(2000)).

Further, it is reported that NPY is also involved in the secretory function of sexual hormones and growth hormone, sexual and reproductive function, gastrointestinal motility, bronchoconstriction, inflammation and alcohol preference (Life Science, vol. 55: 551(1994); The Journal of Allergy and Immunology, vol. 101: S345(1998); Nature, vol. 396: 366(1998)).

NPY has a variety of pharmacological effects which result from its binding to some receptors to which peptide YY and pancreatic polypeptide, which are similar to NPY, also bind. It is known that these pharmacological effects are caused and mediated by the action of, at least, five receptors with or without synergistic interactions (Trends in Neuroscience, vol. 20: 294(1997)).

It is reported that the central action mediated by NPY Y1 receptor includes the remarkable orexigenic effect(Endocrinology, vol. 137: 3177(1996); Endocrinology, vol. 141: 1011(2000)). Further, it is reported that NPY Y1 receptor is involved in anxiety and pain (Nature, vol. 259: 528(1993); Brain research, vol. 859: 361(2000)). In addition, the pressor effects mediated by the strong action of vasoconstriction in the periphery is also reported. (FEBS Letters, vol. 362: 192(1995); Nature Medicine, vol. 4: 722(1998)).

It is known that actions mediated by NPY Y2 receptor include the inhibitory effect on the release of various neurotransmitters in the nerve endings (British Journal of Pharmacology, vol. 102: 41(1991); Synapse, vol. 2: 299(1988)). In the periphery, NPY causes constriction of blood vessel or vas deferens directly or by controlling these neurotransmitters (The Journal of Pharmacology and Experimental Therapeutics, vol. 261:863(1992); British Journal of Pharmacology, vol. 100: 190(1990)). In addition, inhibition of lipolysis in adipose tissues is known (Endocrinology, vol. 131: 1970 (1992)). Further, the inhibition of ion secretion in the gastro-intestinal tract is reported (British Journal of Pharmacology, vol. 101: 247(1990)).

On the other hand, the effect on the central nervous system functions such as memory and anxiety are also reported (Brain Research, vol. 503: 73(1989); Peptides, vol. 19: 359(1998)).

It is reported that NPY Y3 receptor is expressed mainly in brain stem and in the heart and is related to regulation of blood pressure and heart rate (The Journal of Pharmacology and Experimental Therapeutics, vol. 258: 633(1991); Peptides, vol. 11: 545(1990)). Further, it is known that NPY Y3 receptor is involved in the control of catecholamine secretion in adrenal gland (The Journal of Pharmacology and Experimental Therapeutics, vol. 244: 468(1988); Life Science, vol. 50: PL7 (1992)).

NPY Y4 receptor has a high affinity especially for pancreatic polypeptide and has pharmacological effects on the inhibition of pancreatic exocrine secretion and the gastrointestinal motility (Gastroenterology, vol. 85: 1411(1983)). Further, it is reported that NPY enhances the secretion of the sexual hormone in the central nervous system (Endocrinology, vol. 140: 5171 (1999)).

The effects mediated by NPY Y5 receptor include the remarkable fat accumulating action including the orexigenic effect (Nature, vol. 382: 168(1996)); American Journal of Physiology, vol. 277: R1428 (1999)). It is reported that the NPY Y5 receptor also mediates the central nervous system effects, such as seizure and epilepsy, or pain and the morphine withdrawal symptoms (Nature Medicine, vol. 3: 761 (1997); Proceeding National Academic Science USA, vol. 96: 13518(1999)); The Journal of Pharmacology and Experimental Therapeutics, vol. 284: 633(1998)). It is reported that in the periphery, NPY Y5 receptor is involved in diuretic action and hypoglycemic effect (British Journal of Pharmacology, vol. 120: 1335(1998); Endocrinology, vol. 139: 3018(1998)). It is also reported that NPY enhances cardiac hypertrophy as a result of the acceleration of sympathetic nervous system (Proceeding National Academic Science USA, vol. 97: 1595(2000)).

The function of NPY is caused by binding to the NPY receptors existing in the central or peripheral nervous system. Therefore, expression of the effect of NPY can be curbed by blocking the binding of NPY to NPY receptors. Substances which antagonize NPY binding to NPY receptors may be useful for the prophylaxis or treatment of various diseases which NPY relates to, such as cardiovascular disorders exemplified by hypertension, nephropathy, heart diseases and vasospasm, central nervous system disorders exemplified by bulimia, depression, anxiety, convulsion, epilepsy, dementia, pain, alcoholism and drug withdrawal, metabolic diseases exemplified by obesity, diabetes and hormone abnormality, sexual and reproductive dysfunction, gastro-intestinal motility disorder, respiratory disorder, inflammation or glaucoma, or the like (Trends in Pharmacological Science, 15: 153(1994); Life Science, 55: 551 (1994); Drugs, vol. 52: 371(1996); The Journal of Allergy and Immunology, vol. 101: S345(1998); Nature, vol. 396: 366(1998); The Journal of Pharmacology and Experimental Therapeutics, vol. 284: 633(1998); Trends in Pharmacological Science, vol. 20: 104(1999); Proceeding National Academic Science USA, vol. 97: 1595(2000)).

Recently, the investigation of the present inventors has revealed that some kind of NPY receptor antagonist is useful in the prophylaxis or treatment of hypercholesterolemia, hyperlipidemia and arteriosclerosis (International application publication WO99/27965).

Imidazolone derivatives are disclosed in International application publication WO99/48888 and these compounds are described to have NPY receptor antagonistic activities. However, the compounds of the present invention are neither disclosed nor suggested.

2,4,4-triphenyl-2-imidazoline is described in CA 52:17240f of Chemical Abstracts, however, NPY receptor antagonistic activities of the compound are neither disclosed nor suggested.

DISCLOSURE OF INVENTION

The object of the present invention is to provide novel medicines having NPY antagonistic activities.

The present inventors have discovered that the compounds represented by the general formula (I):

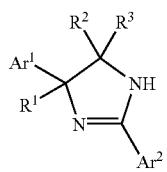

(1)

wherein $Ar^1$, $Ar^2$ and $Ar^3$ represent independently aryl or heteroaryl which may be substituted, the substituent being selected from the group consisting of cyano, halogen atom, nitro, lower alkyl, halo(lower)alkyl, hydroxy(lower)alkyl, cyclo(lower)alkyl(lower)alkyl, lower alkenyl, lower alkylamino, di-lower alkylamino, lower alkanoylamino, lower alkylsulfonylamino, arylsulfonylamino, hydroxy, lower alkoxy, halo(lower)alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl;

n represents 0, 1 or 2;

$R^1$ represents cyclo(lower)alkyl or a group represented by the formula of —$Ar^3$;

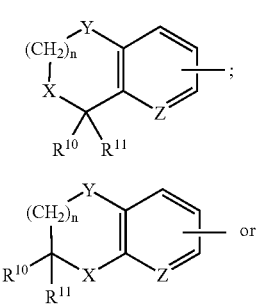

(a)

(b)

(c)

$R^2$ and $R^3$ represent independently hydrogen atom, cyclo(lower)alkyl, lower alkenyl or lower alkyl which may be substituted, the substituent being selected from the group consisting of halogen atom, lower alkylamino, di-lower alkylamino, lower alkanoylamino, hydroxy, lower alkoxy, formyl, lower alkoxycarbonyl, lower alkylcarbamoyl and di-lower alkylcarbamoyl;

both $R^{10}$ and $R^{11}$ represent hydrogen atom or they combine to represent oxo;

$R^{12}$ represents hydrogen atom or lower alkyl;

X and Y represent independently methylene, ethenylene, a group represented by the formula of —$NR^{12}$—, oxygen atom or sulfur atom;

Z represents methine or nitrogen atom (however, in case both $R^2$ and $R^3$ represent hydrogen atom, $Ar^1$, $Ar^2$ and $R^1$ do not represent simultaneously an unsubstituted phenyl group; exhibit NPY antagonistic activities and are excellent in pharmacokinetics such as penetration to brain and cerebrospinal fluid, and have completed the present invention.

The compounds of the present invention (I) are useful as agents for the treatment of various diseases which NPY relates to, that is, for example, cardiovascular disorders exemplified by hypertension, nephropathy, heart diseases, vasospasm and arteriosclerosis, central nervous system disorders exemplified by bulimia, depression, anxiety, convulsion, epilepsy, dementia, pain, alcoholism and drug withdrawal, metabolic diseases exemplified by obesity, diabetes, hormone abnormality, hypercholesterolemia and hyperlipidemia, sexual and reproductive dysfunction, gastro-intestinal disorder such as the inhibition of gastro-intestinal motility, respiratory disorder, inflammation, or glaucoma, or the like since they exhibit NPY antagonistic activities and are excellent in internal kinetics such as intracerebral transition or transition to cerebrospinal fluid.

More particularly, the compounds of the present invention (I) are useful as agents for the treatment of bulimia, obesity, diabetes, or the like.

The present invention relates to the compounds represented by the general formula (I), the salts or esters thereof, and the process for production as well as the use thereof.

Further, the present invention relates to the intermediates for producing the compounds represented by the general formula (I). That is, the present invention relates to the compounds represented by the general formula (II'):

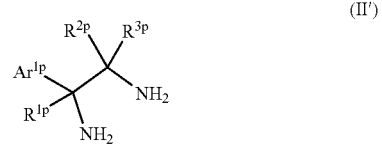

(II')

wherein $Ar^{1p}$ and $Ar^{3p}$ represent independently aryl or heteroaryl which may be substituted, the substituent being selected from the group consisting of cyano, halogen atom, nitro, lower alkyl, halo(lower)alkyl, cyclo(lower)alkyl(lower)alkyl, lower alkenyl, di-lower alkylamino, lower alkoxy, halo(lower)alkoxy, aryloxy, heteroaryloxy, lower alkylthio, formyl, lower alkanoyl, lower alkoxycarbonyl, di-lower alkylcarbamoyl, lower alkylsulfonyl, arylsulfonyl, aryl, heteroaryl and an optionally protected, hydroxy(lower)alkyl, lower alkylamino, lower alkanoylamino, lower alkylsulfonylamino, arylsulfonylamino, hydroxy, carboxyl, carbamoyl, or lower alkylcarbamoyl group;

n represents 0, 1 or 2;

$R^{1p}$ represents cyclo(lower)alkyl or a group represented by the formula of $-Ar^{3p}$;

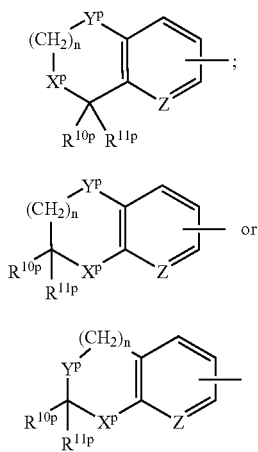

(a$_p$)

(b$_p$)

(c$_p$)

$R^{2p}$ and $R^{3p}$ represent independently hydrogen atom, cyclo (lower)alkyl, lower alkenyl or lower alkyl which may be substituted, the substituent being selected from the group consisting of halogen atom, di-lower alkylamino, lower alkoxy, formyl, lower alkoxycarbonyl, di-lower alkylcarbamoyl and an optionally protected, lower alkylamino, lower alkanoylamino, hydroxy or lower alkylcarbamoyl group;

both $R^{10p}$ and $R^{11p}$ represent hydrogen atom or they combine to represent an optionally protected oxo group;

$R^{12p}$ represents hydrogen atom, lower alkyl, or a protecting group for imino group;

$X^p$ and $Y^p$ represent independently methylene, ethenylene, a group represented by the formula of $-NR^{12p}-$, oxygen atom or sulfur atom;

Z represents methine or nitrogen atom (however, (a) in case both $R^{2p}$ and $R^{3p}$ represent hydrogen atom, $Ar^{1p}$ and $R^{1p}$ do not represent simultaneously an unsubstituted phenyl group and (b) in case $R^{2p}$ is hydrogen atom and $R^{3p}$ is methyl, isopropyl, isobutyl, or tert-butyl, $Ar^{1p}$ and $R^{1p}$ do not represent simultaneously 4-methoxyphenyl).

The means of terms used in the present specification are defined and more detailed description of this invention is shown in the following.

"Halogen atom" means fluorine atom, chlorine atom, bromine atom or iodine atom.

"Lower alkyl" means a straight- or branched-chain alkyl group of C1 to C6 and includes, for example, methyl, ethyl, propyl, isopropyl, butyl, isobutyl, sec-butyl, tert-butyl, pentyl, isopentyl, hexyl, isohexyl, or the like.

"Halo(lower)alkyl" means the aforesaid lower alkyl substituted with 1 or not less than 2, preferably 1 to 3 aforesaid halogen atoms identically or differently at the substitutable, arbitrary positions, and includes, for example, fluoromethyl, difluoromethyl, trifluoromethyl, 2-fluoroethyl, 1,2-difluoroethyl, chloromethyl, 2-chloroethyl, 1,2-dichloroethyl, bromomethyl, iodomethyl, or the like.

"Hydroxy(lower)alkyl" means the aforesaid lower alkyl substituted with 1 or not less than 2, preferably 1 or 2 hydroxy groups at the substitutable, arbitrary positions and includes, for example, hydroxymethyl, 2-hydroxyethyl, 1-hydroxy-1-methylethyl, 1,2-dihydroxyethyl, 3-hydroxypropyl, or the like.

"Cyclo(lower)alkyl" means a cycloalkyl group of C3 to C6 and includes cyclopropyl, cyclobutyl, cyclopentyl and cyclohexyl.

"Cyclo(lower)alkyl(lower)alkyl" means the aforesaid lower alkyl substituted with 1 or not less than 2 cyclo(lower) alkyl groups, preferably 1 aforesaid cyclo(lower)alkyl group at the substitutable, arbitrary positions and includes, for example, cyclopropylmethyl, 2-cyclopropylethyl, 3-cyclopropylpropyl, cyclobutylmethyl, 2-cyclobutylethyl, 3-cyclobutylpropyl, cyclopentylmethyl, 2-cyclopentylethyl, 3-cyclopentylpropyl, cyclohexylmethyl, 2-cyclohexylethyl, 3-cyclohexylpropyl, or the like.

"Lower alkenyl" means a straight- or branched-chain alkenyl group of C2 to C6 and includes, for example, vinyl, 1-propenyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl, 4-pentenyl, or the like.

"Lower alkylamino" means an amino group mono-substituted with the aforesaid lower alkyl group and includes, for example, methylamino, ethylamino, propylamino, isopropylamino, butylamino, sec-butylamino, tert-butylamino, or the like.

"Di-lower alkylamino" refers to an amino group di-substituted with identical or different aforesaid lower alkyl and includes, for example, dimethylamino, diethylamino, ethylmethylamino, dipropylamino, methylpropylamino, diisopropylamino, or the like.

"Lower alkanoyl" means an alkanoyl group containing the aforesaid lower alkyl, that is, an alkanoyl group of C2 to C7 and includes, for example, acetyl, propionyl, butyryl, isobutyryl, valeryl, isovaleryl, pivaloyl, or the like.

"Lower alkanoyl amino" means an amino group mono-substituted with the aforesaid lower alkanoyl and includes, for example, acetylamino, propionylamino, butyrylamino, isobutyrylamino, valerylamino, isovalerylamino, pivaloylamino, or the like.

"Lower alkylsulfonyl" means a alkylsulfonyl group containing the aforesaid lower alkyl and includes, for example, methylsulfonyl, ethylsulfonyl, propylsulfonyl, isopropylsulfonyl, butylsulfonyl, sec-butylsulfonyl, tert-butylsulfonyl, or the like.

"Lower alkylsulfonylamino" means an amino group mono-substituted with the aforesaid lower alkylsulfonyl and includes, for example, methylsulfonylamino, ethylsulfonylamino, propylsulfonylamino, isopropylsulfonylamino, butylsulfonylamino, sec-butylsulfonylamino, tert-butylsulfonylamino, or the like.

"Aryl" includes, for example, phenyl, naphthyl or the like.

"Arylsulfonyl" means an arylsulfonyl group containing the aforesaid aryl and include, for example, phenylsulfonyl, 1-naphthylsulfonyl, 2-naphthylsulfonyl, or the like.

"Arylsulfonylamino" means an amino group mono-substituted with the aforesaid arylsulfonyl and includes, for example, phenylsulfonylamino, 1-naphthylsulfonylamino, 2-naphthylsulfonylamino, or the like.

"Lower alkoxy" means a straight- or branched-chain alkoxy group of C1 to C6 and include, for example, methoxy, ethoxy, propoxy, isopropoxy, butoxy, sec-butoxy, isobutoxy, tert-butoxy, pentyloxy, isopentyloxy, hexyloxy, isohexyloxy, or the like.

"Halo(lower)alkoxy" refers to the aforesaid lower alkoxy substituted with 1 or not less than 2, preferably 1 to 3 aforesaid halogen atoms identically or differently at the substitutable, arbitrary positions and includes, for example, fluoromethoxy, difluoromethoxy, trifluoromethoxy, 2-fluoroethoxy, 1,2-difluoroethoxy, chloromethoxy, 2-chloroethoxy, 1,2-dichloroethoxy, bromomethoxy, iodomethoxy, or the like.

"Aryloxy" means an aryloxy group containing the aforesaid aryl and includes, for example, phenoxy, 1-naphtoxy, 2-naphtoxy, or the like.

"Lower alkylthio" means a straight- or branched-chain alkylthio group of C1 to C6 and includes, for example, methylthio, ethylthio, propylthio, isopropylthio, butylthio, sec-butylthio, isobutylthio, tert-butylthio, pentylthio, isopentylthio, hexylthio, isohexylthio, or the like.

"Lower alkoxycarbonyl" means an alkoxycarbonyl group containing the aforesaid lower alkoxy group, that is, an alkoxycarbonyl group of C2 to C7 and includes, for example, methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, or the like.

"Lower alkylcarbamoyl" refers to a carbamoyl group mono-substituted with the aforesaid lower alkyl and includes, for example, methylcarbamoyl, ethylcarbamoyl, propylcarbamoyl, isopropylcarbamoyl, butylcarbamoyl, sec-butylcarbamoyl, tert-butylcarbamoyl, or the like.

"Di-lower alkylcarbamoyl" means a carbamoyl group di-substituted with the aforesaid lower alkyl and includes, for example, dimethylcarbamoyl, diethylcarbamoyl, ethylmethylcarbamoyl, dipropylcarbamoyl, methylpropylcarbamoyl, diisopropylcarbamoyl, or the like.

"Heteroaryl" means a 5- or 6-membered monocyclic heteroaromatic group which contains 1 or not less than 2, preferably 1 to 3 hetero atoms identically or differently selected from the group of oxygen atom, nitrogen atom and sulfur atom, or "Heteroaryl" means a condensed cyclic heteroaromatic group, where the aforesaid monocyclic heteroaromatic group is condensed with the aforesaid aryl group, or the identical or different aforesaid monocyclic heteroaromatic group are condensed each other and includes, for example, pyrrolyl, furyl, thienyl, imidazolyl, pyrazolyl, thiazolyl, isothiazolyl, oxazolyl, isoxazolyl, triazolyl, tetrazolyl, oxadiazolyl, 1,2,3-thiadiazolyl, 1,2,4-thiadiazolyl, 1,2,5-thiadiazolyl 1,3,4-thiadiazolyl, pyridyl, pyrazinyl, pyrimidinyl, pyridazinyl, 1,2,4-triazinyl, 1,3,5-triazinyl, indolyl, benzofuranyl, benzothienyl, benzimidazolyl, benzoxazolyl, benzisoxazolyl, benzothiazolyl, benzisothiazolyl, indazolyl, purinyl, quinolyl, isoquinolyl, phthalazinyl, naphthyridinyl, quinoxalinyl, quinazolinyl, cinnolinyl, pteridinyl, 1,5-naththyridinyl, or the like.

"Heteroaryloxy" means a heteroaryloxy group which contains the aforesaid heteroaryl group and includes, for example, 2-thienyloxy, 3-thienyloxy, 2-pyridyloxy, 3-pyridyloxy, 4-pyridyloxy, 3-indolyloxy, 4-indolyloxy, 5-indolyloxy, 6-indolyloxy, and the like.

The salts of compounds represented by the general formula (I) means the pharmaceutically acceptable and common salts and include, for example, base addition salt to carboxyl group when the compound has a carboxyl group, or acid addition salt to amino or basic heterocyclyl when the compound has an amino or a basic heterocyclyl group.

The aforesaid base addition salts include salts with alkali metals (for example, sodium, potassium, etc.); alkaline earth metals (for example, calcium, magnesium, etc.); ammonium; organic amines (for example trimethylamine, triethylamine, dicyclohexylamine, ethanolamine, diethanolamine, triethanolamine, procaine, N,N'-dibenzylethylenediamine, etc.); or the like.

The aforesaid acid addition salts include salts with inorganic acids (for example, hydrochloric acid, sulfuric acid, nitric acid, phosphoric acid, perchloric acid, etc.); organic acids (for example, maleic acid, fumaric acid, tartaric acid, citric acid, ascorbic acid, trifluoroacetic acid, etc.); sulfonic acids (for example, methanesulfonic acid, isethionic acid, benzenesulfonic acid, p-toluenesulfonic acid, etc.); or the like.

The esters of the compounds represented by the general formula (I) refer to, for example, the pharmaceutically acceptable, common esters on the carboxyl group when the compound has a carboxyl group and include, for example, esters with lower alkyls (for example, methyl, ethyl, propyl, isopropyl, butyl, sec-butyl, tert-butyl, pentyl, isopentyl, neopentyl, cyclopropyl, cyclobutyl, cyclopentyl, etc.), aralkyls (for example, benzyl, phenethyl, etc.), lower alkenyls (for example, allyl, 2-butenyl, etc.), lower alkoxy(lower)alkyls (for example, methoxymethyl, 2-methoxyethyl, 2-ethoxyethyl, etc.), lower alkanoyloxy(lower)alkyls (for example, acetoxymethyl, pivaloyloxymethyl, 1-pivaloyloxyethyl, etc.), lower alokoxycarbonyl(lower)alkyls (for example, methoxycarbonylmethyl, isopropoxycarbonylmethyl, etc.), carboxy(lower)alkyls (for example, carboxymethyl, etc.), lower alkoxycarbonyloxy(lower)alkyls (for example, 1-(ethoxycarbonyloxy)ethyl, 1-(cyclohexyloxycarbonyloxy)ethyl, etc.), carbamoyloxy(lower)alkyls (for example, carbamoyloxymethyl, etc.), phthalidyl, (5-substituted-2-oxo-1,3-dioxol-4-yl) methyl (for example, (5-methyl-2-oxo-1,3-dioxol-4-yl)methyl, etc.), or the like.

"An agent for treatment" means a medicament which is employed for the treatment and/or prophylaxis of various diseases.

In order to disclose the aforesaid compounds represented by the general formula (I), the various symbols used in the formula (I) are explained in more detail by the use of preferred embodiments.

$Ar^1$, $Ar^2$ and $Ar^3$ represent independently aryl or heteroaryl which may be substituted, the substituent being selected from the group consisting of cyano, halogen atom, nitro, lower alkyl, halo(lower)alkyl, hydroxy(lower)alkyl, cyclo(lower)alkyl(lower)alkyl, lower alkenyl, lower alkylamino, di-lower alkylamino, lower alkanoylamino, lower alkylsulfonylamino, arylsulfonylamino, hydroxy, lower alkoxy, halo(lower)alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl.

The expression "$Ar^1$, $Ar^2$ and $Ar^3$ represent independently aryl or heteroaryl which may be substituted, the substituent being selected from the group consisting of cyano, halogen atom, nitro, lower alkyl, halo(lower)alkyl, hydroxy(lower)alkyl, cyclo(lower)alkyl(lower)alkyl, lower alkenyl, lower alkylamino, di-lower alkylamino, lower alkanoylamino, lower alkylsulfonylamino, arylsulfonylamino, hydroxy, lower alkoxy, halo(lower)alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl" refers to the unsubstituted aforesaid aryl or the unsubstituted aforesaid heteroaryl, or the aforesaid aryl or the aforesaid heteroaryl which has substituent(s) at the substitutable, arbitrary position(s). The aforesaid substituent can be, identically or differently, 1 or not less than 2 substituents, preferably 1 or 2 substituents selected from the group consisting of cyano, halogen atom, nitro, lower alkyl, halo(lower)alkyl, hydroxy(lower)alkyl, cyclo(lower)alkyl (lower)alkyl, lower alkenyl, lower alkylamino, di-lower alkylamino, lower alkanoylamino, lower alkylsulfonylamino, arylsulfonylamino, hydroxy, lower alkoxy, halo (lower)alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl.

Halogen atom as the aforesaid substituent preferably includes, for example, fluorine atom, chlorine atom, bromine atom, or the like.

Lower alkyl as the aforesaid substituent preferably includes, for example, methyl, ethyl, propyl, isopropyl, or the like.

Halo(lower)alkyl as the aforesaid substituent preferably includes, for example, difluoromethyl, trifluoromethyl, or the like.

Hydroxy(lower)alkyl as the aforesaid substituent preferably includes, for example, hydroxymethyl, 2-hydroxyethyl, 1-hydroxy-1-methylethyl, or the like.

Cyclo(lower)alkyl(lower)alkyl as the aforesaid substituent preferably includes, for example, cyclopropylmethyl, cyclobutylmethyl, cyclopentylmethyl, or the like.

Lower alkenyl as the aforesaid substituent preferably includes, for example, vinyl, 1-propenyl, 2-methyl-1-propenyl, or the like.

Lower alkylamino as the aforesaid substituent preferably includes, for example, methylamino, ethylamino, or the like.

Di-lower alkylamino as the aforesaid substituent preferably includes, for example, dimethylamino, diethylamino, or the like.

Lower alkanoyl amino as the aforesaid substituent preferably includes, for example, acetylamino, propionylamino, or the like.

Lower alkylsulfonylamino as the aforesaid substituent preferably includes, for example, methylsulfonylamino, ethylsulfonylamino, or the like.

Arylsulfonylamino as the aforesaid substituent preferably includes, for example, phenylsulfonylamino, or the like.

Lower alkoxy as the aforesaid substituent preferably includes, for example, methoxy, ethoxy, or the like.

Halo(lower)alkoxy as the aforesaid substituent preferably includes, for example, fluoromethoxy, difluoromethoxy, trifluoromethoxy, or the like.

Aryloxy as the aforesaid substituent preferably includes, for example, phenoxy, or the like.

Heteroaryloxy as the aforesaid substituent preferably includes, for example, 2-pyridyloxy, 3-pyridyloxy, 4-pyridyloxy, or the like.

Lower alkylthio as the aforesaid substituent preferably includes, for example, methylthio, ethylthio, or the like.

Lower alkanoyl as the aforesaid substituent preferably includes, for example, formyl, acetyl, propionyl, or the like.

Lower alkoxycarbonyl as the aforesaid substituent preferably includes, for example, methoxycarbonyl, ethoxycarbonyl, or the like.

Lower alkylcarbamoyl as the aforesaid substituent preferably includes, for example, methylcarbamoyl, ethylcarbamoyl, or the like.

Di-lower alkylcarbamoyl as the aforesaid substituent preferably includes, for example, dimethylcarbamoyl, diethylcarbamoyl, or the like.

Lower alkylsulfonyl as the aforesaid substituent preferably includes, for example, methylsulfonyl, ethylsulfonyl, or the like.

Arylsulfonyl as the aforesaid substituent preferably includes, for example, phenylsulfonyl, or the like.

Aryl as the aforesaid substituent preferably includes, for example, phenyl, or the like.

Heteroaryl as the aforesaid substituent preferably includes, for example, thienyl, thiazolyl, isothiazolyl, pyridyl, pyrazinyl, or the like.

The substituent(s) of $Ar^1$ include, preferably, for example, halogen atom, lower alkyl, halo(lower)alkyl, hydroxy(lower)alkyl, lower alkoxy, halo(lower)alkoxy, lower alkanoyl or the like, more preferably, halogen atom, halo(lower)alkyl, halo(lower)alkoxy, or the like.

Aryl in $Ar^1$ includes, preferably, for example, phenyl or the like, and heteroaryl in $Ar^1$ includes, preferably, for example, thienyl, pyridyl, or the like.

$Ar^1$ is preferably exemplified by phenyl which has substituent(s) selected from the group consisting of halogen atom, halo(lower)alkyl and halo(lower)alkoxy, or by thienyl or pyridyl which may have substituent(s) selected from the group consisting of halogen atom, halo(lower)alkyl and halo(lower)alkoxy. More concretely, $Ar^1$ is for example, phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-methylphenyl, 3-methylphenyl, 4-methylphenyl, 2-trifluoromethylphenyl, 3-trifluoromethylphenyl, 4-trifluoromethylphenyl, 2-hydroxymethylphenyl, 3-hydroxymethylphenyl, 4-hydroxymethylphenyl, 2-methoxyphenyl, 3-methoxyphenyl, 4-methoxyphenyl, 2-difluoromethoxyphenyl, 3-difluoromethoxyphenyl, 4-difluoromethoxyphenyl, 2-trifluoromethoxyphenyl, 3-trifluoromethoxyphenyl, 4-trifluoromethoxyphenyl, 2-formylphenyl, 3-formylphenyl, 4-formylphenyl, 2-thienyl, 4-chloro-2-thienyl, 5-chloro-2-thienyl 4-bromo-2-thienyl, 5-bromo-2-thienyl, 4-methyl-2-thienyl, 5-methyl-2-thienyl, 4-methoxy-2-thienyl, 5-methoxy-2-thienyl, 3-thienyl, 5-chloro-3-thienyl, 5-methyl-3-thienyl, 5-methoxy-3-thienyl 2-pyridyl, 4-methyl-2-pyridyl, 5-methyl-2-pyridyl, 4-methoxy-2-pyridyl, 5-methoxy-2-pyridyl, 4-chloro-2-pyridyl, 5-chloro-2-pyridyl, 3-pyridyl, 4-methyl-3-pyridyl, 5-methyl-3-pyridyl, 4-methoxy-3-pyridyl, 5-methoxy-3-pyridyl, 6-fluoro-3-pyridyl, 4-chloro-3-pyridyl, 5-chloro-3-pyridyl, 4-pyridyl, 2-fluoro-4-pyridyl, 2-chloro-4-pyridyl, 3-chloro-4-pyridyl, 2-methyl-4-pyridyl, 3-methyl-4-pyridyl, 2-methoxy-4-pyridyl, 3-methoxy-4-pyridyl, and the like, preferably, 2-fluorophenyl, 3-fluorophenyl, 4-fluorophenyl, 2-chlorophenyl, 3-chlorophenyl, 4-chlorophenyl, 3-bromophenyl, 4-bromophenyl, 3-methylphenyl, 3-trifluoromethylphenyl, 4-trifluoromethylphenyl, 3-methoxyphenyl, 4-methoxyphenyl, 3-trifluoromethoxyphenyl, 4-trifluoromethoxyphenyl 3-difluoromethoxyphenyl, 4-difluoromethoxyphenyl, 2-thienyl, 4-chloro-2-thienyl, 5-chloro-2-thienyl, 4-bromo-2-thienyl, 5-bromo-2-thienyl, 3-pyridyl, 4-methoxy-3-pyridyl, 5-methoxy-3-pyridyl, 6-fluoro-3-pyridyl, 4-chloro-3-pyridyl, 5-chloro-3-pyridyl, 2-fluoro-4-pyridyl, and the like, particularly, 4-fluorophenyl, 6-fluoro-3-pyridyl, 2-fluoro-4-pyridyl or the like, more preferably, 4-fluorophenyl, or the like.

The substituent of $Ar^2$ includes, preferably, for example, cyano, halogen atom, nitro, lower alkyl, halo(lower)alkyl, lower alkoxy, halo(lower)alkoxy, formyl, lower alkanoyl, lower alkoxycarbonyl, lower alkylsulfonyl, or the like, more preferably, cyano, or the like.

Aryl in Ar² includes, for example, phenyl or the like, and heteroaryl in Ar² includes, for example, a 5- or 6-membered monocyclic heteroaromatic group containing 1 or not less than 2, preferably 1 to 3 hetero atoms identically or differently selected from the group consisting of oxygen atom, nitrogen atom and sulfur atom, more concretely, for example, thienyl, thiazolyl, isothiazolyl, 1,2,5-thiadiazolyl, pyridyl, pyrazinyl, pyrimidinyl, or the like preferably.

Ar² includes, for example, phenyl which contains substituent(s) selected from the group consisting of cyano, halogen atom, nitro, lower alkyl, halo(lower)alkyl, lower alkoxy, halo(lower)alkoxy, formyl, lower alkanoyl, lower alkoxycarbonyl and lower alkylsulfonyl, or a 5- or 6-membered monocyclic heteroaromatic group containing 1 or not less than 2, preferably 1 to 3 hetero atoms identically or differently selected from the group consisting of oxygen atom, nitrogen atom and sulfur atom, which may have substituent(s) selected from the group consisting of cyano, halogen atom, nitro, lower alkyl, halo(lower)alkyl, lower alkoxy, halo(lower)alkoxy, formyl, lower alkanoyl, lower alkoxycarbonyl and lower alkylsulfonyl. 5- or 6-membered monocyclic heteroaromatic group includes, preferably, thienyl, thiazolyl, isothiazolyl, 1,2,5-thiadiazolyl, pyridyl, pyrimidinyl, pyrazinyl or the like. More concretely, Ar² includes, for example, phenyl, 3-cyanophenyl, 4-cyanophenyl, 3-fluorophenyl, 4-fluorophenyl, 3-chlorophenyl, 4-chlorophenyl, 3-bromophenyl, 4-bromophenyl, 3-nitrophenyl, 4-nitrophenyl, 3-methylphenyl, 4-methylphenyl, 3,5-dimethylphenyl, 3-trifluoromethylphenyl, 4-trifluoromethylphenyl, 3-hydroxymethylphenyl, 4-hydroxymethylphenyl, 3-methoxyphenyl, 4-methoxyphenyl, 3-trifluoromethoxyphenyl, 4-trifluoromethoxyphenyl, 3-formylphenyl, 4-formylphenyl, 3-acetylphenyl, 3-methoxycarbonylphenyl, 4-methoxycarbonylphenyl, 3-methylsulfonylphenyl, 4-methylsulfonylphenyl, 2-thienyl, 4-cyano-2-thienyl, 5-cyano-2-thienyl, 4-chloro-2-thienyl, 5-chloro-2-thienyl, 3-thienyl, 2-thiazolyl, 4-thiazolyl, 5-thiazolyl, 3-isothiazolyl, 4-isothiazolyl, 1,2,5-thiadiazol-3-yl, 2-pyridyl, 4-cyano-2-pyridyl, 6-cyano-2-pyridyl, 4-chloro-2-pyridyl, 6-chloro-2-pyridyl, 4-trifluoromethyl-2-pyridyl, 6-trifluoromethyl-2-pyridyl, 6-hydroxy-2-pyridyl, 4-methoxy-2-pyridyl, 4-methoxycarbonyl-2-pyridyl, 3-pyridyl, 5-cyano-3-pyridyl, 5-bromo-3-pyridyl, 4-pyridyl, 2-cyano-4-pyridyl, 2-chloro-4-pyridyl, pyrazinyl, 2-pyrimidinyl, 4-cyano-2-pyrimidinyl, 4-chloro-2-pyrimidinyl, 4-trifluoromethyl-2-pyrimidinyl, 4-carbamoyl-2-pyrimidinyl, 4-pyrimidinyl, 6-cyano-4-pyrimidinyl, 6-chloro-4-pyrimidinyl, 5-pyrimidinyl, 3-pyridazinyl or the like, preferably, 3-cyanophenyl, 3-fluorophenyl, 3-chlorophenyl, 3-bromophenyl, 3-nitrophenyl, 3-methylphenyl, 3-trifluoromethylphenyl, 3-trifluoromethoxyphenyl, 3-formylphenyl, 3-methylsulfonylphenyl, 5-thiazolyl, 4-isothiazolyl, 1,2,5-thiadiazol-3-yl, 4-cyano-2-pyridyl, 6-cyano-2-pyridyl, 3-pyridyl, 5-cyano-3-pyridyl, 2-cyano-4-pyridyl, 2-chloro-4-pyridyl, pyrazinyl, 4-cyano-2-pyrimidinyl, 6-cyano-4-pyrimidinyl, and the like, more preferably, 3-cyanophenyl, 3-methylsulfonylphenyl, 4-cyano-2-pyridyl, 6-cyano-2-pyridyl, 5-cyano-3-pyridyl, 2-chloro-4-pyridyl, 4-cyano-2-pyrimidinyl, or the like.

The substituent(s) of Ar³ include, preferably, for example, halogen atom, lower alkyl, hydroxy(lower)alkyl, lower alkenyl, di-lower alkylamino, lower alkoxy, halo(lower)alkoxy, lower alkanoyl, aryl, or the like.

Aryl in Ar³ includes, preferably, for example, phenyl, naphthyl, or the like, and heteroaryl in Ar³ includes, preferably, for example, thienyl, pyridyl, quinolyl, 1,5-naphthyridinyl, or the like.

Ar³ is preferably, phenyl, naphthyl, thienyl, pyridyl, quinolyl, 1,5-naphthyridinyl or the like which may have substituent(s) selected from the group consisting of, for example, halogen atom, lower alkyl, hydroxy(lower)alkyl, lower alkenyl, di-lower alkylamino, lower alkoxy, halo(lower)alkoxy, lower alkanoyl, aryl, and the like, more concretely, for example, phenyl, 4-cyanophenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 3,4-dimethylphenyl, 2-trifluoromethylphenyl, 3-trifluoromethylphenyl, 4-trifluoromethylphenyl, 3-hydroxymethylphenyl, 4-hydroxymethylphenyl, 3-vinylphenyl, 4-vinylphenyl, 3-dimethylaminophenyl, 4-dimethylaminophenyl, 2-methoxyphenyl, 3-methoxyphenyl, 4-methoxyphenyl, 2-difluoromethoxyphenyl, 3-difluoromethoxyphenyl, 4-difluoromethoxyphenyl, 2-trifluoromethoxyphenyl, 3-trifluoromethoxyphenyl, 4-trifluoromethoxyphenyl, 3-formylphenyl, 4-formylphenyl, 4-biphenylyl, 1-naphthyl, 2-naphthyl, 2-thienyl, 4-chloro-2-thienyl, 5-chloro-2-thienyl, 4-bromo-2-thienyl, 5-bromo-2-thienyl, 4-methyl-2-thienyl, 5-methyl-2-thienyl, 4-methoxy-2-thienyl, 5-methoxy-2-thienyl, 3-thienyl, 5-chloro-3-thienyl, 5-methyl-3-thienyl, 5-methoxy-3-thienyl, 2-pyridyl, 5-fluoro-2-pyridyl, 4-chloro-2-pyridyl, 5-chloro-2-pyridyl, 4-methyl-2-pyridyl, 5-methyl-2-pyridyl, 4-methoxy-2-pyridyl, 5-methoxy-2-pyridyl, 3-pyridyl, 6-fluoro-3-pyridyl, 4-chloro-3-pyridyl, 5-chloro-3-pyridyl, 6-chloro-3-pyridyl, 4-methyl-3-pyridyl, 5-methyl-3-pyridyl, 4-methoxy-3-pyridyl, 5-methoxy-3-pyridyl, 6-methoxy-3-pyridyl, 6-difluoromethoxy-3-pyridyl, 4-pyridyl, 2-fluoro-4-pyridyl, 2-chloro-4-pyridyl, 3-chloro-4-pyridyl, 2-methyl-4-pyridyl, 3-methyl-4-pyridyl, 2-methoxy-4-pyridyl, 3-methoxy-4-pyridyl, 3-quinolyl, 6-quinolyl, 1,5-naphthyridin-3-yl, and the like, preferably, phenyl, 3-fluorophenyl, 4-fluorophenyl, 3-chlorophenyl, 4-chlorophenyl, 2-methylphenyl, 4-methylphenyl, 3,4-dimethylphenyl, 3-trifluoromethylphenyl, 4-trifluoromethylphenyl, 3-vinylphenyl, 4-vinylphenyl, 4-dimethylaminophenyl, 2-methoxyphenyl, 3-methoxyphenyl, 4-methoxyphenyl, 3-difluoromethoxyphenyl, 4-difluoromethoxyphenyl, 3-trifluoromethoxyphenyl, 4-trifluoromethoxyphenyl, 4-formylphenyl, 4-biphenylyl, 2-naphthyl, 2-thienyl, 5-chloro-2-thienyl, 5-methyl-2-thienyl, 5-methoxy-2-thienyl, 2-pyridyl, 5-fluoro-2-pyridyl, 3-pyridyl, 6-fluoro-3-pyridyl, 6-chloro-3-pyridyl, 6-methoxy-3-pyridyl, 6-difluoromethoxy-3-pyridyl, 4-pyridyl, 2-fluoro-4-pyridyl, 3-quinolyl, 6-quinolyl, 1,5-naphthyridin-3-yl, and the like, particularly, 6-fluoro-3-pyridyl, 2-fluoro-4-pyridyl, and the like, more preferably, 6-fluoro-3-pyridyl, or the like.

R¹ represents cyclo(lower)alkyl or a group represented by the formula of —Ar³;

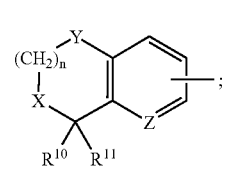

(a)

-continued

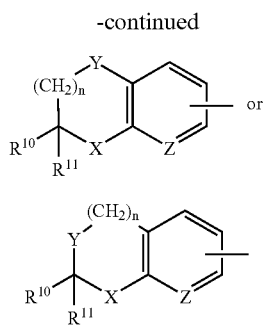

(b)

(c)

Cyclo(lower)alkyl in $R^1$ includes, for example, cyclobutyl, cyclopentyl or cyclohexyl, or the like preferably.

The definition and preferred examples of $Ar^3$ are aforesaid.

In the group represented by the formula of (a), (b) or (c), n means 0, 1 or 2; both $R^{10}$ and $R^{11}$ represent hydrogen atom or they combine to represent oxo; X and Y represent independently methylene, ethenylene, a group represented by the formula of —$NR^{12}$—, oxygen atom or sulfur atom; Z represents methine or nitrogen atom; and $R^{12}$ represents hydrogen atom or lower alkyl.

With regards to the group represented by the formula of (a), (b) or (c), it is preferred that n represents 0 or 1; both $R^{10}$ and $R^{11}$ combine to represent oxo; X and Y represent independently methylene, ethenylene, the group represented by the formula of —$NR^{12}$— or oxygen atom; Z represents methane; and $R^{12}$ represents hydrogen atom. That is, a group represented by the formula of ($a_0$) or ($b_0$) when n is 0, or the like is preferable.

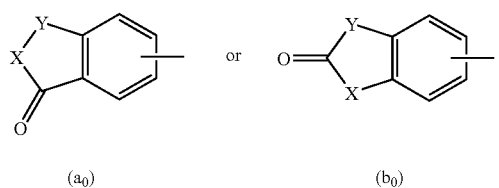

($a_0$) ($b_0$)

And a group represented by the formula of ($a_1$), ($b_1$) or ($c_1$) when n is 1, or the like is preferable.

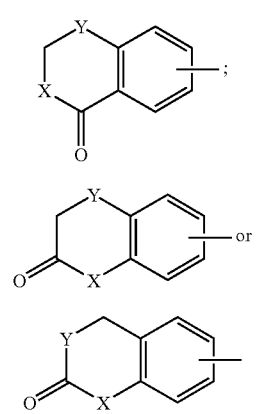

($a_1$)

($b_1$)

($c_1$)

Further, in case n is 0, it is preferred that the combination of X and Y is, for example, oxygen atom and methylene, oxygen atom and ethenylene, oxygen atom and imino, or the like. In case n is 1, it is preferred that the combination of X and Y is, for example, imino and oxygen atom, oxygen atom and oxygen atom, and the like.

Therefore, more concretely, with regards to a group represented by the formula of (a), (b) or (c), a group represented by the formula of (aa), or the like is preferable.

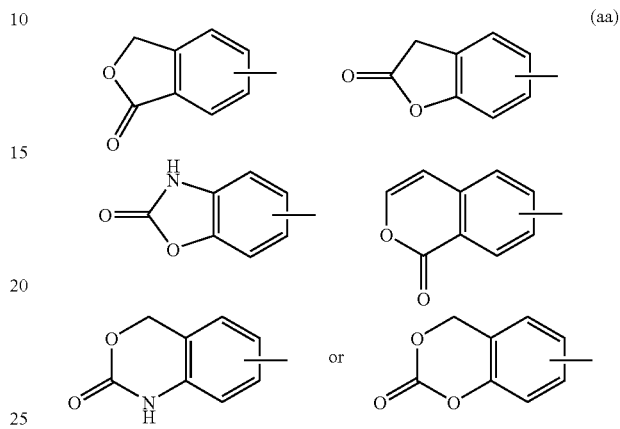

(aa)

With regard to $R^1$, a group represented by the formula of —$Ar^3$ is preferable.

$R^2$ and $R^3$ represent independently hydrogen atom, cyclo(lower)alkyl, lower alkenyl or lower alkyl which may be substituted, the substituent being selected from the group consisting of halogen atom, lower alkylamino, di-lower alkylamino, lower alkanoylamino, hydroxy, lower alkoxy, formyl, lower alkoxycarbonyl, lower alkylcarbamoyl and di-lower alkylcarbamoyl.

Cyclo(lower)alkyl represented by $R^2$ or $R^3$ includes, for example, cyclopentyl, cyclohexyl, or the like preferably.

Lower alkenyl represented by $R^2$ or $R^3$ includes, for example, vinyl, 1-propenyl, 2-propenyl, or the like preferably.

"Lower alkyl which may be substituted, the substituent being selected from the group consisting of halogen atom, lower alkylamino, di-lower alkylamino, lower alkanoylamino, hydroxy, lower alkoxy, formyl, lower alkoxycarbonyl, lower alkylcarbamoyl and di-lower alkylcarbamoyl" represents the unsubstituted aforesaid lower alkyl or the aforesaid lower alkyl containing 1 or not less than 2, preferably 1 or 2 substituents at the substitutable, arbitrary position(s) identically or differently, the substituent being selected from the group consisting of halogen atom, lower alkylamino, di-lower alkylamino, lower alkanoylamino, hydroxy, lower alkoxy, formyl, lower alkoxycarbonyl, lower alkylcarbamoyl and di-lower alkylcarbamoyl.

With regard to halogen atom as the substituent, for example, fluorine atom, and the like are preferred.

With regard to lower alkylamino as the substituent, for example, methylamino, ethylamino, and the like are preferred.

With regard to di-lower alkylamino as the substituent, for example, dimethylamino, diethylamino, and the like are preferred.

With regard to lower alkanoyl amino as the substituent, for example, acetylamino, propionylamino, and the like are preferred.

With regard to lower alkoxy as the substituent, for example, methoxy, ethoxy, and the like are preferred.

With regards to lower alkoxycarbonyl as the substituent, for example, methoxycarbonyl, ethoxycarbonyl, and the like are preferred.

With regard to lower alkylcarbamoyl as the substituent, for example, methylcarbamoyl, ethylcarbamoyl, and the like are preferred.

With regard to di-lower alkylcarbamoyl as the substituent, for example, dimethylcarbamoyl, diethylcarbamoyl, and the like are preferred.

With regard to the substituent of lower alkyl in $R^2$ or $R^3$, for example, halogen atom, lower alkylamino, di-lower alkylamino, hydroxyl, lower alkoxy, and the like are preferred.

With regards to lower alkyl in $R^2$ or $R^3$, for example, methyl, ethyl, propyl, isopropyl, isobutyl, and the like are preferred, and methyl, and the like are more preferred.

More concretely, lower alkyl which may have the aforesaid substituent(s) and which is represented by $R^2$ or $R^3$ includes, for example, methyl, ethyl, propyl, isopropyl, isobutyl, 2-fluoroethyl, 2,2-difluoroethyl, 2,2,2-trifluoroethyl, methylaminomethyl, 2-methylaminoethyl, dimethylaminomethyl, 2-dimethylaminoethyl, 2-diethylaminoethyl, (acetylamino)methyl, hydroxymethyl, 2-hydroxyethyl, 3-hydroxypropyl, methoxymethyl, 2-methoxyethyl, formylmethyl, methoxycarbonylmethyl, ethoxycarbonylmethyl, (methylcarbamoyl)methyl, (ethylcarbamoyl)methyl, (dimethylcarbamoyl)methyl, (diethylcarbamoyl)methyl, and the like, particularly, methyl, ethyl, propyl, hydroxymethyl, and the like, more preferably, methyl, and the like.

With regard to $R^2$ and $R^3$, it is preferred when both are hydrogen atom; or either of them is hydrogen atom and the other is lower alkyl which may have the aforesaid substituent(s).

The compounds of the present invention include preferably, for example, (a) compounds, wherein $R^1$ is the group represented by the formula of —$Ar^3$, and $Ar^2$ is phenyl containing substituent (s) selected from the group consisting of cyano, halogen atom, nitro, lower alkyl, halo(lower)alkyl, lower alkoxy, halo(lower)alkoxy, formyl, lower alkanoyl, lower alkoxycarbonyl and lower alkylsulfonyl; or $R^1$ is a group represented by the formula of —$Ar^3$, and $Ar^2$ is a 5- or 6-membered monocyclic heteroaromatic group which may have substituent(s) selected from the group consisting of cyano, halogen atom, nitro, lower alkyl, halo(lower)alkyl, lower alkoxy, halo(lower)alkoxy, formyl, lower alkanoyl, lower alkoxycarbonyl and lower alkylsulfonyl, the 5- or 6-membered monocyclic heteroaromatic group containing 1 or not less than 2, preferably 1 to 3 hetero atoms identically or differently selected from the group consisting of oxygen atom, nitrogen atom and sulfur atom. The 5- or 6-membered monocyclic heteroaromatic group is more preferably, thienyl, thiazolyl, isothiazolyl, 1,2,5-thiadiazolyl, pyridyl, pyrimidinyl, pyrazinyl; or the like.

The aforesaid (a) compounds include preferably (b) compounds, wherein $Ar^1$ is phenyl containing the substituent(s) selected from the group consisting of halogen atom, halo (lower)alkyl and halo(lower)alkoxy or $Ar^1$ is thienyl or pyridyl which may have substituent(s) selected from the group consisting of halogen atom, halo(lower)alkyl and halo(lower)alkoxy, and the like and include more preferably, (c) compounds, wherein both $R^2$ and $R^3$ are hydrogen; or either $R^2$ or $R^3$ is hydrogen atom and the other is lower alkyl which may have substituent(s) selected from the group consisting of halogen atom, lower alkylamino, di-lower alkylamino, lower alkanoylamino, hydoroxy, lower alkoxy, formyl, lower alkoxycarbonyl, lower alkylcarbamoyl and di-lower alkylcarbamoyl, and the like.

The aforesaid (c) compounds include more preferably, (d) compounds, wherein $Ar^3$ is phenyl, naphthyl, thienyl, pyridyl, quinolyl or 1,5-napththyridinyl, which may have substituent (s) selected from the group consisting of halogen atom, lower alkyl, hydroxy(lower)alkyl, lower alkenyl, di-lower alkylamino, lower alkoxy, halo(lower)alkoxy, lower alkanoyl and aryl.

Further, the aforesaid (a) compounds preferably include (e) compounds, respectively, wherein $Ar^1$ is 4-fluorophenyl, 6-fluoro-3-pyridyl or 2-fluoro-4-pyridyl, $Ar^3$ is 6-fluoro-3-pyridyl or 2-fluoro-4-pyridyl, and either $R^2$ or $R^3$ is hydrogen atom and the other is methyl, and more preferably, particularly, the compounds, wherein $Ar^1$ is 4-fluorophenyl, and $Ar^3$ is 6-fluoro-3-pyridyl; $Ar^1$ is 4-fluorophenyl, and $Ar^3$ is 2-fluoro-4-pyridyl; both $Ar^1$ and $Ar^3$ are 6-fluoro-3-pyridyl; or both $Ar^1$ and $Ar^3$ are 2-fluoro-4-pyridyl; or the like.

However, the compounds, wherein both $R^2$ and $R^3$ are hydrogen atom simultaneously, and $Ar^1$, $Ar^2$ and $R^1$ are unsubstituted phenyl simultaneously, are deleted from the present invention.

The compounds of the present invention may include stereoisomers such as optical isomers, diastereoisomers and geometrical isomers, or tautomers depending upon the mode of substituents. Thus, the compounds of the present invention includes all the stereoisomers, tautomers and a mixture thereof.

Also the polymorphs, hydrates and solvates of the compounds of the present invention are included within the scope of the invention.

The present invention includes prodrugs of the compounds of the present invention within its scope. In general, such prodrugs will be functional derivatives of the compounds of the present invention which are readily convertible in vivo into the compounds which are required in vivo or for the living body. Thus, in the treatment methods of various diseases related to the present invention, the term "administering" shall encompass administering of a compound which may not be specifically disclosed, but which converts to the specifically disclosed compound in vivo after administration to the patient, in addition to administering of the compound specifically disclosed. Conventional procedures for the selection and preparation of suitable prodrug derivatives are described, for example, in "Design of Prodrugs" ed. H. Bundgaard, Elsevier, 1985 or the like which is incorporated by reference herein in its entirety. Metabolites of these compounds include the active compounds produced upon introduction of the compounds of the present invention into biological milieu and belong to the category of the present invention.

The specific example of the compound represented by the general formula (I) is, for example, 2-(3-cyanophenyl)-4,4-bis(4-fluorophenyl)-2-imidazoline,
4,4-bis(4-fluorophenyl)-2-pyradinyl-2-imidazoline,
2-(3-cyanophenyl)-4-(4-fluorophenyl)-4-(1,5-naphthyridin-3-yl)-2-imidazoline,
2-(3-cyanophenyl)-4,4-bis(4-fluorophenyl)-5-methyl-2-imidazoline,
2-(3-cyanophenyl)-4,4-bis(4-fluorophenyl)-5-hydroxymethyl-2-imidazoline,
2-(3-cyanophenyl)-4,4-bis(3-fluorophenyl)-2-imidazoline,
2-(3-cyanophenyl)-4-(3-quinolyl)-4-(2-thienyl)-2-imidazoline,
4-(4-bromophenyl)-2-(3-cyanophenyl)-4-phenyl-2-imidazoline,
4,4-bis(4-chlorophenyl)-2-(3-cyanophenyl)-2-imidazoline,
4-(4-chlorophenyl)-2-(3-cyanophenyl)-4-phenyl-2-imidazoline, 2-(3-cyanophenyl)-4-(4-fluorophenyl)-4-(3-quinolyl)-2-imidazoline,
2-(3-cyanophenyl)-4-(4-fluorophenyl)-4-phenyl-2-imidazoline,
2-(3-cyanophenyl)-4-phenyl-4-(4-vinylphenyl)-2-imidazoline,
4-(6-chloro-3-pyridyl)-2-(3-cyanophenyl)-4-(4-fluorophenyl)-2-imidazoline,
4-(5-chloro-2-thienyl)-2-(3-cyanophenyl)-4-(4-fluorophenyl)-2-imidazoline,
2-(3-cyanophenyl)-4-(4-methylphenyl)-4-phenyl-2-imidazoline,
2-(3-cyanophenyl)-4-(3-methylphenyl)-4-phenyl-2-imidazoline,
4,4-bis(4-fluorophenyl)-2-(3-nitrophenyl)-2-imidazoline,
2-(3-cyanophenyl)-4-phenyl-4-(3-quinolyl)-2-imidazoline,
2-(3-cyanophenyl)-4-(4-methoxyphenyl)-4-phenyl-2-imidazoline,
4-(3-chlorophenyl)-2-(3-cyanophenyl)-4-phenyl-2-imidazoline,
2-(3-cyanophenyl)-4-(4-fluorophenyl)-4-(5-methyl-2-thienyl)-2-imidazoline,
2-(3-cyanophenyl)-4-phenyl-4-(4-trifluoromethylphenyl)-2-imidazoline,
2-(3-cyanophenyl)-4-(3-methoxyphenyl)-4-phenyl-2-imidazoline,
2-(3-cyanophenyl)-4-(3,4-dimethylphenyl)-4-phenyl-2-imidazoline,
2-(3-cyanophenyl)-4-(4-fluorophenyl)-4-(3-vinylphenyl)-2-imidazoline,
2-(3-cyanophenyl)-4-(2-naphthyl)-4-(3-pyridyl)-2-imidazoline,
4-(3-bromophenyl)-2-(3-cyanophenyl)-4-(4-fluorophenyl)-2-imidazoline,
4-(2-chlorophenyl)-2-(3-cyanophenyl)-4-phenyl-2-imidazoline,
2-(3-cyanophenyl)-4-(4-fluorophenyl)-4-(6-quinolyl)-2-imidazoline,
2-(3-cyanophenyl)-4-phenyl-4-(2-thienyl)-2-imidazoline,
2-(3-cyanophenyl)-4-(4-dimethylaminophenyl)-4-phenyl-2-imidazoline,
2-(3-cyanophenyl)-4-(4-fluorophenyl)-4-(3-pyridyl)-2-imidazoline,
2-(3-cyanophenyl)-4-(4-formylphenyl)-4-phenyl-2-imidazoline,
2-(3-cyanophenyl)-4-(4-fluorophenyl)-4-(2-thienyl)-2-imidazoline,
4,4-diphenyl-2-pyrazinyl-2-imidazoline,
2-(3-cyanophenyl)-4,4-bis(4-methoxyphenyl)-2-imidazoline,
2-(3-cyanophenyl)-4-(4-fluorophenyl)-4-(3-formylphenyl)-2-imidazoline,
4,4-bis(4-fluorophenyl)-2-(3-methylsulfonylphenyl)-2-imidazoline,
4,4-bis(4-fluorophenyl)-2-(3-formylphenyl)-2-imidazoline,
2-(3-cyanophenyl)-4-(2-methylphenyl)-4-phenyl-2-imidazoline,
2-(3-cyanophenyl)-4-(4-fluorophenyl)-4-(3-hydroxymethylphenyl)-2-imidazoline,
2-(3-cyanophenyl)-4-(4-fluorophenyl)-4-(1,2,3,4-tetrahydro-1,5-naphthyridin-7-yl)-2-imidazoline,
2-(3-cyanophenyl)-4-(2-fluorophenyl)-4-(3-pyridyl)-2-imidazoline,
4-(4-biphenylyl)-2-(3-cyanophenyl)-4-phenyl-2-imidazoline,
2-(3-cyanophenyl)-4-(2-methoxyphenyl)-4-phenyl-2-imidazoline,
2-(3-cyanophenyl)-4-cyclohexyl-4-phenyl-2-imidazoline,
2-(3-cyanophenyl)-4-(4-fluorophenyl)-4-(4-pyridyl)-2-imidazoline,
4,4-bis(4-fluorophenyl)-2-(5-pyrimidinyl)-2-imidazoline,
2-(3-cyanophenyl)-4-cyclopentyl-4-phenyl-2-imidazoline,
2-(3-cyanophenyl)-4-cyclobutyl-4-phenyl-2-imidazoline,
4,4-bis(4-fluorophenyl)-2-(3-pyridazinyl)-2-imidazoline,
4-(4-fluorophenyl)-5-methyl-2-pyrazinyl-4-(3-quinolyl)-2-imidazoline,
(4S,5S)-4-(4-fluorophenyl)-4-(6-fluoro-3-pyridyl)-2-(3-methylsulfonylphenyl)-5-methyl-2-imidazoline,
(4R,5S)-4-(4-fluorophenyl)-4-(6-fluoro-3-pyridyl)-2-(3-methylsulfonylphenyl)-5-methyl-2-imidazoline,
(4S,5S)-2-(5-cyano-3-pyridyl)-4-(4-fluorophenyl)-4-(6-fluoro-3-pyridyl)-5-methyl-2-imidazoline,
(4R,5S)-2-(5-cyano-3-pyridyl)-4-(4-fluorophenyl)-4-(6-fluoro-3-pyridyl)-5-methyl-2-imidazoline,
(4S,5S)-2-(2-cyano-4-pyridyl)-4-(4-fluorophenyl)-4-(6-fluoro-3-pyridyl)-5-methyl-2-imidazoline,
(4R,5S)-2-(2-cyano-4-pyridyl)-4-(4-fluorophenyl)-4-(6-fluoro-3-pyridyl)-5-methyl-2-imidazoline,
(5R)-2-(2-cyano-4-pyridyl)-4,4-bis(4-fluorophenyl)-5-hydroxymethyl-2-imidazoline,
(5S)-2-(2-cyano-4-pyridyl)-4,4-bis(4-fluorophenyl)-5-methyl-2-imidazoline,
(4S,5S)-2-(2-cyano-4-pyridyl)-4-(4-fluorophenyl)-4-(2-fluoro-4-pyridyl)-5-methyl-2-imidazoline,
(4R,5S)-2-(2-cyano-4-pyridyl)-4-(4-fluorophenyl)-4-(2-fluoro-4-pyridyl)-5-methyl-2-imidazoline,
(5S)-2-(2-cyano-4-pyridyl)-4,4-bis(6-fluoro-3-pyridyl)-5-methyl-2-imidazoline,
4,4-bis(4-fluorophenyl)-5-methyl-2-pyrazinyl-2-imidazoline,
4,4-bis(4-fluorophenyl)-5-hydroxymethyl-2-pyrazinyl-2-imidazoline,
5-ethyl-4,4-bis(4-fluorophenyl)-2-pyrazinyl-2-imidazoline,
4,4-bis(4-fluorophenyl)-5-propyl-2-pyrazinyl-2-imidazoline,
4,4-bis(4-fluorophenyl)-2-(4-isothiazolyl)-2-imidazoline,
2-(3-pyridyl)-4,4-bis(4-fluorophenyl)-2-imidazoline,
2-(3-chlorophenyl)-4,4-bis(4-fluorophenyl)-2-imidazoline,
4,4-bis(4-fluorophenyl)-2-(3-trifluoromethylphenyl)-2-imidazoline,
2-(3-fluorophenyl)-4,4-bis(4-fluorophenyl)-2-imidazoline,
4,4-bis(4-fluorophenyl)-2-(3-trifluoromethoxyphenyl)-2-imidazoline,
4,4-bis(4-fluorophenyl)-2-(5-thiazolyl)-2-imidazoline,
4,4-bis(4-fluorophenyl)-2-(3-methylphenyl)-2-imidazoline,
4,4-bis(4-fluorophenyl)-2-(2-thienyl)-2-imidazoline,
2-(5-bromo-3-pyridyl)-4,4-bis(4-fluorophenyl)-2-imidazoline,
2-(3-bromophenyl)-4,4-bis(4-fluorophenyl)-2-imidazoline,
4,4-bis(4-fluorophenyl)-2-(3-thienyl)-2-imidazoline,
2-(4-cyano-2-pyridyl)-4,4-bis(4-fluorophenyl)-2-imidazoline,
(4S,5S)-2-(3-cyanophenyl)-4-(4-fluorophenyl)-4-(6-fluoro-3-pyridyl)-5-methyl-2-imidazoline,
(4R,5S)-2-(3-cyanophenyl)-4-(4-fluorophenyl)-4-(6-fluoro-3-pyridyl)-5-methyl-2-imidazoline,
2-(3-cyanophenyl)-4,4-bis(4-fluorophenyl)-5-(1-hydroxyethyl)-2-imidazoline,
(4S,5S)-2-(3-cyanophenyl)-4-(4-fluorophenyl)-4-(2-fluoro-4-pyridyl)-5-methyl-2-imidazoline,
(4R,5S)-2-(3-cyanophenyl)-4-(4-fluorophenyl)-4-(2-fluoro-4-pyridyl)-5-methyl-2-imidazoline,
(4S,5S)-4-(4-fluorophenyl)-4-(6-fluoro-3-pyridyl)-5-methyl-2-(1,2,5-thiadiazol-3-yl)-2-imidazoline, (4R,5S)-4-(4-fluorophenyl)-4-(6-fluoro-3-pyridyl)-5-methyl-2-(1,2,5-thiadiazol-3-yl)-2-imidazoline,
(5R)-4,4-bis(4-fluorophenyl)-5-hydroxymethyl-2-(6-hydroxy-2-pyridyl)-2-imidazoline,
(5S)-4,4-bis(4-fluorophenyl)-2-(6-hydroxy-2-pyridyl)-5-methyl-2-imidazoline,
(4S,5S)-2-(2-chloro-4-pyridyl)-4-(4-fluorophenyl)-4-(6-fluoro-3-pyridyl)-5-methyl-2-imidazoline,
(4R,5S)-2-(2-chloro-4-pyridyl)-4-(4-fluorophenyl)-4-(6-fluoro-3-pyridyl)-5-methyl-2-imidazoline,
(4S,5S)-4-(4-fluorophenyl)-4-(6-fluoro-3-pyridyl)-2-(6-hydroxy-2-pyridyl)-5-methyl-2-imidazoline,
(4R,5S)-4-(4-fluorophenyl)-4-(6-fluoro-3-pyridyl)-2-(6-hydroxy-2-pyridyl)-5-methyl-2-imidazoline,
(5S)-2-(3-cyanophenyl)-4,4-bis(6-fluoro-3-pyridyl)-5-methyl-2-imidazoline,
(4S,5R)-2-(3-cyanophenyl)-4-(4-fluorophenyl)-4-(6-fluoro-3-pyridyl)-5-hydroxymethyl-2-imidazoline,
(4R,5R)-2-(3-cyanophenyl)-4-(4-fluorophenyl)-4-(6-fluoro-3-pyridyl)-5-hydroxymethyl-2-imidazoline,
(4S,5S)-2-(3-cyanophenyl)-4-(4-fluorophenyl)-5-methyl-4-(1,5-naphthyridin-3-yl)-2-imidazoline,
(4R,5S)-2-(3-cyanophenyl)-4-(4-fluorophenyl)-5-methyl-4-(1,5-naphthyridin-3-yl)-2-imidazoline,
(4S,5S)-2-(3-cyanophenyl)-4-(6-fluoro-3-pyridyl)-4-(4-fluorophenyl)-5-methyl-2-imidazoline,
(4R,5S)-2-(3-cyanophenyl)-4-(6-fluoro-3-pyridyl)-4-(4-fluorophenyl)-5-methyl-2-imidazoline,
(5S)-2-(5-cyano-3-pyridyl)-4,4-bis(6-fluoro-3-pyridyl)-5-methyl-2-imidazoline,
(4S,5S)-2-(4-cyano-2-pyridyl)-4-(4-fluorophenyl)-4-(6-fluoro-3-pyridyl)-5-methyl-2-imidazoline,
(4R,5S)-2-(4-cyano-2-pyridyl)-4-(4-fluorophenyl)-4-(6-fluoro-3-pyridyl)-5-methyl-2-imidazoline,
(5R)-2-(4-cyano-2-pyridyl)-4,4-bis(4-fluorophenyl)-5-hydroxymethyl-2-imidazoline,
2-(4-cyano-2-pyridyl)-4-(4-fluorophenyl)-4-(6-fluoro-3-pyridyl)-2-imidazoline,
2-(4-cyano-2-pyridyl)-4-(4-fluorophenyl)-4-(2-fluoro-4-pyridyl)-2-imidazoline,
(4S,5R)-2-(4-cyano-2-pyridyl)-4-(4-fluorophenyl)-4-(6-fluoro-3-pyridyl)-5-hydroxymethyl-2-imidazoline,
(4R,5R)-2-(4-cyano-2-pyridyl)-4-(4-fluorophenyl)-4-(6-fluoro-3-pyridyl)-5-hydroxymethyl-2-imidazoline,
(4S,5S)-2-(6-cyano-2-pyridyl)-4-(4-fluorophenyl)-4-(6-fluoro-3-pyridyl)-5-methyl-2-imidazoline,
(4R,5S)-2-(6-cyano-2-pyridyl)-4-(4-fluorophenyl)-4-(6-fluoro-3-pyridyl)-5-methyl-2-imidazoline,
(4S,5S)-2-(4-cyano-2-pyridyl)-4-(4-fluorophenyl)-4-(2-fluoro-4-pyridyl)-5-methyl-2-imidazoline,
(4R,5S)-2-(4-cyano-2-pyridyl)-4-(4-fluorophenyl)-4-(2-fluoro-4-pyridyl)-5-methyl-2-imidazoline,
(5S)-2-(4-cyano-2-pyridyl)-4,4-bis(6-fluoro-3-pyridyl)-5-methyl-2-imidazoline,
(4S,5S)-2-(4-cyano-2-pyridyl)-4-(4-fluorophenyl)-5-methyl-4-(3-pyridyl)-2-imidazoline,
(4R,5S)-2-(4-cyano-2-pyridyl)-4-(4-fluorophenyl)-5-methyl-4-(3-pyridyl)-2-imidazoline,
(5R)-2-(4-cyano-2-pyrimidyl)-4,4-bis(4-fluorophenyl)-5-hydroxymethyl-2-imidazoline,
(4S,5S)-2-(4-cyano-2-pyrimidyl)-4-(4-fluorophenyl)-4-(6-fluoro-3-pyridyl)-5-methyl-2-imidazoline, or (4R,5S)-2-(4-cyano-2-pyrimidyl)-4-(4-fluorophenyl)-4-(6-fluoro-3-pyridyl)-5-methyl-2-imidazoline or the like.

The process for producing the compounds of the present invention is illustrated as follows.

The compounds of the present invention (I) can be synthesized, for example, by the following processes for production or the processes shown in Examples, but these embodiments are not intended to restrict the process for producing the compounds of the present invention (I).

Production Process 1

A compound represented by the general formula (II):

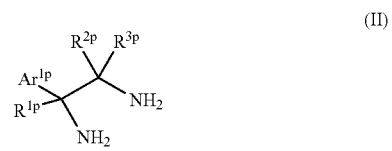

(II)

wherein $Ar^{1p}$ and $Ar^{3p}$ represent independently aryl or heteroaryl which may be substituted, the substituent being selected from the group consisting of cyano, halogen atom, nitro, lower alkyl, halo(lower)alkyl, cyclo(lower)alkyl(lower)alkyl, lower alkenyl, di-lower alkylamino, lower alkoxy, halo(lower)alkoxy, aryloxy, heteroaryloxy, lower alkylthio, formyl, lower alkanoyl, lower alkoxycarbonyl, di-lower alkylcarbamoyl, lower alkylsulfonyl, arylsulfonyl, aryl, heteroaryl and an optionally protected, hydroxy(lower)alkyl, lower alkylamino, lower alkanoylamino, lower alkylsulfonylamino, arylsulfonylamino, hydroxy, carboxyl, carbamoyl or lower alkylcarbamoyl group;

$R^{1p}$ represents cyclo(lower)alkyl or a group represented by the formula of —$Ar^{3p}$;

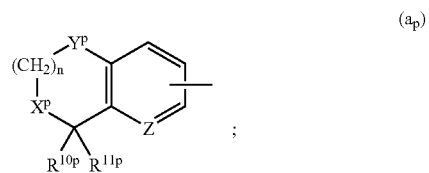

(a$_p$)

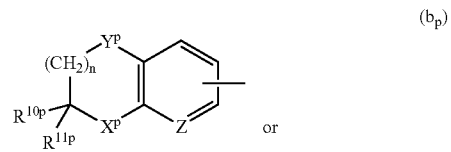

(b$_p$)

or

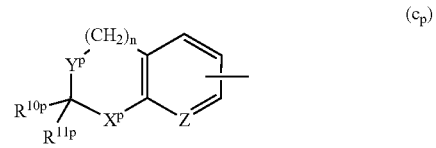

(c$_p$)

$R^{2p}$ and $R^{3p}$ represent independently hydrogen atom, cyclo(lower)alkyl or lower alkenyl or lower alkyl which may be substituted, the substituent being selected from the group consisting of halogen atom, di-lower alkylamino, lower alkoxy, formyl, lower alkoxycarbonyl, di-lower alkylcarbamoyl and an optionally protected, lower alkylamino, lower alkanoylamino, hydroxy or lower alkylcarbamoyl group;

both $R^{10p}$ and $R^{11p}$ represent hydrogen atom or they combine to represent an optionally protected oxo group;

$R^{12p}$ represents hydrogen atom, lower alkyl, or a protecting group for imino group;

$X^p$ and $Y^p$ represent independently methylene, ethenylene, a group represented by the formula of —$NR^{12p}$—, oxygen atom or sulfur atom;

n and Z represents have the same meanings as described above; is reacted with an acid addition salt of the compound represented by the general formula (III):

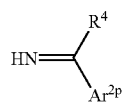

(III)

wherein $Ar^{2p}$ represents aryl or heteroaryl which may be substituted, the substituent being selected from the group consisting of cyano, halogen atom, nitro, lower alkyl, halo (lower)alkyl, cyclo(lower)alkyl(lower)alkyl, lower alkenyl, di-lower alkylamino, lower alkoxy, halo(lower)alkoxy, aryloxy, heteroaryloxy, lower alkylthio, formyl, lower alkanoyl, lower alkoxycarbonyl, di-lower alkylcarbamoyl, lower alkylsulfonyl, arylsulfonyl, aryl, heteroaryl and an optionally protected, hydroxy(lower)alkyl, lower alkylamino, lower alkanoylamino, lower alkylsulfonylamino, arylsulfonylamino, hydroxy, carboxyl, carbamoyl or lower alkylcarbamoyl group; $R^4$ represents amino or lower alkoxy;

to provide a compound represented by the general formula (IV):

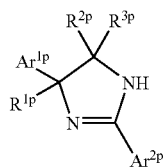

(IV)

wherein $Ar^{1p}$, $Ar^{2p}$, $R^{1p}$, $R^{2p}$ and $R^{3p}$ have the same meanings as described above;

optionally followed by elimination of a protecting group to give a compound represented by the general formula (I).

When a reactant has an amino, imino, hydroxy, carboxyl, oxo, carbonyl, or the like group which does not participate in the above reaction, the reaction may be carried out after protecting the amino, imino, hydroxy, carboxyl, oxo, carbonyl, or the like group with an protecting group for amino or imino, a protecting group for hydroxyl, a protecting group for carboxyl, or a protecting group for oxo or carbonyl, followed by elimination of the protecting group after completion of the reaction.

"Protecting group for amino or imino" preferably includes aralkyl (for example, benzyl, p-methoxybenzyl, 3,4-dimethoxybenzyl, o-nitrobenzyl, p-nitrobenzyl, benzhydryl, trityl, etc.); lower alkanoyl (for example, formyl, acetyl, propionyl, butyryl, pivaloyl, etc.); benzoyl; arylalkanoyl (for example, phenylacetyl, phenoxyacetyl, etc.); lower alkoxycarbonyl (for example, methoxycarbonyl, ethoxycarbonyl, propyloxycarbonyl, tert-butoxycarbonyl, etc.); aralkyloxycarbonyl (for example, benzyloxycarbonyl, p-nitrobenzyloxycarbonyl, phenethyloxycarbonyl, etc.); lower alkylsilyl (for example, trimethylsilyl, tert-butyldimethylsilyl, etc.); or the like, especially, acetyl, pivaloyl, benzoyl, ethoxycarbonyl, tert-butoxycarbonyl, or the like.

"Protecting group for hydroxy" preferably includes lower alkylsilyl (for example, trimethylsilyl, tert-butyldimethylsilyl, etc.); lower alkoxymethyl (for example, methoxymethyl, 2-methoxyethoxymethyl, etc.); tetrahydropyranyl; trimethylsilylethoxymethyl; aralkyl (for example, benzyl, p-methoxybenzyl, 2,3-dimethoxybenzyl, o-nitrobenzyl, p-nitrobenzyl, trityl, etc.); acyl (for example, formyl, acetyl, etc.), and the like, especially methoxymethyl, tetrahydropyranyl, trityl, trimethylsilylethoxymethyl, tert-butyldimethylsilyl, acetyl, or the like.

"Protecting group for carboxyl" preferably includes lower alkyl (for example, methyl, ethyl, propyl, isopropyl, tert-butyl, etc.); halo(lower)alkyl (for example, 2,2,2-trichloroethyl, etc.); lower alkenyl (for example, 2-propenyl, etc.); aralkyl (for example, benzyl, p-methoxybenzyl, p-nitrobenzyl, benzhydryl, trityl, etc.); or the like, especially, methyl, ethyl, tert-butyl, 2-propenyl, benzyl, p-methoxybenzyl, benzhydryl, or the like.

"Protecting group for oxo or carbonyl" includes acetal or ketal (for example, ethylene ketal, trimethylene ketal, dimethyl ketal, etc.), or the like.

The reaction between a compound represented by the general formula (II) and an acid addition salt of a compound represented by the general formula (III) is usually carried out by employing 1 to excessive moles, preferably 1 to 5 moles of the acid addition salt of the compound (III) per mole of the compound (II).

The acid addition salt of the compound (III) includes preferably, for example, hydrochloride, or the like.

The reaction is usually carried out in an inert solvent, and the inert solvent preferably includes, for example, alcohol (for example, methanol, ethanol, etc.), dimethylformamide, dimethyl sulfoxide, or a mixture thereof or the like.

Reaction temperature is usually –30° C. to 200° C., preferably 0° C. to 150° C.

Reaction time is usually 30 minutes to 7 days, preferably 2 hours to 5 days.

At the termination of the reaction, a crude product of a compound represented by the general formula (IV) can be obtained by usual treatment. Thus obtained compound represented by the general formula (IV) is purified by the conventional method, or not purified, optionally followed by cleavage of the protecting groups for amino, imino, hydroxyl, carboxyl, oxo, and carbonyl to give the compound represented by the general formula (I).

The cleavage of protecting groups may be carried out, for example, by the manner described in the literature (Confer Protective Groups in Organic Synthesis, T. W. Greene, John Wiley & Sons, (1981)) or by its similar manner, for example, solvolysis using, for example, 0.01 mole to a large excess of acid, preferably trifluoroacetic acid, formic acid, hydrochloric acid or the like, or 1 mole to a large excess of base, preferably potassium hydroxide, calcium hydroxide or the like; chemical reduction using metallic complex hydride, or the like; or catalytic reduction using palladium-carbon catalyst, Raney nickel catalyst or the like, depending upon the kinds of the aforesaid protecting groups, the stability of the desired compound (I) and so on.

Production Process 2

A compound represented by the general formula (II):

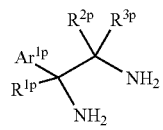

(II)

wherein $Ar^{1p}$, $R^{1p}$, $R^{2p}$ and $R^{3p}$ have the same meanings as described above;

is reacted in the presence of tri(lower)alkylaluminum with a compound represented by the general formula(V):

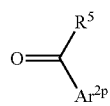

(V)

wherein $R^5$ represents lower alkoxy and $Ar^{2p}$ has the same meaning as described above;

to provide a compound represented by the general formula (IV):

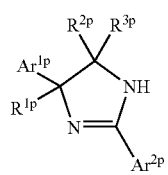

(IV)

wherein $Ar^{1p}$, $Ar^{2p}$, $R^{1p}$, $R^{2p}$ and $R^{3p}$ have the same meanings as described above;

optionally followed by elimination of a protecting group to give a compound represented by the general formula(I).

The reaction in the presence of tri(lower)alkylaluminum between a compound represented by the general formula (II) and a compound represented by the general formula (V) is usually carried out by employing 0.5 to 5 moles, preferably 0.7 to 3 moles of the compound (V) and 1 to excessive moles, preferably 1 to 5 moles of tri(lower)alkylaluminum per mole of the compound (II).

Tri(lower)alkylaluminum used for the reaction includes, for example, trimethylaluminum, triethylaluminum, tripropylaluminum, tributylaluminum, and the like.

The reaction is usually carried out in an inert solvent, and the inert solvent preferably includes, for example, benzene, toluene, xylene, methylene chloride, chloroform, hexane or a mixture thereof, or the like.

Reaction temperature is usually −20° C. to a boiling point of a solvent used for the reaction, preferably 0° C. to 110° C.

Reaction time is usually 30 minutes to 3 days, preferably 3 to 24 hours.

A compound represented by the general formula (I) can be produced by treating a reaction mixture in the usual way after elimination of a protecting group if the product has a protecting group after termination of the reaction, or by treating the mixture as it is in the usual way if the protecting group is absent in the reaction product.

Cleavage of the protecting groups and post-treatment, and the like can be carried out according to the method as described in the aforesaid production process 1.

Production Process 3

A compound represented by the general formula (II):

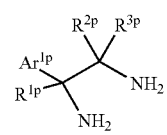

(II)

wherein $Ar^{1p}$, $R^{1p}$, $R^{2p}$ and $R^{3p}$ have the same meanings as described above;

is reacted with a compound represented by the general formula(VI):

(VI)

wherein $Ar^{2p}$ has the same meaning as described above; to provide a compound represented by the general formula (VII):

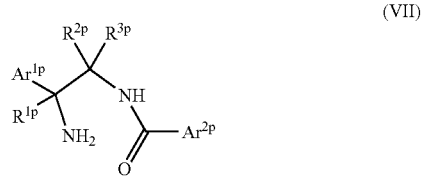

(VII)

wherein $Ar^{1p}$, $Ar^{2p}$, $R^{1p}$, $R^{2p}$ and $R^{3p}$ have the same meanings as described above.

Then the product (VII) is subjected intramolecular cyclocondensation reaction to provide a compound represented by the general formula (IV):

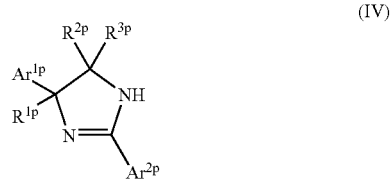

(IV)

wherein $Ar^{1p}$, $Ar^{2p}$, $R^{1p}$, $R^{2p}$ and $R^{3p}$ have the same meanings as described above;

optionally followed by cleavage of a protecting group to give a compound represented by the general formula(I).

The reaction between a compound represented by the general formula (II) and a compound represented by the general formula (VI) is usually carried out by employing 0.5 to excessive moles, preferably 1 to 2 moles of the compound (VI) per mole of the compound (II).

The reaction is usually carried out in an inert solvent, and the inert solvent preferably includes, for example, methylene chloride, chloroform, tetrahydrofuran, dimethylformamide, pyridine or a mixture thereof, or the like.

The aforesaid reaction is preferably carried out in the presence of a condensing agents, for example,
N,N'-dicyclohexylcarbodiimide,
N,N'-diisopropylcarbodiimide,
1-(3-dimethylaminopropyl)-3-ethylcarbodiimide,
1-(3-dimethylaminopropyl)-3-ethylcarbodiimide hydrochloride,
benzotriazol-1-yloxy-tris-(dimethylamino)phosphonium hexafluorophosphate,
benzotriazol-1-yloxy-tris-pyrrolidinophosphonium hexafluorophosphate, diphenylphosphoryl azide,
1,1-carbonyldiimidazole, or the like.

The aforesaid condensing agent is usually employed at 1 mole to excessive mole, preferably 1 mole to 3 moles per mole of the compound represented by the general formula (II).

Reaction temperature is usually −20° C. to the boiling point of a solvent used for the reaction, preferably 0° C. to 60° C.

Reaction time is usually 30 minutes to 3 days, preferably 1 to 24 hours.

A crude compound represented by the general formula (VII) can be produced by treating the reaction mixture in the usual way after termination of the reaction. Thus obtained crude compound represented by the general formula (VII) is purified by the conventional method, or not purified, followed by the next intramolecular cyclo-condensation reaction.

The intramolecular cyclo-condensation reaction by which the compound (IV) is produced from the compound (VII) is usually carried out in an inert solvent or without solvent.

The inert solvent preferably includes, for example, ethanol, propanol, butanol, pentanol, 1,4-dioxane, dimethoxyethane, dimethylformamide, dimethyl sulfoxide, benzene, toluene, xylene, or a mixture thereof, or the like.

Reaction temperature is usually room temperature to the boiling point of a solvent used for the reaction, preferably 80° C. to 190° C.

Reaction time is usually 5 hours to 7 days, preferably 12 hours to 3 days.

The cyclization reaction described above may be carried out in the presence of a dehydrating agent or a catalytic amount of Lewis acid. The dehydrating agent includes, for example, phosphorus oxychloride, phosphorus pentachloride, polyphosphoric acid, thionyl chloride or the like. The Lewis acid includes, for example, scandium trifluoromethanesulfonate, yttrium trifluoromethanesulfonate, lanthanum trifluoromethanesulfonate, trifluoromethanesulphonic acid lanthanide, or the like. The reaction is carried out preferably, without solvent or in a solvent, for example, methylene chloride, chloroform, benzene, toluene, xylene or a mixture thereof, or the like.

The aforesaid dehydrating agent is usually employed at 1 to excessive moles, preferably 2 to 10 moles per mole of the compound represented by the general formula (VII). The amount of Lewis acid is 1 to 50 molar %, preferably, 5 to 30 molar %.

Reaction temperature is usually room temperature to the boiling point of a solvent used for the reaction preferably.

Reaction time is usually 1 hour to 7 days, preferably 5 hours to 3 days.

A compound represented by the general formula (I) can be produced by treating a reaction mixture in the usual way after cleavage of a protecting group if the product has a protecting group or by treating the mixture as it is in the usual way if the protecting group is absent.

Cleavage of the protecting groups, post-treatment, and the like may be carried out according to the method as described in the aforesaid production process 1.

The compounds represented by the general formula (I) may readily be isolated and purified by the conventional separation technique, for example, solvent extraction, recrystallization, column chromatography, preparative thin layer chromatography, or/and the like.

These compounds may be converted into the pharmaceutical acceptable salts or esters by the conventional method, on the contrary, the conversion of the salts or esters into free compounds may also be carried out according to the conventional method.

The compounds represented by the general formula (II), (III), (V) or (VI) are, for example, commercially available, or are prepared according to the known methods, the methods as shown below or in Examples and Reference Examples, analogous methods hereto, or optionally in combination of those methods.

Production Process A-1

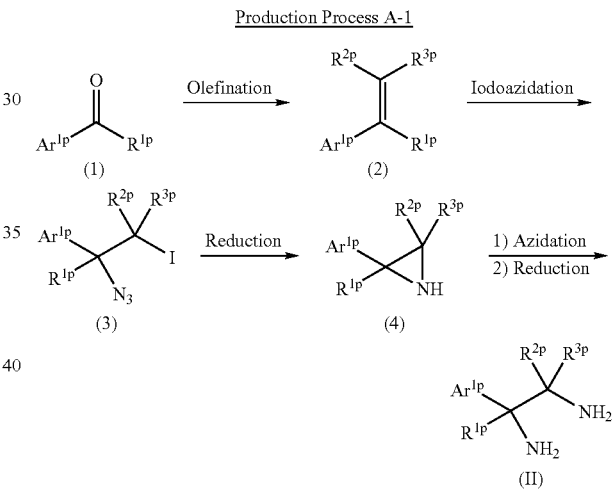

wherein $Ar^{1p}$, $R^{1p}$, $R^{2p}$ and $R^{3p}$ have the same meanings as described above.

This process refers to a process for producing a compound represented by the general formula (II). According to the present invention, the compound (II) may be prepared by subjecting process that a compound represented by the general formula (1) to olefination to give a compound represented by the general formula (2), subjecting the compound (2) to iodoazidation to give a compound represented by the general formula (3), subjecting the compound (3) to reduction to give a compound represented by the general formula (4), and subjecting the compound (4) to azidation, followed by reduction.

Regarding the olefination reaction in the step for producing the compound (2) from the compound (1), olefination reaction for oxo well-known per se in the field of organic chemistry, for example, the so-called Horner Emmons reaction, Wittig reaction, Peterson olefination, and the like can be applied.

In the step for producing the compound (3) from the compound (2), iodomonochloride and iodoazide generated from metal azide, for example, silver azide, potassium azide, sodium azide or the like may be reacted with the compound (2).

The reaction is usually carried out in an inert solvent, for example, methylene chloride, chloroform, acetonitrile, benzene, toluene, or a mixture thereof, or the like using 1 to excessive moles, preferably 1 to 2 moles of iodoazide per mole of the compound (2).

Reaction temperature is usually 0° C. to the boiling point of a solvent used for the reaction, preferably room temperature to 80° C. Reaction time is usually 30 minutes to 7 days, preferably 2 hours to 5 days.

In the step for producing the compound (4) from the compound (3), reduction reaction of azide known per se in the field of organic chemistry may be applied. More concretely, chemical reduction using, for example, metal, metallic complex hydride, triphenylphosphine, or the like, or catalytic reduction using palladium-carbon catalyst, Raney nickel catalyst, or the like may be applied.

In the process for producing the compound (II) from the compound (4), usually the reaction is made with azide compound (for example, tetraalkylammonium azide, potassium azide, sodium azide or the like) in the presence of acid (for example, acetic acid, ammonium chloride), followed by reduction of the azide group of the obtained compound according to the method well-known per se in the field of organic chemistry.

The solvent used in the step for reacting azide compound, includes, for example, alcohol (for example, methanol, ethanol or the like), dimethyl sulfoxide, dimethylformamide, tetrahydrofuran, water or the like, or a mixture thereof or the like preferably.

Reaction temperature is usually 0° C. to the boiling point of a solvent used for the reaction, preferably room temperature to 100° C. Reaction time is usually 3 hours to 1 day preferably.

In the step for reduction of azide, more concretely, reduction can be carried out by chemical reduction using, for example, metal, metallic complex hydride, triphenylphosphine, or the like, or catalytic reduction using palladium-carbon catalyst, Raney nickel catalyst, or the like.

The compounds represented by the general formula (1) and raw materials used for the olefination reaction may be commercially available, or can be prepared according to the known methods, or in Examples and Reference Examples, or analogous methods hereto, optionally in combination.

Production Process A-2

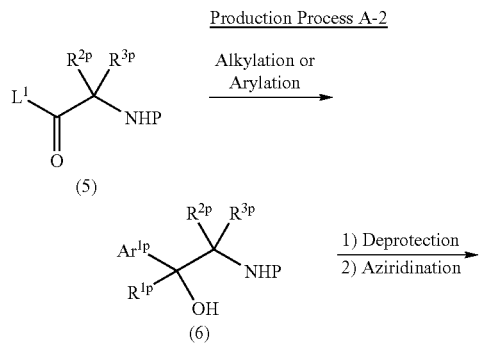

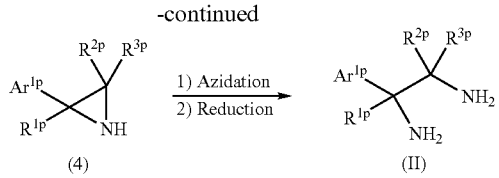

wherein $L^1$ represents hydrogen atom or a leaving group; P represents a protecting group for amino and $Ar^{1p}$, $R^{1p}$, $R^{2p}$ and $R^{3p}$ have the same meanings as described above.

This process is the alternative process for producing a compound represented by the general formula (II). According to this method, the compound (II) may be prepared by subjecting a compound represented by the general formula (5) is successively subjected to alkylation or arylation in this order on the activated carbonyl groups thereof to give a compound represented by the general formula (6), subjecting the compound (6) to cleavage of a protecting group for the amino group to produce the hydroxylamine compound, followed by aziridination with intramolecular dehydration of the generated hydroxyamine compound to give a compound represented by the general formula (4), and subjecting the compound (4) to azidation, followed by reduction.

A leaving group for $L^1$ preferably includes, for example, halogen atom, alkoxy, amide or the like.

A protecting group for amino represented by P includes a protecting group for amino as described in Production process 1 and with regard to the method for cleavage of a protecting group, and the method as described in Production process 1 can be applied.

The step for producing the compound (6) from the compound (5) may be carried out usually by subjecting the compound (5) to reaction with an organometallic compound, for example, alkyl lithium, aryl lithium, alkyl magnesium, aryl magnesium, alkyl zinc, aryl zinc, alkyl copper, aryl copper, or the like, which has a group represented by $Ar^{1p}$ or $R^{1p}$ as alkyl or aryl.

The reaction is carried out by the use of 1 to excessive moles, preferably, 2 to 5 moles of the aforesaid organometallic compound per mole of the compound (5) in an inert solvent, for example, an ether solvent (for example, diethyl ether, tetrahydrofuran, 1,2-dimethoxyethane), or a mixture thereof or the like.

Reaction temperature is usually −130° C. to the boiling point of a solvent used for the reaction, preferably, −100° C. to room temperature, and reaction time is usually 30 minutes to 2 days, preferably 1 hour to 1 day.

In case when $L^1$ is hydrogen atom, the compound (6) can be prepared by oxidation of an alcohol compound obtained by alkylation or arylation to give the corresponding ketone compound by the oxidation being well-known per se in the field of organic chemistry and then by alkylation or arylation of the obtained ketone compound again.

The step for producing the compound (4) from the compound (6) may so be carried out by reacting the hydroxyamino compound obtained after elimination of the protecting group P with halide of trialkyl or triaryl phosphine (for example, dichlorotriethyl phosphorane, dichlorotributyl phosphorane, dichlorotriphenyl phosphorane, dibromotriethyl phosphorane, dibromotributyl phosphorane, dibromotriphenyl phosphorane or the like) usually in the presence of base (for example, triethylamine, diisopropylamine, N,N-diisopropylethylamine, pyridine or the like)

The reaction is usually carried out by employing 1 to excessive moles, preferably 2 to 7 moles of a base and 0.5 to excessive moles, preferably 1 to 5 moles of halide of trialkyl or triaryl phosphine relative to 1 mole of the compound (6) in an inert solvent, for example, diethyl ether, tetrahydrofuran, 1,2-dimethoxyethane, toluene, benzene, dichloromethane, 1,2-dichloroethane, chloroform, acetonitrile or a mixture thereof, and the like.

Reaction temperature is usually −50° C. to the boiling point of a solvent used for the reaction, preferably, 0° C. to 70° C. and reaction time is usually 30 minutes to 3 days, preferably 1 hour to 24 hours.

The method as described in Production process A-1 can be applied to the step for preparing the compound (II) from the compound (4).

Throughout a series of steps for preparing the compound (II) from the compound (5) as described above, configuration on carbon atoms bonding to $R^{2p}$ and $R^{3p}$ remains unchanged. Therefore, in case $Ar^{1p}$ and $R^{1p}$ of the desired compound are identical, optically active compound (II) can be prepared by employing an optically active amino acid derivative as the compound represented by the general formula (5) of the raw material. On the contrary, in case $Ar^{1p}$ and $R^{1p}$ of the desired compound are different, an optically active compound (II) can be prepared by reacting an optically active amino acid derivative as the compound represented by the general formula (5) of the raw material, followed by separating the mixture of usually generated diastereoisomers based on configuration on carbon atoms bonding to $Ar^{1p}$ and $R^{1p}$ at an appropriate stage using the known method per se and then followed by reacting respectively corresponding optically active compound in the step hereafter.

Further, the compounds represented by the general formula (5) and organic metal compounds for alkylation or arylation are commercially available, or are prepared according to the methods described in the known methods, or in Examples and Reference Examples, or analogous methods hereto, or optional combination of those methods.

Production Process B

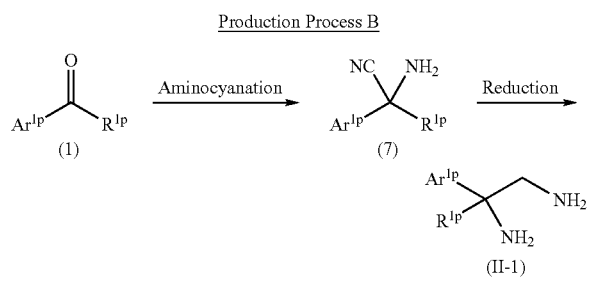

wherein $Ar^{1p}$ and $R^{1p}$ have the same meanings as described above.

This process refers to the process for producing a compound represented by the general formula (II-1). The compound (II-1) may be prepared by the present process in which a compound represented by the general formula (1) is subjected to aminocyanation of oxo group of the compound represented by the general formula (1) to give the compound represented by the general formula (7), followed by reduction of the cyano group of the compound (7).

In the steps for preparing the compound (7) from the compound (1), the so-called Strecker's synthetic method well-known per se in the field of organic chemistry, or an improved method thereof can be applied, In the step for preparing the compound (II-1) from the compound (7), reduction reaction of a cyano group well-known per se in the field of organic chemistry, that is, for example, chemical reduction using metal, or metallic complex hydride, or the like, or catalytic reduction or the like can be applied.

Further, the raw materials for the reaction of aminocyanation are commercially available, or are prepared according to the methods described in the known methods, or in Examples and Reference Examples, analogous methods hereto, or optional combination of those methods.

The specific example of the compound represented by the general formula (II) or (II') is, for example,
1,1-bis(4-fluorophenyl)-1,2-ethanediamine,
1-(4-fluorophenyl)-1-(1,5-naphthyridin-3-yl)-1,2-ethanediamine,
1,1-bis(4-fluorophenyl)-1,2-propanediamine,
(2R)-1,1-bis(4-fluorophenyl)-3-(methoxymethoxy)-1,2-propanediamine,
(2S)-1,1-bis(4-fluorophenyl)-1,2-propanediamine,
(2S)-1,1-bis(6-fluoro-3-pyridyl)-1,2-propanediamine,
(2S)-1,1-bis(2-fluoro-4-pyridyl)-1,2-propanediamine,
(2S)-1-(4-fluorophenyl)-1-(6-fluoro-3-pyridyl)-1,2-propanediamine,
(1S,2S)-1-(4-fluorophenyl)-1-(6-fluoro-3-pyridyl)-1,2-propanediamine,
(1R,2S)-1-(4-fluorophenyl)-1-(6-fluoro-3-pyridyl)-1,2-propanediamine,
(2R)-1-(4-fluorophenyl)-1-(6-fluoro-3-pyridyl)-3-(methoxymethoxy)-1,2-propanediamine,
(1S,2R)-1-(4-fluorophenyl)-1-(6-fluoro-3-pyridyl)-3-(methoxymethoxy)-1,2-propanediamine,
(1R,2R)-1-(4-fluorophenyl)-1-(6-fluoro-3-pyridyl)-3-(methoxymethoxy)-1,2-propanediamine,
(1S,2S)-1-(4-fluorophenyl)-1-(2-fluoro-4-pyridyl)-1,2-propanediamine,
(1R,2S)-1-(4-fluorophenyl)-1-(2-fluoro-4-pyridyl)-1,2-propanediamine,
(1S,2S)-1-(4-fluorophenyl)-1-(1,5-naphthyridin-3-yl)-1,2-propanediamine,
(1R,2S)-1-(4-fluorophenyl)-1-(1,5-naphthyridin-3-yl)-1,2-propanediamine,
(1S,2S)-1-(4-fluorophenyl)-1-(3-pyridyl)-1,2-propanediamine,
(1R,2S)-1-(4-fluorophenyl)-1-(3-pyridyl)-1,2-propanediamine, or the like.

The utility of compounds of the present invention as a medicament is proved by showing NPY antagonistic activity, for example, in the following pharmacological tests.

Pharmacological Test 1 (NPY Binding Inhibition Test)

cDNA sequence encoding human NPY Y5 receptor (Confer description of International patent publication number WO96/16542)was cloned into expression vectors pcDNA3, pRc/RSV (made by Invitrogen Inc.) and pCI-neo(made by Promega Inc.). These obtained expression vectors were transfected to host cells COS-7, CHO and LM(tk−) (American Type Culture Collection) by cationic lipid method (Confer Proceedings of the National Academy of Sciences of the United States of America, vol. 84: 7413(1987)) to give recombinant cells which express NPY Y5 receptor.

A membrane sample prepared from the cells which expressed NPY Y5 receptor was incubated together with a test compound and ($^{125}$I) peptideYY (made by NEN) (20, 000 cpm) in an assay buffer (25 mM Tris buffer, pH7.4, containing 10 mM magnesium chloride, 1 mM phenylmethylsulfonyl fluoride, 0.1% bacitracin and 0.5% bovine serum albumin) at 25° C. for 2 hours, then filtered through a glass filter GF/C and washed with 5 mM Tris buffer (pH7.4) containing 0.3% BSA. The radioactivity on the glass filter was measured. Nonspecific binding was measured in the presence of 1 μM peptideYY and a 50% Inhibitory Concentration($IC_{50}$) of the test compound against specific peptide YY binding was determined (Confer Endocrinology, vol. 131: 2090(1992)). The results are summarized in Table 1.

(Table 1)
Inhibitory Activities on NPY Receptor Binding

| Compounds | $IC_{50}$ ( nM) |
|---|---|
| Example 5–1 | 2.3 |
| Example 7 | 3.4 |
| Example 13 | 1.7 |

As shown above, compounds of this invention potently inhibited peptideYY (NPY homoloque) binding to NPY Y5 receptors.

Pharmacological Test 2 (Antagonistic Effect on Feeding Behavior Induced by D-Trp$^{34}$NPY)

An chronic guide cannula (26 gauge, length 11 mm) was inserted by stereotactic surgery into the third ventricle of male SD rats (7–8 weeks old, 200–300 g) anesthetized with Ketamine.Xylazine (single intraperitoneal administration of 74 and 11 mg/kg) and fixed by dental resin. The top of the cannula was located 2.2 mm behind bregma, on the median line and 8 mm depth from the surface of cranial bone. After about 1-week recovery period, D-Trp$^{34}$ NPY (1 μg/0.4 μL/head, artificial cerebrospinal fluid containing 0.05% bovine serum albumin) was injected into the third ventricle. A test compound suspended in aqueous 0.5% methylcellulose solution was administered orally 2 hours before the administration of D-Trp$^{34}$ NPY and the food consumption was measured for 2 hours after administration of D-Trp$^{34}$ NPY.

Compounds of the present invention significantly inhibited the increase in food consumption induced by D-Trp$^{34}$ NPY (homologue of NPY) which was administered to the third ventricle.

Pharmacological Test 3 (Test for Pharmacokinetics)

The tested compound was administered orally or intravenously to male SD rats (7–10 weeks old, 200–400 g) under overnight fasting condition, and about 100 μL of blood was taken from tail vein using a heparinized capillary at predefined time points. The blood samples were separated by centrifuge (4° C., 6,000 rpm, for 10 minutes) to obtain plasma. To the plasma, 3-fold volume of ethanol containing the internal standard substances was added and the mixture was stirred, then left at −20° C. for 20 minutes, followed by centrifugation (4° C., 10,000 rpm for 10 minutes). The supernatant was analyzed by LC/MS/MS and then the concentration of the test compound in plasma was measured by the relative calibration curve method.

Consequently, for example, the compound of Example 7 was found to be biological availability ratio: 35% and half-life in blood: 5.1 hours.

Pharmacological Test 4 (Brain and Cerebrospinal Fluid Penetration Test)

The tested compound was administered orally or intravenously to male SD rats (7–10 weeks old, 200–400 g). The rats anesthetized with ether, and the all blood were taken at predefined time points with a heparinized syringe from the abdominal aorta. Further, the rats were cut the skin of occipital region of head and inserted a 30 G dental needle between cervical vertebrae, into subarachnoid cavity. And then, 50–100 μL of cerebrospinal fluid was collected in a 1 mL syringe through a tube connected with the 30 G dental needle, followed by taking out the brain. To the plasma obtained from the centrifuged blood sample (4° C., 6,000 rpm, for 10 minutes), 3-fold volume of ethanol including the internal standard substances was added and the mixture was stirred. To the brain sample, 2 mL of water was added and the mixture was homogenized. To an aliquot of the homogenized mixture, 3-fold volume of ethanol including the internal standard substances was added, followed by stirring. To the cerebrospinal fluid, 3-fold volume of ethanol containing the internal standard substances was added, followed by stirring. The above samples were left at −20° C. for 20 minutes and separated by centrifuge (4° C., 12,000 g, for 10 minutes). The supernatant was analyzed by LC/MS/MS and then each concentration in plasma, brain and cerebrospinal fluid was measured by the relative calibration curve method.

Consequently, for example, the compound of Example 7 showed cerebral concentration: 2.95 nM/g, cerebrospinal concentration: 0.032 μM and plasma concentration: 0.73 μM in 2 hours after oral administration (10 mg/kg)

Compounds of the general formula (I) can be administered orally or parenterally and may be formulated in the form suitable for administration to provide an agent for treatment of, for example, cardiovascular disorders (for example, hypertension, nephropathy, heart disease, vasospasm, arteriosclerosis) central nervous system disorders (for example, bulimia, depression, anxiety, seizure, epilepsy, dementia, pain, alcoholism, drug withdrawal), metabolic diseases (for example, obesity, diabetes, hormone abnormality, hypercholesterolemia, hyperlipidemia), sexual and reproductive dysfunction, gastric-intestinal disorder such as the inhibition of gastro-intestinal motility, respiratory disorder, inflammation or glaucoma or the like. In clinical use, compounds of the present invention can be administered after being formulated, together with pharmaceutically acceptable additives, into an appropriate preparation according to the mode of administration. For said additives, those which are usually used in the field of pharmaceutical formulation may be used, for example, gelatin, lactose, sucrose, titanium oxide, starch, crystalline cellulose, hydroxypropylmethylcellulose, carboxymethylcellulose, corn starch, microcrystalline wax, white petrolatum, magnesium aluminomethasilicate, anhydrous calcium phosphate, citric acid, trisodium citrate, hydroxypropyl cellulose, sorbitol, sorbitan fatty acid ester, polysorbate, sucrose fatty acid ester, polyoxyethylene, hydrogenated castor oil, polyvinylpyrrolidone, magnesium stearate, light anhydrous silicic acid, talc, vegetable oil, benzyl alcohol, gum arabic, propylene glycol, polyalkylene glycol, cyclodextrin or hydroxypropyl cyclodextrin.

A mixture with said additives may be formulated in the form of solid preparations (for example, tablets, capsules, granules, powder, suppositories); or liquid preparations (for example, syrups, elixirs, injections). Such preparations may be formulated according to techniques well-known in the art of pharmaceutical formulation. Liquid preparations may be in the form of preparations which are dissolved or suspended in water or other appropriate media when used and especially injectable preparations may be dissolved or suspended in physiological saline or glucose solution if necessary, optionally together with a buffer and preservative.

Such preparations may contain 1.0 to 100 wt. %, preferably 1.0 to 60 wt. % of compounds of this invention and may also contain therapeutically effective other compounds.

The compounds of the present invention can be used in combination with other agents useful for treating metabolic and/or feeding disorders. The individual components of such combinations can be administered separately at different times during the course of therapy or concurrently in divided or single dosage forms. The present invention is therefore to be understood as embracing all such regimes of simultaneous or alternating treatment and the term "administering" is to be interpreted accordingly. It will be understood that the scope of combinations of the compounds of the present invention with other agents useful for treating metabolic and/or feeding disorders includes in principle any combination with any pharmaceutical compositions useful for treating metabolic and/or feeding disorders.

When compounds of the present invention are used clinically, the dose and frequency of dosage may be varied depending upon the sex, age, body weight, the degree of symptoms and the kind and range of the desired treatment effects. A daily dose for an adult is 0.01 to 100 mg/kg, preferably 0.03 to 1 mg/kg orally in a single or divided doses per day or 0.001 to 10 mg/kg, preferably 0.001 to 1.0 mg/kg parenterally, preferably in a single or divided doses per day.

An ordinarily skilled physician, veterinarian or clinician can readily determine and prescribe the effective amount of the drug required to inhibit, control or arrest the progress of the condition.

BEST MODE FOR CARRYING OUT THE INVENTION

The present invention will be explained more concretely by the use of Examples and Reference Examples, but the invention is not to be limited to those examples.

The compound having the symbol "*" in structural formula, means the compound of a substantially single configuration at asymmetric carbon atom, to which the symbol is attached.

Melting point was determined by using Model MP-S3 (produced by Yanagimoto Co. Ltd.,) and its result was stated without correcting. Also, the mass spectrum was determined by electrospray ionization method (ESI) using QuattroII (Micromass Ltd.,).

EXAMPLE 1

Production of 2-(3-cyanophenyl)-4,4-bis(4-fluorophenyl)-2-imidazoline

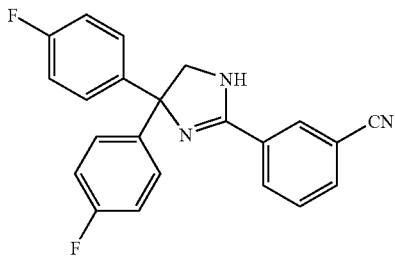

To a solution of 1,1-bis(4-fluorophenyl)-1,2-ethanediamine (500 mg) in methanol (10 mL) was added 3-cyanobenzeneimidic acid methyl ester (792 mg), and the mixture was stirred at room temperature for 18 hrs. After concentrating the reaction mixture, the residue was dissolved in ethyl acetate (30 mL), washed with saturated sodium hydrogen carbonate aqueous solution and saturated sodium chloride aqueous solution in this order, and dried over anhydrous sodium sulfate. Sodium sulfate was removed by filtration, and the organic solvent was evaporated in vacuo. The obtained residue was purified by silica gel column chromatography (C-300; hexane:ethyl acetate=3:1→2:1) to give the objective compound (370 mg).

Mass spectrum (ESI): 360.2

$^1$HNMR(300 MHz, CDCl$_3$,δppm): 4.15(1.4H,brs), 4.57 (0.7H,brs), 5.10(0.7H,brs), 5.38(0.3H,brs), 6.94–7.08(4H, m), 7.22–7.43(4H,m), 7.54(1H,t,J=7.8 Hz), 7.74(1H,d,J=7.8 Hz), 8.11(1H,d,J=7.6 Hz), 8.19(1H,s)

EXAMPLE 2

Production of 4,4-bis(4-fluorophenyl)-2-pyrazinyl-2-imidazoline

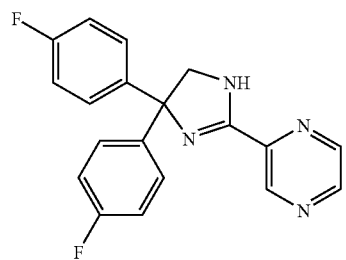

To a solution of 1,1-bis(4-fluorophenyl)-1,2-ethanediamine(500 mg) in methanol(10 mL) was added pyrazineimidic acid methyl ester (385 mg), and the mixture was stirred at room temperature for 18 hrs. After concentrating the reaction mixture, the residue was dissolved in ethyl acetate (50 ml), washed with saturated sodium hydrogen carbonate aqueous solution and saturated sodium chloride aqueous solution in this order, and dried over anhydrous sodium sulfate. Sodium sulfate was removed by filtration, and the organic solvent was evaporated in vacuo. The obtained residue was purified by silica gel column chromatography (C-300; hexane:ethyl acetate=1:1) to give the objective compound (446 mg).

Melting point 144–146° C.

$^1$HNMR(300 MHz, CDCl$_3$,δppm): 4.17(1.4H,brs), 4.65 (0.6H,brs), 6.08(0.7H,brs), 6.51(0.3H,brs), 6.96–7.04(4H, m), 7.26–7.50(4H,m), 8.54(1H,s), 8.66(1H,d,J=2.4 Hz), 9.45(0.3H,brs), 9.56(0.7H,brs)

EXAMPLE 3

Production of 2-(3-cyanophenyl)-4-(4-fluorophenyl)-4-(1,5-naphthyridin-3-yl)-2-imidazoline

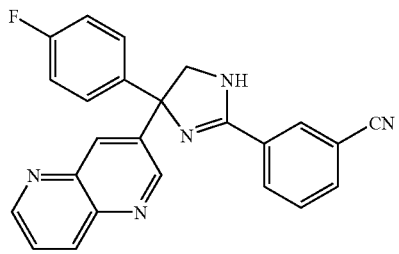

To a solution of 1-(4-fluorophenyl)-1-(1,5-naphthyridin-3-yl)-1,2-ethanediamine (17 mg) in methanol (1 mL) was added 3-cyanobenzeneimidic acid methyl ester (23 mg), and the mixture was stirred at room temperature for 19 hrs. To the reaction mixture was added chloroform and insolubles were removed by filtration, followed by concentration of the filtrate in vacuo. The residue was purified by preparative thin-layer chromatography (100% ethyl acetate) to give the objective compound (8.0 mg).

Mass spectrum (ESI): 394.0

$^1$HNMR(300 MHz, CDCl$_3$,δppm): 4.21–4.26(1H,m), 4.39–4.44(1H,m), 5.15(1H,brs), 7.02–7.09(2H,m), 7.45–7.51(1H,m), 7.58(2H,t,J=7.8 Hz), 7.60–7.65(1H,m), 7.78(1H,dt,J=1.4 Hz,7.7 Hz), 8.13–8.17(1H,m), 8.22(1H, brs), 8.36–8.41(2H,m), 8.95–8.97(1H,m), 9.06(1H,brs)

EXAMPLE 4

Production of 2-(3-cyanophenyl)-4,4-bis(4-fluorophenyl)-5-methyl-2-imidazoline

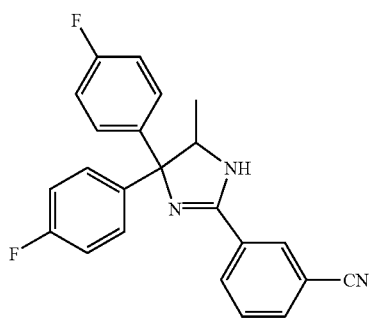

1,1-bis(4-fluorophenyl)-1,2-propanediamine(50 mg) was dissolved in methanol(1 mL), and to the solution was added 3-cyanobenzeneimidic acid methyl ester (75 mg). The mixture was stirred at room temperature for 24 hrs. After chloroform (5 ml) was added to the reaction mixture, insolubles were removed by filtration. After concentrating the filtrate in vacuo, the obtained residue was purified by silica gel column chromatography (C-300; hexane:ethyl acetate=3:1→1:1) to give the objective compound (10 mg).

Mass spectrum (ESI): 374.1

$^1$HNMR(300 MHz, CDCl$_3$,δppm): 0.92(3H,d,J=6.6 Hz), 4.60–5.40(2H,m), 7.40–7.50(2H,m), 7.52–7.57(1H,m), 7.72–7.76(1H,m), 8.10(1H,d,J=8.0 Hz), 8.17(1H,s)

EXAMPLE 5

Production of 2-(3-cyanophenyl)-4,4-bis(4-fluorophenyl)-5-hydroxethyl-2-imidazoline

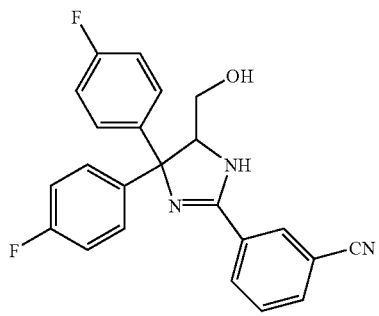

1,1-bis(4-fluorophenyl)-3-methoxymethoxy-1,2-propanediamine(218 mg) was dissolved in methanol(3 mL), and to the solution was added 3-cyanobenzeneimidic acid methyl ester (266 mg), and the mixture was stirred at room temperature for 17 hrs. To the reaction mixture was added an additional amount of 3-cyanobenzeneimidic acid methyl ester (266 mg), and the reaction mixture was stirred at room temperature for 6 hrs. To the reaction mixture was added ethyl acetate (50 ml), and the organic layer was washed with saturated sodium hydrogen carbonate aqueous solution and saturated sodium chloride aqueous solution in this order, and dried over anhydrous sodium sulfate. Sodium sulfate was removed by filtration, and then the organic solvent was evaporated in vacuo. The obtained residue was purified by silica gel column chromatography (C-300; hexane:ethyl acetate=2:1) to give 2-(3-cyanophenyl)-4,4-bis(4-fluorophenyl)-5-[(methoxymethoxy)methyl]-2-imidazoline (146 mg) as colorless oil. The protected compound (115 mg) was dissolved in the mixture solution of 2N hydrochloric acid (1.5 mL) and tetrahydrofuran (1.5 ml), and the solution was stirred at 50° C. for 3 days. After cooling the mixture to the room temperature by standing it at room temperature and neutralizing with saturated sodium hydrogen carbonate aqueous solution, the mixture was extracted with ethyl acetate. The organic layer was washed with saturated sodium chloride aqueous solution, and dried over anhydrous sodium sulfate. Sodium sulfate was removed by filtration, and the organic solvent was evaporated in vacuo to give the title compound (105 mg).

Mass spectrum(ESI): 390.0

$^1$HNMR(300 MHz, CDCl$_3$,δppm): 3.09,3.30[2H(3.09, brs),(3.30,dd,J=4.5 Hz,10.5 Hz)],4.68(1H,brs),5.59(1H,brs), 7.01(4H,m),7.23(2H, m),7.48(2H,brs),7.56(1H,t,J=7.8 Hz), 7.76(1H,d,J=7.8 Hz),8.11(1H,d,J=7.8 Hz),8.21(1H,s)

According to any one of the methods described in above-mentioned Example 1 to 5, corresponding diamine and imidic acid methyl ester were reacted to give the following compounds.

EXAMPLE 5-1

2-(3-cyanophenyl)-4,4-bis(3-fluorophenyl)-2-imidazoline

Mass spectrum(ESI): 360.1

EXAMPLE 5-2

2-(3-cyanophenyl)-4-(3-quinolyl)-4-(2-thienyl)-2-imidazoline

Mass spectrum(ESI): 381.0

EXAMPLE 5-3

4-(4-bromophenyl)-2-(3-cyanophenyl)-4-phenyl-2-imidazoline

Mass spectrum(ESI): 402.0

EXAMPLE 5-4

4,4-bis(4-chlorophenyl)-2-(3-cyanophenyl)-2-imidazoline

Mass spectrum(ESI): 392.0

EXAMPLE 5-5

4-(4-chlorophenyl)-2-(3-cyanophenyl)-4-phenyl-2-imidazoline

Mass spectrum(ESI): 358.1

EXAMPLE 5-6

2-(3-cyanophenyl)-4-(4-fluorophenyl)-4-(3-quinolyl)-2-imidazoline

Mass spectrum(ESI): 393.1

EXAMPLE 5-7

2-(3-cyanophenyl)-4-(4-fluorophenyl)-4-phenyl-2-imidazoline

Mass spectrum(ESI): 342.2

EXAMPLE 5-8

2-(3-cyanophenyl)-4-phenyl-4-(4-vinylphenyl)-2-imidazoline

Mass spectrum(ESI): 350.1

EXAMPLE 5-9

4-(6-chloro-3-pyridyl)-2-(3-cyanophenyl)-4-(4-fluorophenyl)-2-imidazoline

Mass spectrum(ESI): 377.0

EXAMPLE 5-10

4-(5-chloro-2-thienyl)-2-(3-cyanophenyl)-4-(4-fluorophenyl)-2-imidazoline

Mass spectrum(ESI): 382.1

EXAMPLE 5-11

2-(3-cyanophenyl)-4-(4-methylphenyl)-4-phenyl-2-imidazoline

Melting point: 179–180° C.

EXAMPLE 5-12

2-(3-cyanophenyl)-4-(3-methylphenyl)-4-phenyl-2-imidazoline

Mass spectrum(ESI): 338.1

EXAMPLE 5-13

4,4-bis(4-fluorophenyl)-2-(3-nitrophenyl)-2-imidazoline

Melting point: 156–158° C.

EXAMPLE 5-14

2-(3-cyanophenyl)-4-phenyl-4-(3-quinolyl)-2-imidazoline

Mass spectrum(ESI): 375.2

EXAMPLE 5-15

2-(3-cyanophenyl)-4-(4-methoxyphenyl)-4-phenyl-2-imidazoline

Mass spectrum(ESI): 354.0

EXAMPLE 5-16

4-(3-chlorophenyl)-2-(3-cyanophenyl)-4-phenyl-2-imidazoline hydrochloride

Mass spectrum(ESI): 358.1

EXAMPLE 5-17

2-(3-cyanophenyl)-4-(4-fluorophenyl)-4-(5-methyl-2-thienyl)-2-imidazoline

Mass spectrum(ESI): 362.1

EXAMPLE 5-18

2-(3-cyanophenyl)-4-phenyl-4-(4-trifluoromethylphenyl)-2-imidazoline

Mass spectrum(ESI): 392.1

EXAMPLE 5-19

2-(3-cyanophenyl)-4-(3-methoxyphenyl)-4-phenyl-2-imidazoline

Mass spectrum(ESI): 354.1

EXAMPLE 5-20

2-(3-cyanophenyl)-4-(3,4-dimethylphenyl)-4-phenyl-2-imidazoline

Mass spectrum(ESI): 352.1

EXAMPLE 5-21

2-(3-cyanophenyl)-4-(4-fluorophenyl)-4-(3-vinylphenyl)-2-imidazoline

Mass spectrum(ESI): 368.1

EXAMPLE 5-22

2-(3-cyanophenyl)-4-(2-naphthyl)-4-(3-pyridyl)-2-imidazoline

Mass spectrum(ESI): 375.1

EXAMPLE 5-23

4-(3-bromophenyl)-2-(3-cyanophenyl)-4-(4-fluorophenyl)-2-imidazoline

Mass spectrum(ESI): 420.1

EXAMPLE 5-24

4-(2-chlorophenyl)-2-(3-cyanophenyl)-4-phenyl-2-imidazoline

Mass spectrum(ESI): 358.1

EXAMPLE 5-25

2-(3-cyanophenyl)-4-(4-fluorophenyl)-4-(6-quinolyl)-2-imidazoline

Mass spectrum(ESI): 393.1

EXAMPLE 5-26

2-(3-cyanophenyl)-4-phenyl-4-(2-thienyl)-2-imidazoline

Mass spectrum(ESI): 330.3

EXAMPLE 5-27

2-(3-cyanophenyl)-4-(4-dimethylaminophenyl)-4-phenyl-2-imidazoline

Melting point: 210–213° C.

EXAMPLE 5-28

2-(3-cyanophenyl)-4-(4-fluorophenyl)-4-(3-pyridyl)-2-imidazoline

Mass spectrum(ESI): 343.0

EXAMPLE 5-29

2-(3-cyanophenyl)-4-(4-formylphenyl)-4-phenyl-2-imidazoline

Mass spectrum(ESI): 352.2

EXAMPLE 5-30

2-(3-cyanophenyl)-4-(4-fluorophenyl)-4-(2-thienyl)-2-imidazoline

Mass spectrum(ESI): 348.1

EXAMPLE 5-31

4,4-diphenyl-2-pyrazinyl-2-imidazoline

Melting point: 183–184° C.

EXAMPLE 5-32

2-(3-cyanophenyl)-4,4-bis(4-methoxyphenyl)-2-imidazoline

Mass spectrum(ESI): 384.1

EXAMPLE 5-33

2-(3-cyanophenyl)-4-(4-fluorophenyl)-4-(3-formylphenyl)-2-imidazoline

Mass spectrum(ESI): 370.1

EXAMPLE 5-34

4,4-bis(4-fluorophenyl)-2-(3-methylsulfonylphenyl)-2-imidazoline

Melting point: 209–212° C.

EXAMPLE 5-35

4,4-bis(4-fluorophenyl)-2-(3-formylphenyl)-2-imidazoline

Mass spectrum(ESI): 363.1

EXAMPLE 5-36

2-(3-cyanophenyl)-4-(2-methylphenyl)-4-phenyl-2-imidazoline

Mass spectrum(ESI): 338.1

EXAMPLE 5-37

2-(3-cyanophenyl)-4-(4-fluorophenyl)-4-(3-hydroxymethylphenyl)-2-imidazoline

Mass spectrum(ESI): 372.1

EXAMPLE 5-38

2-(3-cyanophenyl)-4-(4-fluorophenyl)-4-(1,2,3,4-tetrahydro-1,5-naphthyridin-7-yl)-2-imidazoline Mass spectrum(ESI): 398.1

EXAMPLE 5-39

2-(3-cyanophenyl)-4-(2-fluorophenyl)-4-(3-pyridyl)-2-imidazoline

Mass spectrum(ESI): 343.0

EXAMPLE 5-40

4-(4-biphenylyl)-2-(3-cyanophenyl)-4-phenyl-2-imidazoline

Mass spectrum(ESI): 400.3

EXAMPLE 5-41

2-(3-cyanophenyl)-4-(2-methoxyphenyl)-4-phenyl-2-imidazoline

Mass spectrum(ESI): 354.0

EXAMPLE 5-42

2-(3-cyanophenyl)-4-cyclohexyl-4-phenyl-2-imidazoline

Melting point: 151–152° C.

EXAMPLE 5-43

2-(3-cyanophenyl)-4-(4-fluorophenyl)-4-(4-pyridyl)-2-imidazoline

Mass spectrum(ESI): 343.0

EXAMPLE 5-44

4,4-bis(4-fluorophenyl)-2-(5-pyrimidinyl)-2-imidazoline

Mass spectrum(ESI): 337.0

EXAMPLE 5-45

2-(3-cyanophenyl)-4-cyclopentyl-4-phenyl-2-imidazoline

Mass spectrum(ESI): 316.2

EXAMPLE 5-46

2-(3-cyanophenyl)-4-cyclobutyl-4-phenyl-2-imidazoline

Melting point: 117–118° C.

EXAMPLE 5-47

4,4-bis(4-fluorophenyl)-2-(3-pyridazinyl)-2-imidazoline

Mass spectrum(ESI): 337.0

EXAMPLE 5-48

4-(4-fluorophenyl)-5-methyl-2-pyrazinyl-4-(3-quinolyl)-2-imidazoline $^1$HNMR(400 MHz, CD$_3$OD,δppm): 0.90(3H,d,J=6.4 Hz), 4.97–5.08(1H,m), 7.06–7.16(2H,m), 7.32–7.38 and 7.57–7.66(3H,m), 7.72–7.80(1H,m), 7.86–8.04(2H,m), 8.31 (0.8H,s), 8.51(0.2H,s), 8.64(0.8H,s), 8.66–8.76(2H,m), 8.88 (0.2H,s), 9.34(0.2H,s), 9.39(0.8H,s)

EXAMPLE 5-49

The Optical Active (5S)-4-(4-fluorophenyl)-4-(6-fluoro-3-pyridyl)-2-(3-methylsulfonylphenyl)-5-methyl-2-imidazoline, Wherein the Starting Material is the Diamine Described in Reference Example 5-1

$^1$HNMR(300 MHz, CDCl$_3$,δppm): 0.90(3H,d,J=6.3 Hz), 3.10(3H,s), 4.72–4.74(1H,m), 5.10–5.40(1H,brs), 7.00–8.37 (11H,m)

$[\alpha]_D^{25}$: −263.3°(c0.9,CHCl$_3$)

EXAMPLE 5-50

The Optical Active (5S)-2-(5-cyano-3-pyridyl)-4-(4-fluorophenyl)-4-(6-fluoro-3-pyridyl)-5-methyl-2-imidazoline, Wherein the Starting Material is the Diamine Described in Reference Example 5-1

$^1$HNMR(300 MHz, CDCl$_3$,δppm): 0.90(3H,d,J=6.3 Hz), 4.75(1H,q,J=6.3), 5.38(1H,s), 6.89(1H,dd,J=2.9 Hz,8.6 Hz), 7.03(2H,t,J=8.6 Hz), 7.20–7.30(2H,m), 7.89(1H,dt,J=2.2 Hz,7.9 Hz), 8.34(1H,s), 8.50–8.60(1H,m), 8.96(1H,d,J=2.0 Hz), 9.23(1H,d,J=2.0 Hz)

$[\alpha]_D^{25}$: −307.6°(c1.0,MeOH)

EXAMPLE 6

Production of the Optical Active (5S)-2-(2-cyano-4-pyridyl)-4-(4-fluorophenyl)-4-(6-fluoro-3-pyridyl)-5-methyl-2-imidazoline hydrochloride

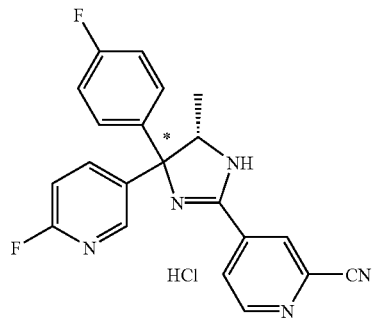

To a solution of 4-cyanopyridine N-oxide (100 mg) in methanol (4 mL) were added sodium methoxide (13.5 mg), and the mixture was stirred at room temperature for 24 hrs. To the reaction mixture was added methanesulfonic acid (104 mg), and the reaction mixture was stirred at room temperature for an additional 10 minutes. To the 3.5 ml of this solution was added to the solution (2 mL) of (2S)-1-(4-fluorophenyl)-1-(6-fluoro-3-pyridyl)-1,2-propanediamine described in Reference Example 5-1, and the mixture was stirred at room temperature for 15 hrs. After concentrating the reaction mixture in vacuo, the obtained residue was dissolved in ethyl acetate, washed with saturated sodium hydrogen carbonate aqueous solution and saturated sodium chloride aqueous solution in this order, and dried over anhydrous sodium sulfate. Sodium sulfate was removed by filtration, and the organic solvent was evaporated in vacuo. The obtained residue was purified by silica gel column chromatography (C-300; chloroform:methanol=9:1) to give 2-(1-oxido-pyridin-4-yl)-4-(4-fluorophenyl)-4-(6-fluoro-3-pyridyl)-5-methyl-2-imidazoline (172 mg) as colorless oil. To the solution (5 ml) of the obtained N-oxide compound in acetonitrile was added trimethylsilylcyanide (140 mg) and triethylamine (142 mg), and the mixture was stirred at 90° C. for 17 hrs. To the mixture was added trimethylsilylcyanide (140 mg) and triethylamine (142 mg), and the mixture was stirred at 90° C. for 2 hrs, and concentrated in vacuo. The obtained residue was dissolved in chloroform, washed with saturated sodium hydrogen carbonate aqueous solution, water and saturated sodium chloride aqueous solution in this order, and dried over anhydrous sodium sulfate. Sodium sulfate was removed by filtration, and the organic solvent was evaporated in vacuo. The obtained residue was purified by silica gel column chromatography (C-300; hexane:ethyl acetate=1:1) and treated with 4N hydrogen chloride-ethyl acetate solution to give the title compound (108 mg).

$^1$HNMR(300 MHz,DMSO-d$_6$,δppm): 0.95(3H,d,J=6.6 Hz), 5.40(1H,brs), 7.23–7.36(5H,m), 8.22–8.28(1H,m), 8.47(1H,d,J=4.8 Hz), 8.58(1H,s), 8.83(1H,s), 9.12(1H,d,J=5.1 Hz)

$[\alpha]_D^{25}$: −309.7°(c1.0,MeOH)

By applying the method described in Example 6, corresponding diamine and 4-cyanopyridine N-oxide were subjected to the ring condensation reaction, followed by reacting with trimethylsilylcyanide, optionally the protecting group was removed by the method similar to the method described in Example 5 to give the following compounds.

EXAMPLE 6-1

(5R)-2-(2-cyano-4-pyridyl)-4,4-bis(4-fluorophenyl)-5-hydroxymethyl-2-imidazoline $^1$HNMR(300 MHz, CDCl$_3$,δppm): 3.09(1H,br), 3.29(1H,dd,J=4.4 Hz,10.6 Hz), 4.74(0.9H,brs), 5.02(0.1H,d,J=5.1 Hz), 5.74(1H,brs), 6.97–7.05(4H,m), 7.19–7.23(2H,m), 7.42–7.47(2H,m), 7.92(1H,d,J=4.1 Hz), 8.21(1H,s), 8.81(1H,d,J=5.5 Hz)

EXAMPLE 6-2

(5S)-2-(2-cyano-4-pyridyl)-4,4-bis(4-fluorophenyl)-5-methyl-2-imidazoline $^1$HNMR(300 MHz, CDCl$_3$,δppm): 0.85–0.97(3H,m), 4.70–4.78(1H for major,m), 4.92–5.00(1H for minor,m), 5.02(1H for major,brs), 5.32(1H for minor,brs), 6.92–7.07(4H,m), 7.10–7.53(4H,m), 7.87–7.92(1H,m), 8.10–8.20(1H,m), 8.77–8.83(1H,m)

$[\alpha]_D^{25}$: −300.0°(c1.0,CHCl$_3$)

EXAMPLE 6-3

The Optical Active (5S)-2-(2-cyano-4-pyridyl)-4-(4-fluorophenyl)-4-(2-fluoro-4-pyridyl)-5-methyl-2-imidazoline, Wherein the Starting Material is the Diamine Described in Reference Example 7

$^1$HNMR(300 MHz, CDCl$_3$,δppm): 0.93(3H,d,J=6.6 Hz), 4.71(1H,q,J=6.6 Hz), 5.30(1H,brs), 6.98–7.12(3H,m), 7.15–7.24(3H,m), 7.94(1H,dd,J=5.0 Hz,1.6 Hz), 8.15–8.22(2H,m), 8.83(1H,d,J=5.0 Hz)

$[\alpha]_D^{25}$: −260.0°(c1.0,CHCl$_3$)

EXAMPLE 6-4

(5S)-2-(2-cyano-4-pyridyl)-4,4-bis(6-fluoro-3-pyridyl)-5-methyl-2-imidazoline hydrochloride $^1$HNMR(400 MHz,CD$_3$OD,δppm): 1.15(3H,d,J=6.4 Hz), 5.51(1H,q,J=6.4 Hz), 7.19(1H,dd,J=8.8 Hz,2.8 Hz), 7.24(1H,dd,J=8.8 Hz,2.8 Hz), 7.84–7.89(1H,m), 8.09–8.12(1H,m), 8.17(1H,dd,J=5.2 Hz,1.6 Hz), 8.23(1H,d,J=2.4 Hz), 8.40(1H,d,J=1.6 Hz), 8.45(1H,d,J=2.4 Hz), 9.07(1H,d,J=5.2 Hz)

$[\alpha]_D^{25}$: −239.5°(c0.8,MeOH)

EXAMPLE 7

Production of 4,4-bis(4-fluorophenyl)-5-methyl-2-pyrazinyl-2-imidazoline

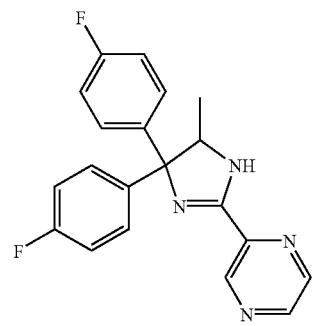

1,1-bis(4-fluorophenyl)-1,2-propanediamine (94 mg) and pyrazinecarboxylic acid (53 mg) was dissolved in pyridine (1 mL), and to the solution was added 1-(3-dimethylaminopropyl)-3-ethylcarbodiimide(103 mg). The mixture was stirred at room temperature for 24 hrs. The reaction mixture was concentrated, and the obtained residue was dissolved in chloroform, followed by washing with saturated sodium hydrogen carbonate aqueous solution. The aqueous layer was extracted with chloroform twice, and the combined chloroform layers were dried over magnesium sulfate. After evaporating the solvent in vacuo, the obtained residue was purified by silica gel column chromatography (C-300; hexane:ethyl acetate=1:1→1:3) to give N-[2-amino-2,2-bis(4-fluorophenyl)-1-methylethyl]-2-pyrazinecarboxamide(112 mg) as the mixture with pyrazinecarboxylic acid methyl ester. The mixture was dissolved in methanol (1 mL), and to the solution was added 2N sodium hydroxide aqueous solution (0.5 mL), and the solution was stirred at room temperature for one hr. The reaction mixture was diluted with chloroform, followed by washing with water. The aqueous layer was extracted with chloroform twice, and the combined chloroform layers were dried over anhydrous magnesium sulfate. The solvent was evaporated in vacuo to give the pure amide compound (95 mg).

To a solution of the above-mentioned amide compound (157 mg) in benzene (4 mL) was added phosphorus pentachloride (266 mg), and the mixture was stirred at 50° C. for 3 days. After cooling to room temperature, to the reaction mixture was added 2N sodium hydroxide aqueous solution (4 ml), and the reaction mixture was stirred for an additional 30 minutes. The obtained mixture was extracted with chloroform thrice, and dried over anhydrous magnesium sulfate. The solvent was evaporated in vacuo, and the obtained residue was purified by silica gel column chromatography (C-300; hexane:ethyl acetate=1:1→1:2) to give the objective compound (100 mg).

Mass spectrum(ESI): 351.2
$^1$HNMR(300 MHz, CDCl$_3$,δppm): 0.90(2.1H,d,J=6.4 Hz), 0.99(0.9H,d,J=6.9 Hz), 4.70(0.7H,q,J=6.4 Hz), 5.03 (0.3H,q,J=6.9 Hz), 5.97–6.00(0.7H,m), 6.43–6.45(0.3H,m), 6.95–7.08(4H,m), 7.25–7.37(2.6H,m), 7.51–7.56(1.4H,m), 8.53–8.55(1H,m), 8.66(1H,d,J=2.5 Hz), 9.42(0.3H,d,J=1.7 Hz), 9.54(0.7H,d,J=1.5 Hz)

By applying the method described in Example 7, corresponding diamine and carboxylic acid were cyclized and condensed, followed by optionally deprotecting by the method similar to the method described in Example 5 to give the following compounds.

EXAMPLE 7-1

4,4-bis(4-fluorophenyl)-5-hydroxymethyl-2-pyrazinyl-2-imidazoline

Mass spectrum(ESI): 367.1

---

$^1$HNMR (300 MHz , CDCl$_3$, δ ppm): 3.12,
3.30 [2H(3.12,t,J = 9.6 Hz), (3.30,m)], 4.66,
5.08 [1H(4.66,dd,J = 3.9,8.7 Hz), (5.08,m)], 6.55,
6.60 [1H(6.55,s), (6.60,s)], 7.00(4H,m), 7.14(2H,m), 7.35,
7.54 [2H(7.35,dd,J = 4.5 Hz,5.7 Hz), (3.30,dd,J = 5.4 Hz,8.1 Hz)],
8.54 (1H,d,J = 2.0 Hz), 8.66(1H,d,J = 2.0 Hz),
9.43,9.52 [1H(9.43,s), (9.52,s)]

---

EXAMPLE 7-2

5-ethyl-4,4-bis(4-fluorophenyl)-2-pyrazinyl-2-imidazoline $^1$HNMR(300 MHz, CDCl$_3$,δppm): 0.95–1.35(3H,m), 4.36–4.45(1H for major,m), 4.73–4.79(1H for minor,m), 6.21–6.29(1H for major,br), 6.42–6.44(1H for minor,br), 6.90–7.18(4H,m), 7.12–7.21(2H,m), 7.29–7.60(2H,m), 8.50–8.58(1H,m), 8.61–8.68(1H,m), 9.44(1H,d,J=1.5 Hz for minor), 9.55(1H,d,J=1.5 Hz for major)

EXAMPLE 7-3

4,4-bis(4-fluorophenyl)-5-propyl-2-pyrazinyl-2-imidazoline hydrochloride $^1$HNMR(300 MHz,CD$_3$OD,δppm): 0.87(3H,t,J=7.0 Hz), 1.14–1.66(4H,m), 5.10–5.20(1H,m), 7.10–7.30(6H,m), 7.54–7.65(2H,m), 8.87–8.94(1H,m), 8.95–9.00(1H,m), 9.36–9.40(1H,br)

EXAMPLE 8

Production of 4,4-bis(4-fluorophenyl)-2-(4-isothiazolyl)-2-imidazoline

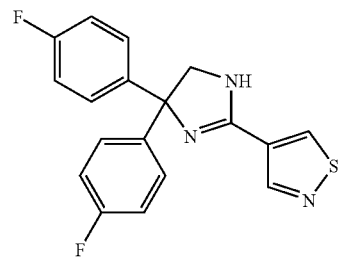

While stirring a solution of 1,1-(4-fluorophenyl)-1,2-ethanediamine (330 mg) in anhydrous toluene(8 mL) at 0° C., 0.98M trimethylaluminum hexane solution (1.36 mL) was dropwise added to the solution under nitrogen, and the mixture was stirred at 0° C. for 5 minutes. 4-isothiazolecarboxylic acid methyl ester(120 mg) was dissolved in toluene(1 mL), and the solution was added to the above reaction mixture. Then the mixture was heated at 110° C. for 3 hours. After the reaction mixture was cooled, sodium sulfate decahydrate was added to the reaction mixture, and then the mixture was stirred at room temperature for 15 minutes. Anhydrous sodium sulfate was added to the reaction mixture, and the mixture was stirred for an additional 20 minutes. The obtained mixture was filtered through celite, and the filtrate was concentrated in vacuo. The obtained residue was purified by silica gel column chromatography (C-300; hexane:ethyl acetate=1:1) to give the objective compound(116 mg).

Mass spectrum(ESI): 342.0
$^1$HNMR(300 MHz, CDCl$_3$,δppm): 4.26(2H,brs), 6.97–7.07(4H,m),7.32–7.37(4H,m),8.93(1H,s),9.03(1H,s)

EXAMPLE 9

Production of 2-(3-pyridyl)-4,4-bis(4-fluorophenyl)-2-imidazoline hydrochloride

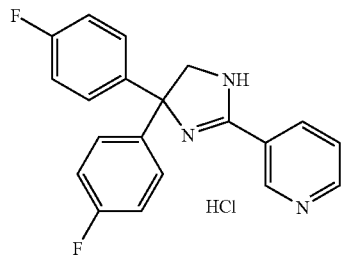

While stirring a solution of 1,1-bis(4-fluorophenyl)-1,2-ethanediamine (300 mg) in anhydrous toluene(3 mL) at 0° C., a solution of 0.98M trimethylaluminum in hexane (1.23 mL) was dropwise added to the solution under nitrogen, and the mixture was stirred at room temperature for 15 minutes. Methyl nicotinate (103 mg) was dissolved in toluene 1 mL, and the solution was added to the above reaction mixture. Then the mixture was heated at 80° C. for 5 hours. After the reaction mixture was cooled, sodium sulfate decahydrate was added to the reaction mixture, and the mixture was stirred at room temperature for 15 minutes. Anhydrous sodium sulfate was added to the reaction mixture, and the mixture was stirred for an additional 20 minutes. The obtained mixture was filtered through celite, and the filtrate was concentrated in vacuo. The obtained residue was purified by silica gel column chromatography (C-300; hexane:ethyl acetate=1:2), treated with 4N hydrogen chloride-ethyl acetate solution and dried in vacuo to give the objective compound(111 mg).

Melting point: 172–176° C.

$^1$HNMR(300 MHz, DMSO-$d_6$,δppm): 4.70(2H,s), 7.24–7.33(4H,m),7.53–7.60(4H,m),7.72–7.76(1H,m), 8.60–8.65(1H,m),8.93–8.95(1H,m),9.36(1H,s),11.61(1H,s), 12.29(1H,s)

By applying the methods described in above-mentioned Example 8 and 9, corresponding diamine and ester were reacted to give the following compounds.

EXAMPLE 9-1

2-(3-chlorophenyl)-4,4-bis(4-fluorophenyl)-2-imidazoline hydrochloride

Mass spectrum(ESI): 369.0

EXAMPLE 9-2

4,4-bis(4-fluorophenyl)-2-(3-trifluoromethylphenyl)-2-imidazoline

Mass spectrum(ESI): 403.1

EXAMPLE 9-3

2-(3-fluorophenyl)-4,4-bis(4-fluorophenyl)-2-imidazoline

Mass spectrum(ESI): 353.1

EXAMPLE 9-4

4,4-bis(4-fluorophenyl)-2-(3-trifluoromethoxyphenyl)-2-imidazoline

Melting point: 114–117° C.

EXAMPLE 9-5

4,4-bis(4-fluorophenyl)-2-(5-thiazolyl)-2-imidazoline

Mass spectrum(ESI): 342.0

EXAMPLE 9-6

4,4-bis(4-fluorophenyl)-2-(3-methylphenyl)-2-imidazoline

Melting point: 148–149° C.

EXAMPLE 9-7

4,4-bis(4-fluorophenyl)-2-(2-thienyl)-2-imidazoline

Melting point: 156–160° C.

EXAMPLE 9-8

2-(5-bromo-3-pyridyl)-4,4-bis(4-fluorophenyl)-2-imidazoline

Mass spectrum(ESI): 414.0/416.0

EXAMPLE 9-9

2-(3-bromophenyl)-4,4-bis(4-fluorophenyl)-2-imidazoline

Mass spectrum(ESI): 412.9/415.0

EXAMPLE 9-10

4,4-bis(4-fluorophenyl)-2-(3-thienyl)-2-imidazoline

Melting point: 160–163° C.

EXAMPLE 10

Production of 2-(4-cyano-2-pyridyl)-4,4-bis(4-fluorophenyl)-2-imidazoline

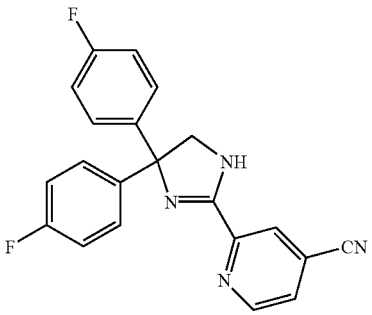

The mixture of 1,1-bis(4-fluorophenyl)-1,2-ethanediamine(153 mg) and 4-cyano-2-ethoxycarbonylpyridine(95 mg) was stirred at 180° C. for 2 hours. The obtained oily compound was purified by silica gel column chromatography (C-300; hexane:ethyl acetate=3:2) to give the objective compound (103 mg).

Melting point: 206–208° C.

EXAMPLE 11

Production of the Optical Active (5S)-2-(3-cyanophenyl)-4-(4-fluorophenyl)-4-(6-fluoro-3-pyridyl)-5-methyl-2-imidazoline

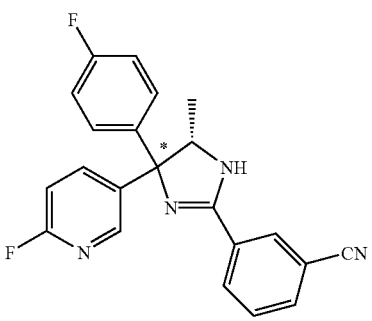

3-Cyanobenzoic acid (84 mg), triethylamine (159 μL) and 2-chloro-1,3-dimethylimidazolinium chloride-dichloromethane 25% solution (212 μL) were added to a solution of (2S)-1-(4-fluorophenyl)-1-(6-fluoro-3-pyridyl)-1,2-propanediamine(100 mg) described in Reference Example 5-1 in chloroform(3 mL) in this order at 0° C. Then temperature of the mixture was raised to room temperature, and the mixture was stirred for 15 minutes. Saturated sodium hydrogen carbonate aqueous solution was added to the reaction mixture, and then the mixture was extracted with ethyl acetate. The organic layer was washed with saturated sodium chloride aqueous solution and dried over anhydrous sodium sulfate. Sodium sulfate was removed by filtration, and the organic solvent was evaporated in vacuo. The obtained crude product was stirred at 130° C. for 15 hours. The obtained oil was purified by silica gel column chromatography (C-300; hexane:ethyl acetate=1:1) to give the objective compound (140 mg).

$^1$HNMR(300 MHz, CDCl$_3$,δppm): 0.89(3H,d,J=6.5 Hz), 4.66–4.74 (1H,m),5.10(1H,brs),6.85–6.90(1H,m),7.02(2H,t, J=8.4 Hz),7.20–7.30(2H,m),7.57(1H,t,J=7.9 Hz),7.74–7.79 (1H,m),7.85–7.95(1H,m),8.07–8.12(1H,m),8.19(1H,s), 8.37–8.42(1H,m)

$[α]_D^{25}$: −295.6°(c1.0, CHCl$_3$)

By applying the method described in above-mentioned Example 11, corresponding diamine and carboxylic acid were cyclized, and the reactant was optionally deprotected by the method similar to the method described in Example 7 to give the following compounds.

EXAMPLE 11-1

2-(3-cyanophenyl)-4,4-bis(4-fluorophenyl)-5-(1-hydroxyethyl)-2-imidazoline $^1$HNMR(300 MHz, CDCl$_3$,δppm): 1.08(3H,d,J=6.3 Hz), 3.54–3.72 (1H,m),4.47–4.55(1H for major,m),4.85–4.90(1H for minor,m),5.17(1H for major,brs),5.48(1H for minor,brs), 6.93–7.10(4H,m),7.15–7.28(2H,m),7.22–7.60(2H,m), 7.65–7.80(2H,m),8.07–8.25(2H,m)

EXAMPLE 11-2

The Optical Active (5S)-2-(3-cyanophenyl)-4-(4-fluorophenyl)-4-(2-fluoro-4-pyridyl)-5-methyl-2-imidazoline, Wherein the Starting Material is the Diamine Described in Reference Example 7

$^1$HNMR(300 MHz, CDCl$_3$,δppm): 0.92(3H for major,d, J=6.6 Hz),1.02(3H for minor,d,J=6.9 Hz,),4.66(1H for major, q,J=6.6 Hz),4.87(1H for minor,q,J=6.9 Hz),5.22(1H for major,brs),5.68(1H for minor,brs),6.97–7.09(3H,m),7.12 (1H,s),7.15–7.35(3H,m),7.54–7.61(1H,m),7.75–7.80(1H, m),8.08–8.23(3H,m)

$[α]_D^{25}$: −291.6°(c1.0,CHCl$_3$)

EXAMPLE 11-3

The Optical Active (5S)-2-(3-cyanophenyl)-4-(4-fluorophenyl)-4-(2-fluoro-4-pyridyl)-5-methyl-2-imidazoline, Wherein the Starting Material is the Diamine Described in Reference Example 8

$^1$HNMR(300 MHz, CDCl$_3$,δppm): 0.98(3H,d,J=6.6 Hz), 4.74(1H,q,J=6.6 Hz),4.98–5.08(1H,m),5.07(1H for major, brs),5.30(1H for minor,brs),6.91–7.12(4H,m),7.47–7.63 (3H,m),7.78(1H,d,J=7.8 Hz),8.08–8.21(3H,m)

$[α]_D^{25}$: −258.97°(c0.16,CHCl$_3$)

EXAMPLE 12

Production of the Optical Active (5S)-4-(4-fluorophenyl)-4-(6-fluoro-3-pyridyl)-5-methyl-2-(1,2,5-thiadiazol-3-yl)-2-imidazoline

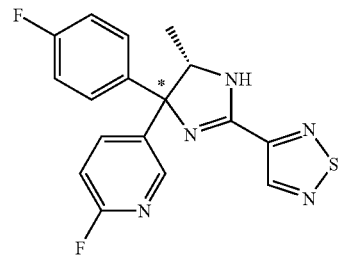

Triethylamine(23 mg) and 1,1'-carbonyldiimidazole(37 mg) were added to a solution of 1,2,5-thiadiazole-3-carboxylic acid(30 mg) in tetrahydrofuran(3 mL) in this order, and the mixture was stirred at room temperature for one hour. A solution of (2S)-1-(4-fluorophenyl)-1-(6-fluoro-3-pyridyl)-1,2-propanediamine (50 mg) described in Reference Example 5-1 in tetrahydrofuran (1 mL) was added to the above reaction mixture, and the resultant mixture was stirred at room temperature for 17 hours. The reaction mixture was concentrated in vacuo, and then the obtained residue was dissolved in ethyl acetate. Then the solution was washed with water and saturated sodium chloride aqueous solution in this order, and dried over anhydrous sodium sulfate. Sodium sulfate was removed by filtration, and the organic solvent was evaporated in vacuo. The obtained crude product was dissolved in toluene (0.5 mL). Ytterbium triflomethanesulfonate (12 mg) was added to the solution, and then the mixture was stirred at 100° C. for 10 hours. The reaction mixture was diluted with ethyl acetate, and the dilution was washed with saturated sodium hydrogen carbonate aqueous solution, water and saturated sodium chloride aqueous solution in this order. The mixture was dried over anhydrous sodium sulfate. Sodium sulfate was removed by filtration, and the organic solvent was evaporated in vacuo. The obtained residue was purified by silica gel column chromatography (C-300; hexane:ethyl acetate=2:3) to give the objective compound (37 mg) as colorless oil.

$^1$HNMR(300 MHz, CDCl$_3$,δppm): 0.88,0.98(3.0H,d, J=6.6 Hz),4.70,4.98(1.0H,q,J=6.6 Hz),5.74,6.06(1H,brs), 6.88(1H,dd,J=3.0 Hz,8.7 Hz),6.99–7.05(2H,m),7.24–7.29 (2H,m),7.74–7.93(2H,m),8.26,8.40(1H,d,J=1.8 Hz),9.15, 9.19(1H,s)

$[α]_D^{25}$: −369.2°(c1.0,MeOH)

By applying the method described in above-mentioned Example 12, corresponding diamine and carboxylic acid were cyclized and condensed, and then the reactant was optionally deprotected by the method similar to the method described in Example 7 to give the following compounds.

EXAMPLE 12-1

(5R)-4,4-bis(4-fluorophenyl)-5-hydroxymethyl-2-(6-hydroxy-2-pyridyl)-2-imidazoline $^1$HNMR(300 MHz, CDCl$_3$,δppm): 3.13(2H,ds,J=6.6 Hz), 4.75(1H, br),6.68(1H,d,J=8.1 Hz),6.85(1H,d,J=6.0 Ha), 6.95–7.00(4H,m),7.21–7.25(4H,m),7.39–7.53(3H,m)
$[\alpha]_D^{25}$: −269.6°(c0.5,MeOH)

EXAMPLE 12-2

(5S)-4,4-bis(4-fluorophenyl)-2-(6-hydroxy-2-pyridyl)-5-methyl-2-imidazoline $^1$HNMR(300 MHz, CDCl$_3$,δppm): 0.85–0.95(3H,m), 4.68–4.95(1H,m),5.61(1H,brs),6.63–6.75(2H,m),6.90–7.07(4H,m),7.10–7.20(2H,m),7.30–7.51(3H,m)
$[\alpha]_D^{25}$: −305.4°(c0.7,CHCl$_3$)

EXAMPLE 12-3

The Optical Active (5S)-2-(2-chloro-4-pyridyl)-4-(4-fluorophenyl)-4-(6-fluoro-3-pyridyl)-5-methyl-2-imidazoline, Wherein the Starting Material is the Diamine Described in Reference Example 5-1

$^1$HNMR(300 MHz, CDCl$_3$,δppm): 0.88(3H,d,J=6.6 Hz), 4.72–4.84 (1H,m),5.05–5.15(1H,brs),6.90–6.98(1H,m), 7.05–7.15(2H,m),7.25–7.30(2H,m),7.65–7.72(1H,m), 7.82–7.88(1H,m),7.90–7.98(1H, m),8.41–8.45(1H,m), 8.48–8.51(1H,m)
$[\alpha]_D^{25}$: −294.0°(c0.5,MeOH)

EXAMPLE 12-4

The Optical Active (5S)-4-(4-fluorophenyl)-4-(6-fluoro-3-pyridyl)-2-(6-hydroxy-2-pyridyl)-5-methyl-2-imidazoline, Wherein the Starting Material is the Diamine Described in Reference Example 5-1

$^1$HNMR(300 MHz, CDCl$_3$,δppm): 0.87(3H,d.J=6.5 Hz), 4.70–4.80 (1H,m),5.65–5.85(1H,br),6.65–6.80(2H,m), 6.86–6.92(1H,m),6.98–7.06(2H,m),7.15–7.24(2H,m), 7.45–7.52(1H,m),7.80–7.88(1H,m),8.33(1H,s)
$[\alpha]_D^{25}$: −258.8°(c0.7,MeOH)

EXAMPLE 12-5

(5S)-2-(3-cyanophenyl)-4,4-bis(6-fluoro-3-pyridyl)-5-methyl-2-imidazoline $^1$HNMR(300 MHz, CDCl$_3$,δppm): 0.96(3H,d,J=6.6 Hz), 4.75(1H,q,J=6.6 Hz),5.16(1H,s),6.89–6.93(2H,m), 7.55–7.95(4H,m),8.08–8.20(3H,m),8.41(1H,s)
$[\alpha]_D^{25}$: −256.1°(c0.4,MeOH)

EXAMPLE 12-6

The Optical Active (5R)-2-(3-cyanophenyl)-4-(4-fluorophenyl)-4-(6-fluoro-3-pyridyl)-5-hydroxymethyl-2-imidazoline, Wherein the Starting Material is the Diamine Described in Reference Example 6-1

$^1$HNMR(300 MHz, CDCl$_3$,δppm): 3.10(1H,br),3.24(1H, d,J=4.2 Hz,10.5 Hz),4.67(1H,br),5.34,5,83(1H,br),6.88(1H, dd,J=3.3 Hz,9.0 Hz),7.02(2H,t,J=8.7 Hz),7.28(2H,t,J=8.7 Hz),7.57(1H,t,J=8.1 Hz),7.77(1H,d,J=7.8 Hz),7.88(1H,td, J=2.7 Hz,8.3 Hz),8.10(1H,d, J=8.1 Hz),8.22(1H,s),8.39(1H, d,J=0.9 Hz)
$[\alpha]_D^{25}$: −268.6°(c1.0,CHCl$_3$)

EXAMPLE 12-7

The Optical Active (5S)-2-(3-cyanophenyl)-4-(4-fluorophenyl)-5-methyl-4-(1,5-naphtyridin-3-yl)-2-imidazoline, Wherein the Starting Material is the Diamine Described in Reference Example 7-1

$^1$HNMR(300 MHz, CDCl$_3$,δppm): 0.96(3H,d,J=5.9 Hz), 4.80–5.00 (1H,m),5.42(1H,brs),7.03(2H,t,J=8.6 Hz), 7.20–7.40(2H,m),7.53 (1H,t,J=8.6 Hz),7.63(1H,dd,J=4.2 Hz,8.6 Hz),7.70 –7.80(1H,m),8.10–8.20(1H,m),8.20(1H,s), 8.38(1H,d,J=8.6 Hz),8.50(1H,d,J=1.6 Hz),8.97(1H,dd,J=1.6 Hz,4.2 Hz),9.08(1H,s)
$[\alpha]_D^{25}$: −363.6°(c0.5,CHCl$_3$)

EXAMPLE 12-8

The Optical Active (5S)-2-(3-cyanophenyl)-4-(6-fluoro-3-pyridyl)-4-(4-fluorophenyl)-5-methyl-2-imidazoline hydrochloride, Wherein the Starting Material is the Diamine Described in Reference Example 5-2

$^1$HNMR(300 MHz,CD$_3$OD,δppm): 1.24(3H,d,J=7.1 Hz), 5.42(1H,q,J=7.1 Hz),7.15(1H,dd,J=8.5 Hz,2.6 Hz),7.27(2H, dd,J=8.9 Hz,8.5 Hz),7.60(2H,dd,J=8.9 Hz,4.9 Hz), 7.78–7.92(2H,m),8.13–8.29(3H,m),8.39–8.40(1H,m)
$[\alpha]_D^{25}$: −283.6°(c0.5,MeOH)

EXAMPLE 12-9

The Optical Active (5S)-2-(3-cyanophenyl)-4-(4-fluorophenyl)-5-methyl-4-(1,5-naphtyridin-3-yl)-2-imidazoline, Wherein the Starting Material is the Diamine Described in Reference Example 8-1

$^1$HNMR(300 MHz, CDCl$_3$,δppm): 1.02(3H,d,J=6.6 Hz), 4.82–4.91 (1H,m),5.09–5.12(1H,br),7.03–7.13(2H,m), 7.55–7.70(4H,m),7.79(1H,dt,J=7.8 Hz,1.3 Hz),8.19(1H,d, J=7.9 Hz),8.25(1H,s),8.34–8.41(2H, m),8.78(1H,d,J=2.5 Hz),8.96(1H,dd,J=4.2 Hz,1.6 Hz)

EXAMPLE 12-10

(5S)-2-(5-cyano-3-pyridyl)-4,4-bis(6-fluoro-3-pyridyl)-5-methyl-2-imidazoline hydrochloride $^1$HNMR(400 MHz,CD$_3$OD,δppm): 1.15(3H,d,J=6.4 Hz), 5.49(1H,q,J=6.4 Hz),7.19(1H,dd,J=8.8 Hz,2.8 Hz),7.24(1H, dd,J=8.8 Hz,2.8 Hz),7.85–7.90(1H,m),8.09–8.14(1H,m), 8.24(1H,d,J=2.8 Hz),8.45(1H,d,J=2.8 Hz),8.77–8.78(1H, m),9.29(1H,d,J=2.0 Hz),9.35(1H,d, J=2.0 Hz)
$[\alpha]_D^{25}$: −252.0°(c0.1,MeOH)

EXAMPLE 13

Production of the Optical Active (5S)-2-(4-cyano-2-pyridyl)-4-(4-fluorophenyl)-4-(6-fluoro-3-pyridyl)-5-methyl-2-imidazoline

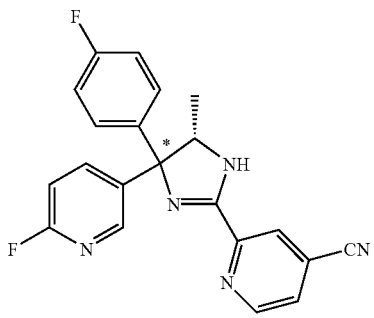

2,4-Dicyanopyridine(46.5 mg) and ytterbium trifluoromethanesulfonate (24 mg) were added to a solution of the optical active (2S)-1-(4-fluorophenyl)-1-(6-fluoro-3-pyridyl)-1,2-propanediamine(100 mg) described in Reference Example 5-1 in toluene(0.25 mL), and the mixture was stirred at 100° C. for 5 hours. The reaction mixture was diluted with ethyl acetate, washed with saturated sodium hydrogen carbonate aqueous solution, water and saturated sodium chloride aqueous solution in this order, and dried over anhydrous sodium sulfate. Sodium sulfate was removed by filtration, and the organic solvent was evaporated in vacuo. The obtained residue was purified by silica gel column chromatography (C-300; hexane:ethyl acetate=2:3) to give the objective compound (106 mg) as a white solid.

Melting point: 177–179° C.

$^1$HNMR(300 MHz, CDCl$_3$,δppm): 0.87,0.98(3.0H,d,J=6.7 Hz),4.73,4.98(1.0H,q,J=6.6 Hz),6.85–6.98(1.0H,m),6.99–7.06(2H,m),7.18–7.29(2H,m),7.61(1H,d,J=4.4 Hz),7.77–7.93(1H,m),8.25,8,39(1.0H,d,J=2.6 Hz),8.45,8.48(1H,s),8.76(1H,dd,J=0.9 Hz,5.1 Hz)

$[\alpha]_D^{25}$: –416.9°(c1.0,CHCl$_3$)

EXAMPLE 14

Production of (5R)-2-(4-cyano-2-pyridyl)-4,4-bis(4-fluorophenyl)-5-hydroxyethyl-2-imidazoline

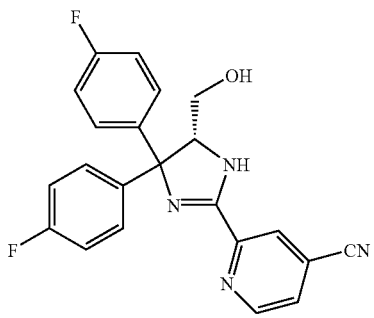

2,4-Dicyanopyridine (601 mg) and ytterbium trifluoromethanesulfonate (289 mg) were added to a solution of (2R)-1,1-bis(4-fluorophenyl)-3-(methoxymethoxy)-1,2-propanediamine(1.50 g) in toluene(30 mL), and the mixture was refluxed under stirring for 2 days. The reaction mixture was concentrated in vacuo, and then the residue was dissolved in tetrahydrofuran (20 mL). 6N Hydrochloric acid (10 mL) was added to the solution, and then the mixture was stirred at room temperature for 24 hours. The reaction mixture was concentrated in vacuo, and then the residue was purified by silica gel column chromatography (C-300; hexane:ethyl acetate=2:1) to give the objective compound (385 mg).

$^1$HNMR(200 MHz,CD$_3$OD,δppm): 3.15(2H,brs),4.71(1H,brs),7.02(2H,m),7.08(2H,m),7.23(2H,m),7.57(2H,m),7.83(1H,dd,J=3.0 Hz,10.0 Hz),8.46(1H,s),8.87(1H,d,J=10.0 Hz)

$[\alpha]_D^{25}$: –312.8°(c1.0,CHCl$_3$)

By applying the methods described in Example 13 and 14, corresponding diamine and cyanopyridine were cyclized, optionally followed by cleavage the protecting groups to give the following compounds.

EXAMPLE 14-1

2-(4-cyano-2-pyridyl)-4-(4-fluorophenyl)-4-(6-fluoro-3-pyridyl)-2-imidazoline $^1$HNMR(300 MHz, CDCl$_3$,δppm): 4.16–4.26(2H,m), 4.54–4.71(1H, m),6.20(0.8H,s),6.58(0.2H,s),6.86–8.78 (10H,m)

EXAMPLE 14-2

2-(4-cyano-2-pyridyl)-4-(4-fluorophenyl)-4-(2-fluoro-4-pyridyl)-2-imidazoline

Melting point: 169–171° C.

EXAMPLE 14-3

The Optical Active (5R)-2-(4-cyano-2-pyridyl)-4-(4-fluorophenyl)-4-(6-fluoro-3-pyridyl)-5-hydroxymethyl-2-imidazoline, Wherein the Starting Material is the Diamine Described in Reference Example 6-1

$^1$HNMR(400 MHz, CD$_3$OD,δppm): 3.17(2H,d,J=6.2 Hz), 4.76(1H,t, J=6.2 Hz),7.06(3H,m),7.28(2H,m),7.85(1H,d,J=4.8 Hz),8.12(1H,dd,J=2.8 Hz,7.6 Hz,7.6 Hz),8.43(1H,d,J=2.8 Hz),8.47(1H,s),8.88(1H,d,J=4.8 Hz)

$[\alpha]_D^{25}$: –304.7° (c0.6,CHCl$_3$)

EXAMPLE 14-4

The Optical Active (5S)-2-(6-cyano-2-pyridyl)-4-(4-fluorophenyl)-4-(6-fluoro-3-pyridyl)-5-methyl-2-imidazoline, Wherein the Starting Material is the Diamine Described in Reference Example 5-1

$^1$HNMR(300 MHz, CDCl$_3$,δppm): 0.88(2.5H,d,J=6.5 Hz),0.98(0.5H,d,J=6.8 Hz),4.68–4.78(0.8H,m),4.92–5.05 (0.2H,m),6.16(0.8H, brs),6.52(0.2H,brs),6.85–7.09(3H,m), 7.20–7.25(2H,m),7.72–8.00(3H,m),8.30–8.55(2H,m)

$[\alpha]_D^{25}$: –335.35° (c0.2,MeOH)

EXAMPLE 14-5

The Optical Active (5S)-2-(4-cyano-2-pyridyl)-4-(4-fluorophenyl)-4-(6-fluoro-3-pyridyl)-5-methyl-2-imidazoline (Epimer in 4th Position of Example 13 Compound), Wherein the Starting Material is the Diamine Described in Reference Example 5-2

¹HNMR(300 MHz, CDCl₃,δppm): 0.96(2.4H,d,J=6.5 Hz),1.01(0.6H,d,J=6.9 Hz),4.76(0.8H,q,J=6.5 Hz),5.07 (0.2H,q,J=6.9 Hz),6.14(0.8H,brs),6.54(0.2H,brs),6.84–6.91 (1H,m),7.00–7.10(2H,m),7.30–7.37(0.4H,m),7.48–7.56 (1.6H,m),7.60–7.71(2H,m),8.08(0.8H,d,J=2.6 Hz),8.15 (0.2H,d,J=2.6 Hz),8.45(0.2H,s),8.57(0.8H,s),8.74–8.78(1H,m)

$[\alpha]_D^{25}$: −291.0° (c0.8,MeOH)

EXAMPLE 14-6

The Optical Active (5S)-2-(4-cyano-2-pyridyl)-4-(4-fluorophenyl)-4-(2-fluoro-4-pyridyl)-5-methyl-2-imidazoline, Wherein the Starting Material is the Diamine Described in Reference Example 7

¹HNMR(300 MHz,CD₃OD,δppm)0.90(3H,d,J=6.3 Hz), 4.80–4.90(1H,m)7.05–7.34(4H,m),7.23(1H,d,J=1.5 Hz), 7.44–7.47(1H,m),7.82–7.84(1H,m),8.15(1H,d,J=5.1 Hz), 8.44(1H,s),8.86(1H,m)

$[\alpha]_D^{25}$: −332.3° (c1.1,CHCl₃)

EXAMPLE 14-7

(5S)-2-(4-cyano-2-pyridyl)-4,4-bis(6-fluoro-3-pyridyl)-5-methyl-2-imidazoline

Melting point: 160–162° C.
$[\alpha]_D^{25}$: −332.8° (c0.5,MeOH)

EXAMPLE 14-8

The Optical Active (5S)-2-(4-cyano-2-pyridyl)-4-(4-fluorophenyl)-5-methyl-4-(3-pyridyl)-2-imidazoline hydrochloride, Wherein the Starting Material is the Diamine Described in Reference Example 7-2

¹HNMR(300 MHz,CD₃OD,δppm): 1.15(3H,d,J=6.7 Hz), 5.54(1H,q, J=6.7 Hz),7.16–7.33(2H,m),7.33–7.45(2H,m), 8.08(1H,dd,J=5.5 Hz,8.3 Hz),8.16(1H,dd,J=1.4 Hz,4.9 Hz), 8.56(1H,brs),8.65(1H,ddd, J=1.1 Hz,2.3 Hz,8.3 Hz),8.90 (1H,dd,J=1.1 Hz,5.5 Hz),9.07(1H,dd,J=1.1 Hz,2.3 Hz),9.10 (1H,dd,J=1.0 Hz,4.9 Hz)

$[\alpha]_D^{25}$: −292.00° (c0.1,MeOH)

EXAMPLE 14-9

The Optical Active (5S)-2-(4-cyano-2-pyridyl)-4-(4-fluorophenyl)-4-(2-fluoro-4-pyridyl)-5-methyl-2-imidazoline, Wherein the Starting Material is the Diamine Described in Reference Example 8

¹HNMR(300 MHz, CDCl₃,δppm): 0.97(3H,d,J=6.6 Hz), 4.74–4.90(1H,m),6.13(1H,brs),6.96(1H,s),6.99–7.10(3H, m),7.40–7.57(2H, m),7.62(1H,dd,J=5.0 Hz,1.6 Hz),8.14 (1H,d,J=5.3 Hz),8.52–8.61(1H,m),8.76(1H,d,J=4.2 Hz)

$[\alpha]_D^{25}$: −278.80° (c0.5,CHCl₃)

EXAMPLE 15

Production of (5R)-2-(4-cyano-2-pyrimidyl)-4,4-bis(4-fluorophenyl)-5-hydroxymethyl-2-imidazoline

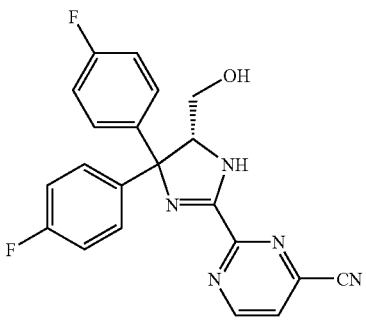

2-Cyano-4-ethoxycarbonylpyrimidine (207.3 mg) and scandium trifluoromethanesulfonate (48.8 mg) were added to a solution of (2R)-1,1-bis(4-fluorophenyl)-3-methoxymethoxy-1,2-propanediamine (303.5 mg) in toluene (2.0 mL), and the mixture was stirred at 110° C. for 4 hours. The reaction mixture was concentrated in vacuo, and then the residue was purified by silica gel column chromatography (C-300; hexane:ethyl acetate=1:1→1:2) to give (5R)-2-(4-ethoxycarbonyl-2-pyrimidyl)-4,4-bis(4-fluorophenyl)-5-[(methoxymethoxy)methyl]-2-imidazoline (279 mg). The obtained ester compound was dissolved in methanol (2 mL), and ammonia gas was passed through the solution at −78° C. for 20 minutes. Then the solution was stirred at room temperature for 20 hours. The reaction mixture was concentrated in vacuo, and then the residue was purified by silica gel column chromatography (C-300; hexane:ethyl acetate=1:1→chloroform:methanol=9:1) to give the corresponding amide compound (273 mg). Triethylamine (0.75 mL) and trifluoroacetic anhydride (0.26 mL) were added at −78° C. to a solution of the obtained amide compound in tetrahydrofuran (2 mL), and the temperature of the mixture was raised up to room temperature, followed by stirring for 7 hours. Water was added to the reaction mixture, and the mixture was extracted by ethyl acetate. The organic layer was dried over anhydrous sodium sulfate, and then sodium sulfate was removed by filtration. Then the organic solvent was evaporated in vacuo. The residue was purified by silica gel column chromatography (C-300; hexane:ethyl acetate=1:1→1:2) to give the corresponding cyano compound (178 mg). The obtained cyano compound was dissolved in tetrahydrofuran (6 mL), and 6N hydrochloric acid(6 mL) was added to the solution. Then the mixture was stirred at room temperature for 5 hours. Saturated sodium hydrogen carbonate aqueous solution was added to the reaction mixture carefully, and the mixture was extracted by ethyl acetate. The organic layer was dried over anhydrous sodium sulfate, and then sodium sulfate was removed by filtration. The organic solvent was evaporated in vacuo. The residue was purified by silica gel column chromatography (C-300; chloroform:ethyl acetate=2:1) to give the title compound (74.7 mg).

¹HNMR(300 MHz, CDCl₃,δppm): 3.10–3.40(2H,br), 4.62–4.90(1H,br),6.50–6.80(1H,br),6.95–7.08(4H,m), 7.21–7.32(2H,m),7.39–7.57(2H,br),7.32(1H,d,J=4.8 Hz), 9.13(1H,d,J=4.9 Hz)

$[\alpha]_D^{25}$: −295.1° (c0.49,MeOH)

By applying the method described in Example 15, the corresponding diamine and 2-cyano-4-ethoxycarbonylpyrimidine were cyclized and condensed, and ester group of the product was converted into a cyano group to give the following compounds.

EXAMPLE 15-1

The Optical Active (5S)-2-(4-cyano-2-pyrimidyl)-4-(4-fluorophenyl)-4-(6-fluoro-3-pyridyl)-5-methyl-2-imidazoline, Wherein the Starting Material is the Diamine Described in Reference Example 5-1

$^1$HNMR(300 MHz,CD$_3$OD,δppm): 0.85(3H,d,J=6.5 Hz), 4.80–4.93(1H,m),6.95–7.13(3H,m),7.26–7.35(2H,m), 7.88–8.10(1H,m),8.0(1 H,d,J=4.9 Hz),8.13–8.40(1H,d, J=2.0 Hz),9.18(1H,d,J=4.9 Hz)

$[α]_D^{25}$: −351.3° (c1.0,MeOH)

Reference Example 1

Production of 1,1-bis(4-fluorophenyl)-1,2-ethanediamine

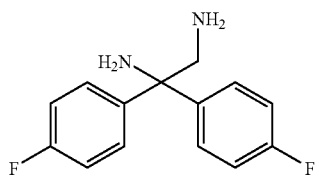

4,4'-difluorobenzophenone (25 g) was dissolved in anhydrous toluene (800 mL), and the solution was cooled at −30° C. Titanium tetrachloride (21.4 mL) was dropwise added to the solution under nitrogen, and ammonia gas was passed through the mixture for about 20 minutes. Then the mixture was warmed up to room temperature and stirred over night. Saturated potassium carbonate aqueous solution (400 mL) was added to the reaction mixture, and the mixture was stirred for an additional 1 hour. The organic layer was separated and washed with water and saturated saline once respectively. The organic layer was dried over anhydrous sodium sulfate, and then the solvent was evaporated in vacuo to give crude product of 1,1-bis(4-fluorophenyl) methanimine (31.7 g). The crude product was dissolved in anhydrous toluene (80 mL), and trimethylsilylcyanide (171.86 mL) and zinc iodide (1.83 g) were added to the solution. Then the mixture was stirred at room temperature over night. The reaction mixture was washed with saturated sodium hydrogen carbonate aqueous solution and saturated saline in this order, and dried over anhydrous sodium sulfate. Then solvent was evaporated in vacuo to obtained crude product of 2-amino-2,2-bis(4-fluorophenyl)acetonitrile (30.84 g). The crude product was dissolved in anhydrous toluene (100 mL), and then 1M diisobutylaluminum hydride-toluene solution (500 mL) was dropwise added to the solution at −78° C. Then temperature of the mixture was raised by standing to room temperature, and the mixture was stirred over night. Sodium sulfate decahydrate was added to the reaction mixture, and the resultant mixture was stirred for one hour. Moreover, anhydrous magnesium sulfate was added to the reaction mixture, and the mixture was stirred for one hour. Then insolubles were removed by filtration. The filtrate was concentrated in vacuo, and then the obtained residue was purified by silica gel column chromatography (C-300; 100% ethyl acetate→100% methanol) to give the title compound (8.55 g).

$^1$HNMR(300 MHz, CDCl$_3$,δppm): 3.32(2H,s),6.96–7.00 (4H,m),7.26–7.33(4H,m)

Reference Example 2

Production of 1-(4-fluorophenyl)-1-(1,5-naphtyridin-3-yl)-1,2-ethanediamine

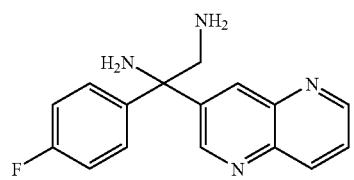

4-fluorophenyl 1,5-naphtyridin-3-yl ketone (108 mg) was dissolved in anhydrous toluene (5 mL), and the solution was cooled at −30° C. Titanium chloride (0.08 mL) was dropwise added to the solution under nitrogen, and ammonia gas was passed through the mixture for about 20 minutes. Then the mixture was warmed up to room temperature and stirred overnight. Saturated potassium carbonate aqueous solution (1 mL) was added to the reaction mixture, and the mixture was stirred for an additional 1 hour. The organic layer was separated, washed with water and saturated saline once respectively and dried over anhydrous sodium sulfate. Then the solvent was evaporated in vacuo to give crude product of (4-fluorophenyl)(1,5-naphtyridin-3-yl)-methanimine (103 mg). The crude product was dissolved in anhydrous toluene (2 mL), and trimethylsilylcyanide (0.21 mL) and 1M tetrabutylammonium fluoride-tetrahydrofuran solution (0.01 mL) were added to the solution. The mixture was stirred at room temperature for 6 days. The reaction mixture was washed with saturated sodium hydrogen carbonate aqueous solution and saturated saline once respectively and then dried over anhydrous sodium sulfate. The solvent was evaporated in vacuo to give crude product of 2-amino-2-(4-fluorophenyl)-2-(1,5-naphtyridin-3-yl)-acetonitrile. The crude product was dissolved in anhydrous toluene (2 mL). 1M Diisobutylalumium hydride-toluene solution (1.85 mL) was dropwise added to the solution at −78° C., and mixture was warmed up to 0° C. for 30 minutes. Sodium sulfate decahydrate was added to the reaction mixture, and the mixture was stirred for one hour. Moreover, anhydrous magnesium sulfate was added to the reaction mixture, and the mixture was stirred for one hour. Then insolubles were removed by filtration. The filtrate was concentrated in vacuo, and then the obtained residue was purified by silica gel column chromatography (C-300; chloroform:methanol=20:1→10:1→2:1) to give the title compound (17 mg).

$^1$HNMR(200 MHz, CD$_3$OD,δppm): 3.52(2H,s), 6.99–7.10(2H,m),7.34–7.44(2H,m),7.63(1H,dd,J=4.4 Hz,8.5 Hz),8.35–8.40(1H,m),8.41–8.43(1H,m),8.92(1H,d, J=2.3 Hz),8.98(1H,dd,J=1.7 Hz,4.4 Hz)

Reference Example 3

Production of
1,1-bis(4-fluorophenyl)-1,2-propanediamine

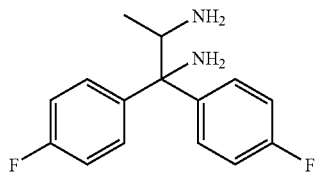

Iodine monochloride (0.40 g) was added to the suspension of sodium azide (1.01 g) in acetonitrile (6 mL) at 0° C. After the suspension was stirred for 10 minutes, the solution of 1,1-bis(4-fluorophenyl)-1-propene(1.43 g) in acetonitrile (6 mL) was added to the suspension, and the mixture was warmed up to room temperature and stirred for 38 hours. The reaction mixture was poured into water, and the mixture was extracted with diethyl ether. The extract was washed with 10% sodium thiosulfate aqueous solution, water and saturated sodium chloride aqueous solution in this order and dried over anhydrous magnesium sulfate. The solvent was evaporated in vacuo, and then the residue was purified by silica gel column chromatography (C-300; hexane:ethyl acetate=10:1) to give the desired compound, 1,1-bis(4-fluorophenyl)-2-iodopropylazide(2.16 g).

The above-mentioned iodoazide compound (40 mg) was dissolved in diethyl ether (1 mL), and lithium aluminum hydride (8 mg) was added to the solution at room temperature. Then the mixture was stirred at room temperature for 2 hours. Sodium sulfate decahydrate was added to the reaction mixture. The mixture was stirred for 30 minutes. Moreover, anhydrous magnesium sulfate was added to the reaction mixture, and the mixture was stirred for 30 minutes. Insolubles were removed by filtration, and then the filtrate was concentrated in vacuo. The obtained residue was purified by silica gel column chromatography (C-300; hexane:ethyl acetate=2:1) to give the desired compound, 2,2-bis(4-fluorophenyl)-3-methylaziridine (9 mg).

The above-mentioned aziridine compound (342 mg) was dissolved in mixture of methanol (10 mL) and water (2 mL), and sodium azide (439 mg) and ammonium chloride (155 mg) were added to the solution. The mixture was stirred at 60° C. for 40 hours. After the reaction mixture was cooled by standing, the reaction mixture was diluted with ethyl acetate, and the dilution was washed with saturated sodium hydrogen carbonate aqueous solution, water and saturated sodium chloride aqueous solution in this order, dried over anhydrous sodium sulfate, and concentrated in vacuo. The obtained residue was purified by silica gel column chromatography (C-300; hexane:ethyl acetate=2:1→1:1) to give the desired compound, 1-azido-1,1-bis(4-fluorophenyl)-2-propaneamine (251 mg). The above-mentioned azide compound (8 mg) was reduced in the presence of 10% palladium carbon catalyst (5 mg) in methanol under 1 atm hydrogen at room temperature. The catalyst was removed by filtration, and then the filtrate was concentrated in vacuo to give the title compound (7 mg).

$^1$HNMR(200 MHz, CD$_3$OD,δppm): 1.14(3H,d,J=6.5 Hz), 4.17(1H,q, J=6.5 Hz),7.00–7.13(4H,m),7.42–7.55(4H,m)

Reference Example 4

Production of (2R)-1,1-bis(4-fluorophenyl)-3-(methoxymethoxy)-1,2-propanediamine

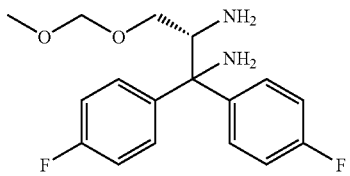

While stirring a solution of methyl (2S)-2-{[(benzyloxy)carbonyl]amino}-3-(methoxymethoxy)-propanoate (35.70 g) in tetrahydrofuran (500 mL) under nitrogen at 0° C., 1.0M 4-fluorophenylmagnesium bromide-tetrahydrofuran solution was added to the solution dropwise. Temperature of the mixture was raised to room temperature, and then the mixture was stirred for 4 hours. Saturated ammonium chloride aqueous solution (100 mL) was added to the reaction mixture, and then the reaction mixture was concentrated in vacuo. Saturated ammonium chloride aqueous solution was added to the residue, and the mixture was extracted with ethyl acetate. The organic layer was washed with saturated sodium hydrogen carbonate aqueous solution and saturated sodium chloride aqueous solution in this order and dried over anhydrous sodium sulfate. Sodium sulfate was removed by filtration, and then the organic solvent was evaporated in vacuo. The obtained residue was purified by silica gel column chromatography (C-300; hexane:ethyl acetate=9:1→5:1→3:1) to give benzyl N-{(1S)-2,2-bis(4-fluorophenyl)-2-hydroxy-1-[(methoxymethoxy)methyl]ethyl}carbamate (49.97 g) as colorless oil. The product (49.80 g) was stirred in the presence of 10% palladium carbon catalyst (2.00 g) in methanol solvent (500 mL) under 1 atm hydrogen for two days, and reaction mixture was heated up to 50° C. and stirred for 24 hours. The reaction mixture was filtered through celite, and then the obtained filtrate was concentrated in vacuo. The residue was purified by silica gel column chromatography (C-300; hexane:ethyl acetate=2:1→chloroform:methanol=5:1) to give (2S)-2-amino-1,1-bis(4-fluorophenyl)-3-(methoxymethoxy)-1-propanol (33.30 g) as yellow oil. While stirring a solution of triphenylphosphine (40.56 g) in toluene (400 mL) at 0° C., 1.0M bromine-benzene solution was added to the solution dropwise, and the mixture was stirred for 30 minutes. A solution of the above-mentioned hydroxyamine compound (20.00 g) in toluene (50 mL) and triethylamine (43.11 g) were dropwise added at 0° C. in this order. Thereafter the reaction mixture was stirred at 0° C. for 20 hours, and saturated sodium hydrogen carbonate aqueous solution was added to the reaction mixture. The resultant mixture was extracted with ethyl acetate. The organic layer was washed with saturated sodium chloride aqueous solution and dried over anhydrous sodium sulfate. Sodium sulfate was removed by filtration, and then the organic solvent was evaporated in vacuo. The obtained residue was purified by silica gel column chromatography (C-300; hexane:ethyl acetate=4:1→2:1) to give (3R)-2,2-bis(4-fluorophenyl)-3-

[(methoxymethoxy)methyl]aziridine (7.72 g) as yellow oil. Water (40 mL), sodium azide (7.45 g) and ammonium chloride (2.70 g) were added in this order to a solution of the aziridine compound (7.70 g) in N,N-dimethylformamide (80 mL), and the mixture was stirred at 100° C. for 16 hours. Moreover, sodium azide (7.45 g) was added to the reaction mixture, and the mixture was stirred at 120° C. for 24 hours. Thereafter water was added to the reaction mixture, and the mixture was extracted with diethyl ether. The organic layer was washed with saturated sodium hydrogen carbonate aqueous solution and saturated sodium chloride aqueous solution in this order and dried over anhydrous sodium sulfate. Sodium sulfate was removed by filtration, and then the organic solvent was evaporated in vacuo. The obtained residue was purified by silica gel column chromatography (C-300; hexane:ethyl acetate=3:1) to give (2R)-1-azido-1,1-bis(4-fluorophenyl)-3-(methoxymethoxy)-2-propanamine (7.68 g) as yellow oil. The obtained azide compound (7.62 g) was stirred in the presence of 5% palladium carbon catalyst (0.80 g) in methanol solvent (80 mL) under 1 atm hydrogen for 17 hours. The reaction mixture was filtered through celite and washed with ethyl acetate. The obtained filtrate was washed with saturated sodium hydrogen carbonate aqueous solution and saturated sodium chloride aqueous solution in this order and dried over anhydrous sodium sulfate. Sodium sulfate was removed by filtration, and then the organic solvent was evaporated in vacuo. The obtained residue was purified by silica gel column chromatography (C-300; ethyl acetate→chloroform:methanol=5:1) to give the title diamine (5.70 g) as pale yellow oil.

$^1$HNMR(300 MHz, CDCl$_3$,δppm): 3.26–3.33(1H,m),3.32 (3H,s),3.59(1H,dd,J=9.7 Hz,2.6 Hz),4.03(1H,dd,J=7.9 Hz,2.6 Hz),4.57(2H,dd,J=7.8 Hz,6.5 Hz),6.92–7.04(4H,m), 7.38–7.53(4H,m)

$[α]_D^{25}$: −44.3° (c1.0,CHCl$_3$)

The following compounds were produced by the method similar to the method described in the above-mentioned Reference Example 4.

Reference Example 4-1

(2S)-1,1-bis(4-fluorophenyl)-1,2-propanediamine $^1$HNMR(300 MHz, CDCl$_3$,δppm): 0.99(3H,d,J=6.4 Hz), 4.01(1H,q, J=6.4 Hz),6.92–7.03(4H,m ),7.38–7.52(4H,m)

Reference Example 4-2

(2S)-1,1-bis(6-fluoro-3-pyridyl)-1,2-propanediamine $^1$HNMR(300 MHz, CDCl$_3$,δppm): 1.04(3H,d,J=6.3 Hz), 4.09(1H,q, J=6.3 Hz),6.88(2H,dd,J=8.5 Hz,3.1 Hz),7.88 (1H,ddd,J=8.5 Hz,8.0 Hz,2.5 Hz),7.96(1H,ddd,J=8.5 Hz,8.0 Hz,2.5 Hz),8.35(1H,d,J=2.5 Hz),8.40(1H,d,J=2.5 Hz)

Reference Example 4-3

(2S)-1,1-bis(2-fluoro-4-pyridyl)-1,2-propanediamine $^1$HNMR(300 MHz, CDCl$_3$,δppm): 1.02(3H,d,J=6.3 Hz), 4.10(1H,q, J=6.3 Hz),7.12(1H,s),7.23(1H,s),7.27(1H,d, J=5.4 Hz),7.35(1H,d,J=5.7 Hz),8.16(1H,d,J=5.7 Hz),8.17 (1H,d,J=5.4 Hz)

Reference Example 5

Production of (2S)-1-(4-fluorophenyl)-1-(6-fluoro-3-pyridyl)-1,2-propanediamine

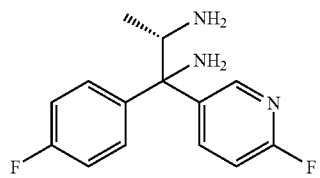

The solution of t-buthyl N-{(1S)-2-[methoxy(methyl) amino]-1-methyl-2-oxoethyl}-carbamate (50 g) in tetrahydrofuran (700 mL) was dropwise added slowly at 0° C. to 2.5M 4-fluorophenylmagnesium bromide-tetrahydrofuran solution (300 mL) prepared separately, and then the reaction mixture was stirred at room temperature for 14 hours. After the reaction mixture was cooled to 0° C., saturated sodium hydrogen carbonate aqueous solution was added to the reaction mixture, and then the mixture was extracted with ether twice. The organic layer was washed with saturated sodium hydrogen carbonate aqueous solution and saturated sodium chloride aqueous solution in this order and dried over anhydrous sodium sulfate. Sodium sulfate was removed by filtration, and then the organic solvent was evaporated in vacuo. The obtained residue was purified by silica gel column chromatography (C-300; hexane:ethyl acetate=4:1) to give t-butyl N-[(1S)-2-(4-fluorophenyl)-1-methyl-2-oxoethyl]carbamate (57.75 g) as pale yellow solid. The solution of the obtained ketone compound (61.20 g) in ethylene glycol dimethyl ether (500 mL) solution was dropwise added to the solution of 6-fluoro-3-pyridyllithium in diethyl ether (prepared by the reaction of 5-bromo-2-fluoropyridine (59 mL) and 1.6M butyllithium-hexane solution (358 mL) in diethyl ether (1.5 L) solvent at −78° C.) at −78° C. Thereafter the reaction mixture was stirred at −78° C. for 30 minutes, and temperature of the reaction mixture was raised to 0° C. Saturated ammonium chloride aqueous solution was added to the reaction mixture, and the mixture was stirred at room temperature for an additional 15 minutes. After aqueous layer was removed, the organic layer was washed with water and saturated sodium chloride aqueous solution in this order and dried over anhydrous sodium sulfate. Sodium sulfate was removed by filtration, and then the organic solvent was evaporated in vacuo. The residue was dissolved in a little ethyl acetate, and excess diisopropyl ether was added to the solution to precipitate t-butyl N-[(1S)-2-(4-fluorophenyl)-2-(6-fluoro-3-pyridyl)-2-hydroxy-1-methylethyl]carbamate. The precipitate was filtered (yield 74.35 g). The precipitate was treated with 4N hydrogen chloride-ethyl acetate solution to give (2S)-2-amino-1-(4-fluorophenyl)-1-(6-fluoro-3-pyridyl)-1-propanol (32.8 g). The obtained hydroxyamino compound was converted into aziridine by the method similar to the method described in Reference Example 4 to give 2-fluoro-5-[(3S)-2-(4-fluorophenyl)-3-methyl-2-aziridinyl]-pyridine. The obtained aziridine compound was converted into azide by the method similar to the method described in Reference Example 4, and then the azide compound was reduced by the addition of hydrogen to give the title diamine. Besides, the ratio of diastereomers in 2nd position of aziridine ring is about 3:2, and the diastereomers can be separated by silica gel column chromatography (C-300; hexane:ethyl acetate=6:4→4:6).

Reference Example 5-1

Production of the Optical Active (2S)-1-(4-fluorophenyl)-1-(6-fluoro-3-pyridyl)-1,2-propanediamine

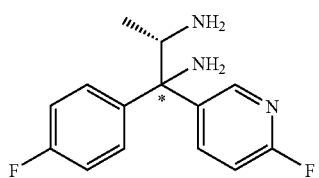

The mixture of diastereomers of 2-fluoro-5-[(3S)-2-(4-fluorophenyl)-3-methyl-2-aziridinyl]pyridine obtained in Reference Example 5 were separated by silica gel column chromatography. The aziridine compound eluted first was treated by the method similar to the method described in Reference Example 4 to give the optical active title diamine.

$^1$HNMR(300 MHz, CDCl$_3$,δppm): 1.00(3H,d,J=6.3 Hz), 4.65(1H,q, J=6.3 Hz),6.85(1H,dd,J=3.0 Hz,8.7 Hz),7.00 (2H,t,J=8.4 Hz),7.43(2H,dd,J=5.4 Hz,9.0 Hz),7.97(1H,t, J=8.4 Hz),8.40(1H,d,J=2.7 Hz)

Reference Example 5-2

Production of the Optical Active (2S)-1-(4-fluorophenyl)-1-(6-fluoro-3-pyridyl)-1,2-propanediamine(Epimer in 1st Position of Reference Example 5–1)

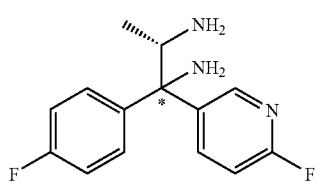

The mixture of diastereomers of 2-fluoro-5-[(3S)-2-(4-fluorophenyl)-3-methyl-2-aziridinyl]pyridine obtained in Reference Example 5 was separated by silica gel column chromatography. The aziridine compound eluted secondly was treated by the method similar to the method described in Reference Example 4 to give the optical active title diamine.

$^1$HNMR(300 MHz, CDCl$_3$,δppm): 1.02(3H,d,J=6.3 Hz), 4.05(1H,q, J=6.3 Hz),6.84(1H,dd,J=8.5 Hz,3.1 Hz),7.01 (2H,dd,J=8.9 Hz,8.5 Hz),7.49(2H,dd,J=8.9 Hz,5.2 Hz),7.87 (1H,ddd,J=8.5 Hz,8.0 Hz,2.6 Hz),8.34(1H,d,J=2.6 Hz)

Reference Example 6

Production of (2R)-1-(4-fluorophenyl)-1-(6-fluoro-3-pyridyl)-3-(methoxymethoxy)-1,2-propanediamine

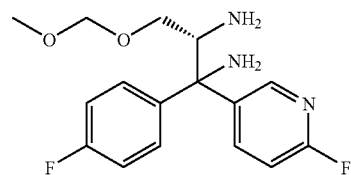

The title compound was produced by the method similar to the method described in Reference Example 5 via 2-fluoro-5-{(3R)-2-(4-fluorophenyl)-3-[(methoxymethoxy)methyl]-2-aziridinyl}pyridine. Said intermediate, aziridine can be separated by silica gel column chromatography.

Reference Example 6-1

Production of the Optical Active (2R)-1-(4-fluorophenyl)-1-(6-fluoro-3-pyridyl)-3-(methoxymethoxy)-1,2-propanediamine

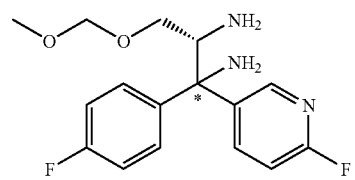

The mixture of diastereomers of 2-fluoro-5-{(3R)-2-(4-fluorophenyl)-3-[(methoxymethoxy)methyl]-2-aziridinyl}pyridine obtained in Reference Example 6 were separated by silica gel column chromatography (eluted with mixed solvent of hexane and ethyl acetate). The aziridine compound eluted first was treated by the method similar to the method described in Reference Example 4 to give the optical active title diamine.

$^1$HNMR(300 MHz, CDCl$_3$,δppm): 3.31(4H,m),3.56(1H, dd,J=2.3 Hz,9.8 Hz),4.03(1H,dd,J=2.5 Hz,7.9 Hz),4.56(2H, s),6.85(1H,dd,J=3.0 Hz,6.5 Hz),7.00(2H,m),7.39(2H,m), 7.94(1H,dt,J=2.7 Hz,7.8 Hz),8.39(1H,s)

Reference Example 7

Production of the Optical Active (2S)-1-(4-fluorophenyl)-1-(2-fluoro-4-pyridyl)-1,2-propanediamine

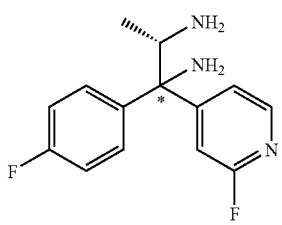

The intermediate in Reference Example 5, t-butyl N-[(1S)-2-(4-fluorophenyl)-1-methyl-2-oxoethyl]carbamate and 2-methyl-2-propanesulfinamide were condensed in the presence of a dehydrating agent to give t-butyl N-[(1S)-2-[(t-butylsulfinyl)imino]-2-(4-fluorophenyl)-1-methylethyl]carbamate. 1.0M trimethylaluminum-hexane solution (0.43 mL) was added to the solution of said sulfinylimine compound (80 mg) in toluene (2 mL) at −78° C., and the mixture was stirred for 5 minutes. The obtained solution was dropwise added slowly to 2-fluoro-4-pyridyllithium solution (prepared by the reaction of 4-fluoro-2-bromopyridine (114 mg) and 1.56M butyllithium-hexane solution (0.46 mL) in diethyl ether solvent (3 mL) at −78° C.) at −78° C. Thereafter tetrahydrofuran (3 mL) was added to the reaction mixture, and then the reaction mixture was stirred at −78° C. for 2.5 hours. Saturated sodium chloride aqueous solution was added to the reaction mixture, and temperature of the reaction mixture was raised to room temperature. The obtained reaction mixture was filtered through celite, and then the organic layer of filtrate was dried over anhydrous magnesium sulfate. Magnesium sulfate was removed by filtration, and then the organic solvent was evaporated in vacuo. The obtained residue was purified by silica gel column chromatography (C-300; hexane:ethyl acetate=2:1) to give the optical active t-butyl N-[(1S)-2-[(t-butylsulfinyl)amino]-2-(4-fluorophenyl)-2-(2-fluoro-4-pyridyl)-1-methylethyl]carbamate (49 mg). The product was treated with 4N hydrogen chloride-dioxane solution to give the optical active title diamine (31 mg).

$^1$HNMR(300 MHz, CDCl$_3$,δppm): 1.03(3H,d,J=6.3 Hz), 1.91(4H,brs),4.10(1H,q,J=6.3 Hz),6.98–7.48(6H,m),8.12 (1H,d,J=5.1 Hz)

Reference Example 7-1

Production of the Optical Active (2S)-1-(4-fluorophenyl)-1-(1,5-naphtyridin-3-yl)-1,2-propanediamine

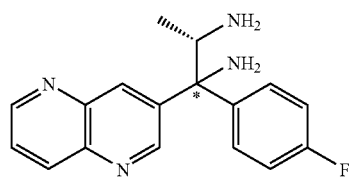

1,5-naphtyridin-3-yllithium was reacted with t-butyl N-[(1S)-2-[(t-butylsulfinyl)imino]-2-(4-fluorophenyl)-1-methylethyl]carbamate by the method similar to the method described in Reference Example 7, and the protecting groups of the product were removed under acidic condition to give the optical active title diamine.

$^1$HNMR(300 MHz, CDCl$_3$,δppm): 1.06(3H,d,J=6.3 Hz), 4.25(1H,q, J=6.3 Hz),7.00(2H,t,J=8.6 Hz),7.45–7.55(2H, m),7.60(1H,dd,J=4.2 Hz,8.5 Hz),8.35(1H,d,J=8.6 Hz),8.57 (1H,d,J=1.4 Hz),8.95(1H,dd,J=1.4 Hz,4.2 Hz),9.13(1H,d, J=2.2 Hz)

Reference Example 7-2

Production of the Optical Active (2S)-1-(4-fluorophenyl)-1-(3-pyridyl)-1,2-propanediamine

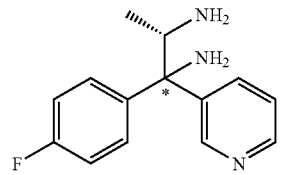

3-pridyllithium was reacted with t-butyl N-[(1S)-2-[(t-butylsulfinyl)imino]-2-(4-fluorophenyl)-1-methylethyl]carbamate by the method similar to the method described in Reference Example 7, and the protecting groups of the product were removed under acidic condition to give the optical active title diamine.

$^1$HNMR(300 MHz, CDCl$_3$,δppm): 1.01(3H,d,J=6.3 Hz), 4.08(1H,q, J=6.3 Hz),6.99(2H,dd,J=8.6 Hz,9.0 Hz),7.23 (1H,dd,J=4.7 Hz,8.1 Hz),7.45(2H,dd,J=5.3 Hz,9.0 Hz),7.86 (1H,ddd,J=1.6 Hz,2.5 Hz,8.1 Hz),8.44(1H,dd,J=1.6 Hz,4.7 Hz),8.79(1H,d,J=2.5 Hz)

Reference Example 8

Production of the Optical Active (2S)-1-(4-fluorophenyl)-1-(2-fluoro-4-pyridyl)-1,2-propanediamine (Epimer in 1st Position of the Compound Described in Reference Example 7)

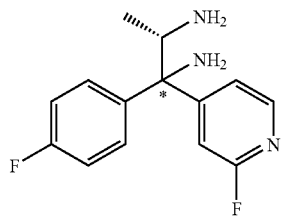

4-fluorophenyllithium was reacted with t-butyl N-[(1S)-2-[(t-butylsulfinyl)imino]-2-(2-fluoro-4-pyridyl)-1-methylethyl]carbamate by the method similar to the method described in Reference Example 7, and the protecting groups of the product were removed under acidic condition to give the optical active title diamine.

$^1$HNMR(300 MHz, CDCl$_3$,δppm): 0.98(3H,d,J=6.4 Hz), 4.07(1H,q, J=6.4 Hz),6.98–7.07(2H,m),7.10(1H,s),7.24(1H, dt,J=5.4 Hz,1.7 Hz),7.48–7.58(2H,m),8.11(1H,d,J=5.3 Hz)

Reference Example 8-1

Production of the Optical Active (2S)-1-(4-fluorophenyl)-1-(1,5-naphtyridin-3-yl)-1,2-propanediamine (Epimer in 1st Position of the Compound Described in Reference Example 7-1)

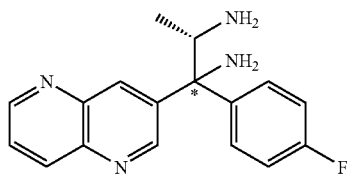

4-fluorophenyllithium was reacted with t-butyl N-[(1S)-2-[(t-butylsulfinyl)imino]-2-(1,5-naphtyridin-3-yl)-1-methylethyl]carbamate by the method similar to the method described in Reference Example 7, and the protecting groups of the product were removed under acidic condition to give the optical active title diamine.

$^1$HNMR(300 MHz, CDCl$_3$,δppm): 1.09(1H,d,J=6.3 Hz), 1.85–2.45(4H,br),4.26(1H,q,J=6.3 Hz),7.01(2H,t,J=8.6 Hz), 7.46–7.65(3H,m),8.35(1H,d,J=8.6 Hz),8.52(1H,d,J=1.8 Hz),8.96(1H,dd,J=4.1 Hz, 1.5 Hz),9.07(1H,d,J=2.2 Hz)

Preparation Example 1

The compound of Example 1 20.0 g, lactose 417 g, crystalline cellulose 80 g and partly pregelatinized starch 80 g were mixed by using V-type mixer, and magnesium stearate 3.0 g was added to the mixture. The resultant mixture was further mixed. The mixture was compressed in a usual manner to give 3000 tablets, diameter of each tablet being 7.0 mm and weight of each tablet being 150 mg.

Content Per a Tablet(150 mg)

| | |
|---|---|
| Compound of Example 1 | 5.0 mg |
| Lactose | 104.25 mg |
| Crystalline cellulose | 20.0 mg |
| Partly pregelatinized starch | 20.0 mg |
| Magnesium stearate | 0.75 mg |

Preparation Example 2

Hydroxypropylcellulose 2910 10.8 g and polyethylene glycol 6000 2.1 g were dissolved in purified water 172.5 g, and titanium dioxide 2.1 g was dispersed in the solution to prepare coating solution. 2500 tablets prepared separately in Preparation Example 1 were spray-coated with the coating solution by using HYCOATERMINI to give film-coated tablets, the weight of each tablet being 155 mg.

Content Per a Tablet(155 mg)

| | |
|---|---|
| Compound of Example 1 | 150 mg |
| Hydroxypropylcellulose 2910 | 3.6 mg |
| Polyethylene glycol 6000 | 0.7 mg |
| Titanium dioxide | 0.7 mg |

INDUSTRIAL APPLICABILITY

The compounds of the present invention are useful as agents for the treatment of various diseases which NPY relates to, that is, for example, cardiovascular disorders exemplified by hypertension, nephropathy, heart diseases, vasospasm and arteriosclerosis, central nervous system disorders exemplified by bulimia, depression, anxiety, seizure, epilepsy, dementia, pain, alcoholism and drug withdrawal, metabolic diseases exemplified by obesity, diabetes, hormone abnormality, hypercholesterolemia and hyperlipidemia, sexual and reproductive dysfunction, gastro-intestinal disorder such as the inhibition of gastro-intestinal motility, respiratory disorder, inflammation, or glaucoma, and the like since they exhibit NPY antagonistic activities and are excellent in pharmacokinetics such as penetration to brain and cerebrospinal fluid.

The invention claimed is:

1. A compound represented by the general formula (I):

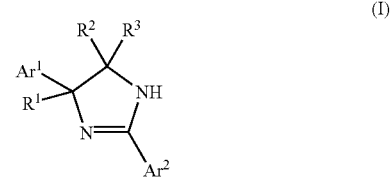

wherein Ar$^1$, Ar$^2$ and Ar$^3$ represent independently aryl which may be substituted, the substituent being selected from the group consisting of cyano, halogen atom, nitro, lower alkyl, halo(lower)alkyl, hydroxy (lower)alkyl, cyclo(lower)alkyl(lower)alkyl, lower alkenyl, lower alkylamino, di-lower alkylamino, lower alkanoylamino, lower alkylsulfonylamino, arylsulfonylamino, hydroxy, lower alkoxy, halo(lower)alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl;

R$^1$ represents a group represented by the formula of —Ar$^3$;

R$^2$ and R$^3$ represent independently hydrogen atom, cyclo(lower)alkyl, lower alkenyl or lower alkyl which may be substituted, the substituent being selected from the group consisting of halogen atom, lower alkylamino, di-lower alkylamino, lower alkanoylamino, hydroxy, lower alkoxy, formyl, lower alkoxycarbonyl, lower alkylcarbamoyl and di-lower alkylcarbamoyl; provided that when both R$^2$ and R$^3$ represent hydrogen atom, Ar$^1$, Ar$^2$ and R$^1$ do not represent simultaneously an unsubstituted phenyl group;

or a salt or pharmaceutically acceptable ester of a carboxyl group thereof.

2. The compound as claimed in claim 1, wherein Ar$^2$ is phenyl which contains substituent(s) selected from the group consisting of cyano, halogen atom, nitro, lower alkyl, halo(lower)alkyl, lower alkoxy, halo(lower)alkoxy, formyl, lower alkanoyl, lower alkoxycarbonyl and lower alkylsulfonyl.

3. The compound as claimed in claim 2, wherein Ar$^1$ is phenyl which has substituent(s) selected from the group consisting of halogen atom, halo(lower)alkyl and halo(lower)alkoxy.

4. The compound as claimed in claim 3, wherein both R² and R³ are hydrogen atom.

5. The compound as claimed in claim 3, wherein either R² or R³ is hydrogen atom and the other is lower alkyl which may have substituent(s) selected from the group consisting of halogen atom, lower alkylamino, di-lower alkylamino, lower alkanoylamino, hydroxy, lower alkoxy, formyl, lower alkoxycarbonyl, lower alkylcarbanoyl and di-lower alkylcarbamoyl.

6. The compound as claimed in claim 2, wherein Ar³ is phenyl which may have substituent(s) selected from the group consisting of halogen atom, lower alkyl, hydroxy (lower)alkyl, lower alkenyl, di-lower alkylamino, lower alkoxy, halo(lower)alkoxy, lower alkanoyl and aryl.

7. The compound as claimed in claim 1, which is
2-(3-cyanophenyl)-4,4-bis(4-fluorophenyl)-2-imidazoline,
2-(3-cyanophenyl)-4,4-bis(4-fluorophenyl)-5-methyl-2-imidazoline,
2-(3-cyanophenyl)-4,4-bis(4-fluorophenyl)-5-hydroxymethyl-2-imidazoline,
2-(3-cyanophenyl)-4,4-bis(3-fluorophenyl)-2-imidazoline,
4-(4-bromophenyl)-2-(3-cyanophenyl)-4-phenyl-2-imidazoline,
4,4-bis(4-chlorophenyl)-2-(3-cyanophenyl)-2-imidazoline,
4-(4-chlorophenyl)-2-(3-cyanophenyl)-4-phenyl-2-imidazoline,
2-(3-cyanophenyl)-4-(4-fluorophenyl)-4-phenyl-2-imidazoline,
2-(3-cyanophenyl)-4-phenyl-4-(4-vinylphenyl)-2-imidazoline,
2-(3-cyanophenyl)-4-(4-methylphenyl)-4-phenyl-2-imidazoline,
2-(3-cyanophenyl)-4-(3-methylphenyl)-4-phenyl-2-imidazoline,
4,4-bis(4-fluorophenyl)-2-(3-nitrophenyl)-2-imidazoline,
2-(3-cyanophenyl)-4-(4-methoxyphenyl)-4-phenyl-2-imidazoline,
4-(3-chlorophenyl)-2-(3-cyanophenyl)-4-phenyl-2-imidazoline,
2-(3-cyanophenyl)-4-phenyl-4-(4-trifluoromethylphenyl)-2-imidazoline,
2-(3-cyanophenyl)-4-(3-methoxyphenyl)-4-phenyl-2-imidazoline,
2-(3-cyanophenyl)-4-(3,4-dimethylphenyl)-4-phenyl-2-imidazoline,
2-(3-cyanophenyl)-4-(4-fluorophenyl)-4-(3-vinylphenyl)-2-imidazoline,
4-(3-bromophenyl)-2-(3-cyanophenyl)-4-(4-fluorophenyl)-2-imidazoline,
4-(2-chlorophenyl)-2-(3-cyanophenyl)-4-phenyl-2-imidazoline,
2-(3-cyanophenyl)-4-(4-dimethylaminophenyl)-4-phenyl-2-imidazoline,
2-(3-cyanophenyl)-4-(4-formylphenyl)-4-phenyl-2-imidazoline,
2-(3-cyanophenyl)-4,4-bis(4-methoxyphenyl)-2-imidazoline,
2-(3-cyanophenyl)-4-(4-fluorophenyl)-4-(3-formylphenyl)-2-imidazoline,
4,4-bis(4-fluorophenyl)-2-(3-methylsulfonylphenyl)-2-imidazoline,
4,4-bis(4-fluorophenyl)-2-(3-formylphenyl)-2-imidazoline,
2-(3-cyanophenyl)-4-(2-methylphenyl)-4-phenyl-2-imidazoline,
2-(3-cyanophenyl)-4-(4-fluorophenyl)-4-(3-hydroxymethylphenyl)-2-imidazoline,
4-(4-biphenylyl)-2-(3-cyanophenyl)-4-phenyl-2-imidazoline,
2-(3-cyanophenyl)-4-(2-methoxyphenyl)-4-phenyl-2-imidazoline,
2-(3-chlorophenyl)-4,4-bis(4-fluorophenyl)-2-imidazoline,
4,4-bis(4-fluorophenyl)-2-(3-trifluoromethylphenyl)-2-imidazoline,
2-(3-fluorophenyl)-4,4-bis(4-fluorophenyl)-2-imidazoline,
4,4-bis(4-fluorophenyl)-2-(3-trifluoromethoxyphenyl)-2-imidazoline,
4,4-bis(4-fluorophenyl)-2-(3-methylphenyl)-2-imidazoline,
2-(3-bromophenyl)-4,4-bis(4-fluorophenyl)-2-imidazoline, or
2-(3-cyanophenyl)-4,4-bis(4-fluorophenyl)-5-(1-hydroxyethyl)-2-imidazoline.

8. A process for producing a compound of the general formula (I):

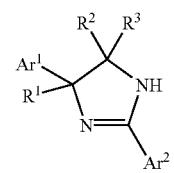

wherein Ar¹, Ar² and A³ represent independently aryl which may be substituted, the substituent being selected from the group consisting of cyano, halogen atom, nitro, lower alkyl, halo(lower)alkyl, hydroxy (lower)alkyl, cyclo(lower)alkyl(lower)alkyl, lower alkenyl, lower alkylamino, di-lower alkylamino, lower alkanoylamino, lower alkylsulfonylamino, arylsulfonylamino, hydroxy, lower alkoxy, halo(lower)alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl;

R¹ represents a group represented by the formula of —Ar³;

R² and R³ represent independently hydrogen atom, cyclo (lower)alkyl, lower alkenyl or lower alkyl which may be substituted, the substituent being selected from the group consisting of halogen atom, lower alkylamino, di-lower alkylamino, lower alkanoylamino, hydroxy, lower alkoxy, formyl, lower alkoxycarbonyl, lower alkylcarbamoyl and di-lower alkylcarbamoyl; provided that when both R² and R³ represent hydrogen atom, Ar¹, Ar² and R¹ do not represent simultaneously an unsubstituted phenyl group;

or a salt or pharmaceutically acceptable ester of a carboxyl group thereof, which comprises reacting a compound of the general formula (II):

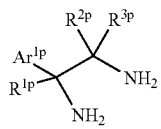

(II)

wherein $Ar^{1p}$ and $Ar^{3p}$ represent independently aryl which may be substituted, the substituent being selected from the group consisting of cyano, halogen atom, nitro, lower alkyl, halo(lower)alkyl, cyclo(lower)alkyl(lower)alkyl, loweralkenyl, di-lower alkylamino, lower alkoxy, halo(lower)alkoxy, aryloxy, heteroaryloxy, lower alkylthio, formyl, lower alkanoyl, lower alkoxycarbonyl, di-lower alkylcarbamoyl, lower alkylsulfonyl, arylsulfonyl, aryl, heteroaryl and an optionally protected, hydroxy(lower)alkyl, lower alkylamino, lower alkanoylamino, lower alkylsulfonylamino, arylsulfonylamino, hydroxy, carboxyl, carbamoyl, or lower alkylcarbamoyl group;

$R^{1p}$ represents a group represented by the formula of —$Ar^{3p}$;

$R^{2p}$ and $R^{3p}$ represent independently hydrogen atom, cyclo(lower)alkyl, lower alkenyl or lower alkyl which may be substituted, the substituent being selected from the group consisting of halogen atom, di-lower alkylamino, lower alkoxy, formyl, lower alkoxycarbonyl, di-lower alkylcarbamoyl and an optionally protected, lower alkylamino, lower alkanoylamino, hydroxy or lower alkylcarbamoyl group;

with an acid addition salt of the compound represented by the general formula (III)

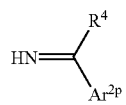

(III)

wherein $Ar^{2p}$ represents aryl which may be substituted, the substituent being selected from the group consisting of cyano, halogen atom, nitro, lower alkyl, halo(lower)alkyl, cyclo(lower)alkyl(lower)alkyl, lower alkenyl, di-lower alkylamino, lower alkoxy, halo(lower)alkoxy, aryloxy, heteroaryloxy, lower alkylthio, formyl, lower alkanoyl, lower alkoxycarbonyl, di-lower alkylcarbamoyl, lower alkylsulfonyl, arylsulfonyl, aryl, heteroaryl and an optionally protected, hydroxy(lower)alkyl, lower alkylamino, lower alkanoylamino, lower alkylsulfonylamino, arylsulfonylamino, hydroxy, carboxyl, carbamoyl, or lower alkylcarbamoyl group;

$R^4$ represents amino or lower alkoxy;

to provide a compound of the general formula (IV):

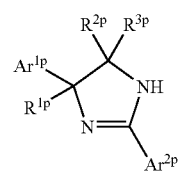

(IV)

wherein $Ar^{1p}$, $Ar^{2p}$, $R^{1p}$ and $R^{3p}$ have the same meanings as described above; optionally followed by cleavage of a protecting group.

9. A method of treating bulimia, obesity or diabetes comprising administering to a patient in need thereof an effective amount of a compound of the general formula (I):

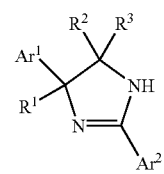

(I)

wherein $Ar^1$, $Ar^2$ and $Ar^3$ represent independently aryl which may be substituted, the substituent being selected from the group consisting of cyano halogen atom, nitro, lower alkyl, halo(lower)alkyl, hydroxy (lower)alkyl, cyclo(lower)alkyl(lower)alkyl, lower alkenyl, lower alkylamino, di-lower alkylamino, lower alkanoylamino, lower alkylsulfonylamino, arylsulfonylamino, hydroxy, lower alkoxy, halo(lower)alkoxy, aryloxy, heteroaryloxy, lower alkylthio, carboxyl, formyl, lower alkanoyl, lower alkoxycarbonyl, carbamoyl, lower alkylcarbamoyl, di-lower alkylcarbamoyl, lower alkylsulfonyl, arylsulfonyl, aryl and heteroaryl;

$R^1$ represents a group represented by the formula of —$Ar^3$;

$R^2$ and $R^3$ represent independently hydrogen atom, cyclo(lower)alkyl, lower alkenyl or lower alkyl which may be substituted, the substituent being selected from the group consisting of halogen atom, lower alkylamino, di-lower alkylamino, lower alkanoylamino, hydroxy, lower alkoxy, formyl, lower alkoxycarbonyl, lower alkylcarbamoyl and di-lower alkylcarbamoyl;

provided that when both $R^2$ and $R^3$ represent hydrogen atom, $Ar^1$, $Ar^2$ and $R^1$ do not represent simultaneously an unsubstituted phenyl group;

or a salt or pharmaceutically acceptable ester of a carboxyl group thereof.

* * * * *